United States Patent
Andersen et al.

(10) Patent No.: US 10,724,022 B2
(45) Date of Patent: *Jul. 28, 2020

(54) ALPHA-AMYLASE VARIANTS AND POLYNUCLEOTIDES ENCODING SAME

(71) Applicant: Novozymes A/S, Bagsvaerd (DK)

(72) Inventors: Carsten Andersen, Vaerloese (DK); Signe E. Larsen, Lyngby (DK); Esben Peter Friis, Herlev (DK); Pernille Ollendorff Micheelsen, Frederiksberg (DK); Anders Viksoee-Nielsen, Joerlunde (DK); Randy Deinhammer, Wake Forest, NC (US); Xinyu Shen, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/808,697

(22) Filed: Mar. 4, 2020

(65) Prior Publication Data

US 2020/0208130 A1 Jul. 2, 2020

Related U.S. Application Data

(60) Division of application No. 16/425,184, filed on May 29, 2019, now Pat. No. 10,619,141, which is a division of application No. 15/062,644, filed on Mar. 7, 2016, now Pat. No. 10,351,836, which is a continuation of application No. 14/346,107, filed as application No. PCT/EP2012/070578 on Oct. 17, 2012, now abandoned.

(60) Provisional application No. 61/548,416, filed on Oct. 18, 2011.

(30) Foreign Application Priority Data

Oct. 17, 2011 (EP) .................................. 11185479

(51) Int. Cl.
| | |
|---|---|
| *C12N 9/24* | (2006.01) |
| *C12P 7/06* | (2006.01) |
| *C12P 19/14* | (2006.01) |
| *C11D 3/386* | (2006.01) |
| *C12N 9/28* | (2006.01) |
| *C12N 15/09* | (2006.01) |
| *C12N 9/26* | (2006.01) |

(52) U.S. Cl.
CPC ............ *C12N 9/2417* (2013.01); *C11D 3/386* (2013.01); *C12N 9/2408* (2013.01); *C12P 7/06* (2013.01); *C12P 19/14* (2013.01); *C12Y 302/01001* (2013.01); *Y02E 50/17* (2013.01)

(58) Field of Classification Search
CPC ..... C12N 9/2417; C12N 9/2408; C12P 19/14; C12P 7/06; C11D 3/386; C12Y 302/01001

See application file for complete search history.

(56) References Cited

U.S. PATENT DOCUMENTS

| | | |
|---|---|---|
| 6,197,565 B1 | 3/2001 | Svendsen et al. |
| 6,410,295 B1 | 6/2002 | Andersen et al. |
| 6,440,716 B1 | 8/2002 | Svendsen et al. |
| 6,887,986 B1 | 5/2005 | Svendsen et al. |
| 7,498,158 B2 | 3/2009 | Svendsen et al. |
| 9,334,485 B2 | 5/2016 | Andersen |
| 10,017,752 B2 | 7/2018 | Andersen |
| 10,351,836 B2 | 7/2019 | Andersen |
| 2002/0197698 A1 | 12/2002 | Hagihara |
| 2004/0091994 A1 | 5/2004 | Andersen |
| 2009/0314286 A1 | 12/2009 | Cuevas |
| 2012/0045817 A1 | 2/2012 | Estell |
| 2019/0316105 A1 | 10/2019 | Andersen |

FOREIGN PATENT DOCUMENTS

| | | |
|---|---|---|
| EP | 1 676 913 A2 | 7/2006 |
| WO | 02/10355 A2 | 2/2002 |
| WO | 2007/007053 A1 | 1/2007 |
| WO | 2010/115021 A2 | 10/2010 |
| WO | 2011/080352 A1 | 7/2011 |

OTHER PUBLICATIONS

Meinhardt et al., EBI Accession No. CAJ70704 (2006).
Olek et al., GenBank Accession No. ABF61440 (2001).
Yuan et al., Chinese High Technology Letters, vol. 15, No. 11, pp. 63-68 (2005).

*Primary Examiner* — Maryam Monshipouri
(74) *Attorney, Agent, or Firm* — Elias Lambiris

(57) ABSTRACT

The present invention relates to alpha-amylase variants. The present invention also relates to polynucleotides encoding the variants; nucleic acid constructs, vectors, and host cells comprising the polynucleotides; and methods of using the variants.

21 Claims, 4 Drawing Sheets
Specification includes a Sequence Listing.

```
                    1                                              50
SEQ ID NO: 1    (1) ---ANLNGTLMQYFEWYMPNDGQHWRRLQNDSAYLAEHGITAVWIPPAYK
SEQ ID NO: 2    (1) --AAPFNGTMMQYFEWYLPDDGTLWTKVANEANNLSSLGITALWLPPAYK
SEQ ID NO: 3    (1) ANTAPINETMMQYFEWDLPNDGTLWTKVKNEAANLSSLGITALWLPPAYK
SEQ ID NO: 4    (1) ---VPVNGTMMQYFEWYLPDDGTLWTKVANNAQSLANLGITALWLPPAYK
SEQ ID NO: 5    (1) -GSVPVNGTMMQYFEWYLPDDGTLWTKVANNAQSLANLGITALWLPPAYK
SEQ ID NO: 6    (1) -----VNGTLMQYFEWYTPNDGQHWKRLQNDAEHLSDIGITAVWIPPAYK
SEQ ID NO: 7    (1) -HHNGTNGTMMQYFEWYLPNDGNHWNRLRDDAANLKSKGITAVWIPPAWK
SEQ ID NO: 8    (1) -HHNGTNGTMMQYFEWHLPNDGNHWNRLRDDASNLRNRGITAIWIPPAWK
SEQ ID NO: 9    (1) -HHNGTNGTMMQYFEWYLPNDGNHWNRLRSDASNLKDKGISAVWIPPAWK
SEQ ID NO: 10   (1) -HHNGTNGTMMQYFEWYLPNDGNHWNRLRSDASNLKDKGITAVWIPPAWK
SEQ ID NO: 11   (1) -HHNGTNGTMMQYYEWYLPNDGNHWNRLNSDASNLKSKGITAVWIPPAWK
SEQ ID NO: 12   (1) ---DGLNGTMMQYYEWHLENDGQHWNRLHDDAAALSDAGITAIWIPPAYK
SEQ ID NO: 13   (1) ---ANLNGTLMQYFEWYMPNDGQHWKRLQNDSAYLAEHGITAVWIPPAYK
SEQ ID NO: 14   (1) -----VNGTLMQYFEWYTPNDGQHWKRLQNDAEHLSDIGITAVWIPPAYK 51                                             100
SEQ ID NO: 1    (48)  GTSQADVGYGAYDLYDLGEFHQKGTVRTKYGTKGELQSAIKSLHSRDINV
SEQ ID NO: 2    (49)  GTSRSDVGYGVYDLYDLGEFNQKGTVRTKYGTKAQYLQAIQAAHAAGMQV
SEQ ID NO: 3    (51)  GTSQSDVGYGVYDLYDLGEFNQKGTIRTKYGTKTQYIQAIQAAKAAGMQV
SEQ ID NO: 4    (48)  GTSSSDVGYGVYDLYDLGEFNQKGTVRTKYGTKTQYIQAIQAAHTAGMQV
SEQ ID NO: 5    (50)  GTSSSDVGYGVYDLYDLGEFNQKGTVRTKYGTKTQYIQAIQAAHTAGMQV
SEQ ID NO: 6    (46)  GLSQSDNGYGPYDLYDLGEFQQKGTVRTKYGTKSELQDAIGSLHSRNVQV
SEQ ID NO: 7    (50)  GTSQNDVGYGAYDLYDLGEFNQKGTVRTKYGTRNQLQAAVTSLKNNGIQV
SEQ ID NO: 8    (50)  GTSQNDVGYGAYDLYDLGEFNQKGTVRTKYGTRSQLESAIHALKNNGVQV
SEQ ID NO: 9    (50)  GASQNDVGYGAYDLYDLGEFNQKGTIRTKYGTRNQLQAAVNALKSNGIQV
SEQ ID NO: 10   (50)  GASQNDVGYGAYDLYDLGEFNQKGTVRTKYGTRNQLQAAVTALKSNGIQV
SEQ ID NO: 11   (50)  GASQNDVGYGAYDLYDLGEFNQKGTVRTKYGTRSQLQAAVTSLKNNGIQV
SEQ ID NO: 12   (48)  GNSQADVGYGAYDLYDLGEFNQKGTVRTKYGTKAQLERAIGSLKSNDINV
SEQ ID NO: 13   (48)  GTSQADVGYGAYDLYDLGEFHQKGTVRTKYGTKGELQSAIKSLHSRDINV
SEQ ID NO: 14   (46)  AISQADVGYGAYDLYDLGEFHQKGTVRTKYGTKGELQSAIKSLHSRDINV 101                                            150
SEQ ID NO: 1    (98)  YGDVVINHKGGADATEDVTAVEVDPADRNRVISGEHLIKAWTHFHFPGRG
SEQ ID NO: 2    (99)  YADVVFDHKGGADGTEWVDAVEVNPSDRNQEISGTYQIQAWTKFDFPGRG
SEQ ID NO: 3    (101) YADVVFNHKAGADGTEFVDAVEVDPSNRNQETSGTYQIQAWTKFDFPGRG
SEQ ID NO: 4    (98)  YADVVFNHKAGADGTELVDAVEVNPSDRNQEISGTYQIQAWTKFDFPGRG
SEQ ID NO: 5    (100) YADVVFNHKAGADGTELVDAVEVNPSDRNQEISGTYQIQAWTKFDFPGRG
SEQ ID NO: 6    (96)  YGDVVLNHKAGADATEDVTAVEVNPANRNQETSEEYQIKAWTDFRFPGRG
SEQ ID NO: 7    (100) YGDVVMNHKGGADGTEIVNAVEVNRSNRNQETSGEYAIEAWTKFDFPGRG
SEQ ID NO: 8    (100) YGDVVMNHKGGADATENVLAVEVNPNNRNQEISGDYTIEAWTKFDFPGRG
SEQ ID NO: 9    (100) YGDVVMNHKGGADATEMVRAVEVNPNNRNQEVSGEYTIEAWTKFDFPGRG
SEQ ID NO: 10   (100) YGDVVMNHKGGADATEWVRAVEVNPSNRNQEVSGDYTIEAWTKFDFPGRG
SEQ ID NO: 11   (100) YGDVVMNHKGGADATEMVRAVEVNPNNRNQEVTGEYTIEAWTRFDFPGRG
SEQ ID NO: 12   (98)  YGDVVMNHKMGADFTEAVQAVQVNPTNRWQDISGAYTIDAWTGFDFSGRN
SEQ ID NO: 13   (98)  YGDVVINHKGGADATEDVTAVEVDPADRNRVISGEYLIKAWTHFHFPGRG
SEQ ID NO: 14   (96)  YGDVVINHKAGADATEDVTAVEVDPADRNRVISGEHLIKAWTHFHFPGRG
```

Fig. 1A

```
                    151                                         200
SEQ ID NO: 1  (148) STYSDFKWHWYHFDGTDWDESR-KLNRIYKFQG--KAWDWEVSNENGNYD
SEQ ID NO: 2  (149) NTYSSFKWRWYHFDGVDWDESR-KLSRIYKFRGIGKAWDWEVDTENGNYD
SEQ ID NO: 3  (151) NTYSSFKWRWYHFDGTDWDESR-KLNRIYKFRSTGKAWDWEVDTENGNYD
SEQ ID NO: 4  (148) NTYSSFKWRWYHFDGTDWDESR-KLNRIYKFRGTGKAWDWEVDTENGNYD
SEQ ID NO: 5  (150) NTYSSFKWRWYHFDGTDWDESR-KLNRIYKFRGTGKAWDWEVDTENGNYD
SEQ ID NO: 6  (146) NTYSDFKWHWYHFDGADWDESR-KISRIFKFRGEGKAWDWEVSSENGNYD
SEQ ID NO: 7  (150) NNHSSFKWRWYHFDGTDWDQSRQLQNKIYKFRGTGKAWDWEVDTENGNYD
SEQ ID NO: 8  (150) NTYSDFKWRWYHFDGVDWDQSRQFQNRIYKFRGDGKAWDWEVDSENGNYD
SEQ ID NO: 9  (150) NTHSNFKWRWYHFDGVDWDQSRKLNNRIYKFRGDGKGWDWEVDTENGNYD
SEQ ID NO: 10 (150) NTHSNFKWRWYHFDGVDWDQSRQLQNRIYKFRGDGKGWDWEVDTENGNYD
SEQ ID NO: 11 (150) NTHSSFKWRWYHFDGVDWDQSRRLNNRIYKFRGHGKAWDWEVDTENGNYD
SEQ ID NO: 12 (148) NAYSDFKWRWFHFNGVDWDQRY-QENHIFRFAN--TNWNWRVDEENGNYD
SEQ ID NO: 13 (148) STYSDFKWYWYHFDGTDWDESR-KLNRIYKFQG--KYWDWEVSNENGNYD
SEQ ID NO: 14 (146) STYSDFKWYWYHFDGTDWDESR-KLNRIYKFQG--KTWDWEVSNEFGNYD 201                                         250
SEQ ID NO: 1  (195) YLMYADIDYDHPDVAAEIKRWGTWYANELQLDGFRLDAVKHIKFSFLRDW
SEQ ID NO: 2  (198) YLMYADLDMDHPEVVTELKNWGKWYVNTTNIDGFRLDAVKHIKFSFFPDW
SEQ ID NO: 3  (200) YLMFADLDMDHPEVVTELKNWGTWYVNTTNIDGFRLDAVKHIKYSFFPDW
SEQ ID NO: 4  (197) YLMYADLDMDHPEVSELKNWGKWYVTTTNIDGFRLDAVKHIKYSFFPDW
SEQ ID NO: 5  (199) YLMYADLDMDHPEVSELKNWGKWYVITTNIDGFRLDAVKHIKYSFFPDW
SEQ ID NO: 6  (195) YLMYADVDYDHPDVVAETKKWGIWYANELSLDGFRIDAAKHIKFSFLRDW
SEQ ID NO: 7  (200) YLMYADVDMDHPEVIHELRNWGVWYTNTLNLDGFRIDAVKHIKYSFTRDW
SEQ ID NO: 8  (200) YLMYADVDMDHPEVNELRRWGEWYTNTLNLDGFRIDAVKHIKYSFTRDW
SEQ ID NO: 9  (200) YLMYADIDMDHPEVNELRNWGVWYTNTLGLDGFRIDAVKHIKYSFTRDW
SEQ ID NO: 10 (200) YLMYADIDMDHPEVNELRNWGVWYTNTLGLDGFRIDAVKHIKYSFTRDW
SEQ ID NO: 11 (200) YLMYADIDMDHPEVNELRNWGVWYTNTLGLDGFRIDAVKHIKYSFTRDW
SEQ ID NO: 12 (195) YLLGSNIDFSHPEVQDELKDWGSWFTDELDLDGYRLDAIKHIPFWYTSDW
SEQ ID NO: 13 (195) YLMYADIDYDHPDVVAEIKRWGTWYANELQLDGNRLDAVKHIKFSFLRDW
SEQ ID NO: 14 (193) YLMYADFDYDHPDVVAEIKRWGTWYANELQLDGFRLDAVKHIKFSFLRDW 251                                         300
SEQ ID NO: 1  (245) VNHVREKTGKEMFTVAEYWQNDLGALENYLNKTNFNHSVFDVPLHYQFHA
SEQ ID NO: 2  (248) LSYVRSQTGKPLFTVGEYWSYDINKLHNYITKTNGTMSLFDAPLHNKFYT
SEQ ID NO: 3  (250) LTYVRNQTGKNLFAVGEFWSYDVNKLHNYITKTNGSMSLFDAPLHNNFYT
SEQ ID NO: 4  (247) LSYVRTQTQKPLFAVGEFWSYDISKLHNYITKTNGSMSLFDAPLHNNFYI
SEQ ID NO: 5  (249) LSYLRTQTQKPLFAVGEFWSYDINKLHNYITKTNGSMSLFDAPLHNNFYI
SEQ ID NO: 6  (245) VQAVRQATGKEMFTVAEYWQNNAGKLENYLNKTSFNQSVFDVPLHFNLQA
SEQ ID NO: 7  (250) LTHVRNTTGKPMFAVAEFWKNDLGAIENYLNKTSWNHSVFDVPLHYNLYN
SEQ ID NO: 8  (250) LTHVRNATGKEMFAVAEFWKNDLGALENYLNKTNWNHSVFDVPLHYNLYN
SEQ ID NO: 9  (250) INHVRSATGKNMFAVAEFWKNDLGAIENYLNKTNWNHSVFDVPLHYNLYN
SEQ ID NO: 10 (250) LTHVRNTTGKNMFAVAEFWKNDIGAIENYLSKTNWNHSVFDVPLHYNLYN
SEQ ID NO: 11 (250) INHVRSATGKNMFAVAEFWKNDLGAIENYLQKTNWNHSVFDVPLHYNLYN
SEQ ID NO: 12 (245) VRHQRNEADQDLFVVGEYWKDDVGALEFYLDEMNWEMSLFDVPLNYNFYR
SEQ ID NO: 13 (245) VNHVREKTGKEMFTVAEYWQNDLGALENYLNKTNFNHSVFDVPLHYQFYA
SEQ ID NO: 14 (243) VNHVREKTGKEMFTVAEYWSNDLGALENYLNKTNFNHSVFDVPLHYQFHA
```

Fig. 1B

```
                         301                                              350
SEQ ID NO: 1  (295) ASTQGGGYDMRKLLNGTVVSKHPLKSVTFVDNHDTQPGQSLESTVQTWFK
SEQ ID NO: 2  (298) ASKSGGAFDMRTLMTNTLMKDQPTLAVTFVDNHDTEPGQALQSWVDPWFK
SEQ ID NO: 3  (300) ASKSSGYFDMRYLLNNTLMKDQPSLAVTLVDNHDTQPGQSLQSWVEPWFK
SEQ ID NO: 4  (297) ASKSGGYFDMRTLLNNTLMKDQPTLAVTLVDNHDTEPGQSLQSWVEPWFK
SEQ ID NO: 5  (299) ASKSGGYFDMRTLLNNTLMKEQPTLSVTLVDNHDTEPGQSLQSWVEPWFK
SEQ ID NO: 6  (295) ASSQGGGYDMRRLLDGTVVSRHPEKAVTFVENHDTQPGQSLESTVQTWFK
SEQ ID NO: 7  (300) ASNSGGYYDMRNILNGSVVQKHPTHAVTFVDNHDSQPGEALESFVQQWFK
SEQ ID NO: 8  (300) ASNSGGNYDMAKLLNGTVVQKHPMHAVTFVDNHDSQPGESLESFVQEWFK
SEQ ID NO: 9  (300) ASKSGGNYDMRQIFNGTVVQRHPMHAVTFVDNHDSQPEEALESFVEEWFK
SEQ ID NO: 10 (300) ASRSGGNYDMRQIFNGTVVQRHPTHAVTFVDNHDSQPEEALESFVEEWFK
SEQ ID NO: 11 (300) ASKSGGNYDMRNIFNGTVVQRHPSHAVTFVDNHDSQPEEALESFVEEWFK
SEQ ID NO: 12 (295) ASQQGGSYDMRNILRGSLVEAHPMHAVTFVDNHDTQPGESLESWVADWFK
SEQ ID NO: 13 (295) ASTQGGGYDMRKLLNDTVVSKHPLKSVTFVDNHDTQPGQSLESTVQTWFK
SEQ ID NO: 14 (293) ASTQGGGYDMRKLLNGTVVSKHPLKSVTFVDNHDTQPGQSLESTVQTWFK 351                                              400
SEQ ID NO: 1  (345) PLAYAFILTRESGYPQVFYGDMYGTKGDSQREIPALKHKIEPILKARKQY
SEQ ID NO: 2  (348) PLAYAFILTRQEGYPCVFYGDYYGIPQYN---IPSLKSIDPLLIARRDY
SEQ ID NO: 3  (350) PLAYAFILTRQEGYPCVFYGDYYGIPKYN---IPGLKSIDPLLIARRDY
SEQ ID NO: 4  (347) PLAYAFILTRQEGYPCVFYGDYYGIPKYN---IPALKSLDPLLIARRDY
SEQ ID NO: 5  (349) PLAYAFILTRQEGYPCVFYGDYYGIPKYN---IPALKSLDPLLIARRDY
SEQ ID NO: 6  (345) PLAYAFILTRESGYPQVFYGDMYGTKGTSPKEIPSLKDNIEPILKARKEY
SEQ ID NO: 7  (350) PLAYALVLTREQGYPSVFYGDYYGIPTHG---VPAMKSIDPLLQARQTF
SEQ ID NO: 8  (350) PLAYALILTREQGYPSVFYGDYYGIPTHS---VPAMKAKIDPILEARQNF
SEQ ID NO: 9  (350) PLAYALTLTREQGYPSVFYGDYYGIPTHG---VPAMKSIDPILEARQKY
SEQ ID NO: 10 (350) PLACALTLTRDQGYPSVFYGDYYGIPTHG---VPAMKSIDPILEARQKY
SEQ ID NO: 11 (350) PLAYALTLTREQGYPSVFYGDYYGIPTHG---VPAMRSKIDPILEARQKY
SEQ ID NO: 12 (345) PLAYATILTREGGYPNVFYGDYYGIPNDN---ISAKKDMIDELLDARQNY
SEQ ID NO: 13 (345) PLAYAFILTRESGYPQVFYGDMYGTKGDSQREIPALKHKIEPILKARKQY
SEQ ID NO: 14 (343) PLAYAFILTRESGYPQVFYGDMYGTKGDSQREIPALKHKIEPILKARKQY 401                                              450
SEQ ID NO: 1  (395) AYGAQHDYFDHHDIVGWTREGDSSVANSGLAALITDGPGGAKRMYVGRQN
SEQ ID NO: 2  (395) AYGTQHDYLDHSDIIGWTREGVTEKPGSGLAALITDGPGGSKWMYVGKQH
SEQ ID NO: 3  (397) AYGTQRDYIDHQDIIGWTREGIDTKPNSGLAALITDGPGGSKWMYVGKKH
SEQ ID NO: 4  (394) AYGTQHDYIDSADIIGWTREGVAEKANSGLAALITDGPGGSKWMYVGKQH
SEQ ID NO: 5  (396) AYGTQHDYIDNADIIGWTREGVAEKANSGLAALITDGPGGSKWMYVGKQH
SEQ ID NO: 6  (395) AYGPQHDYIDPDVIGWTREGDSSAAKSGLAALITDGPGGSKRMYAGLKN
SEQ ID NO: 7  (397) AYGTQHDYFDHHDIIGWTREGNSSHPNSGLATIMSDGPGGNKWMYVGKNK
SEQ ID NO: 8  (397) AYGTQHDYFDHHNIIGWTREGNTTHPNSGLATIMSDGPGGEKWMYVGQNK
SEQ ID NO: 9  (397) AYGRQNDYLDHHNIIGWTREGNTAHPNSGLATIMSDGAGGNKWMFVGRNK
SEQ ID NO: 10 (397) AYGKQNDYLDHHNMIGWTREGNTAHPNSGLATIMSDGPGGNKWMYVGRNK
SEQ ID NO: 11 (397) AYGKQNDYLDHHNIIGWTREGNTAHPNSGLATIMSDGAGGSKWMFVGRNK
SEQ ID NO: 12 (392) AYGTQHDYFDHWDVVGWTREGSSSRPNSGLATIMSNGPGGSKWMYVGRQN
SEQ ID NO: 13 (395) AYGAQHDYFDHHDIVGWTREGDSSVANSGLAALITDGPGGAKRMYVGRQN
SEQ ID NO: 14 (393) AYGAQHDYFDHHDIVGWTREGDSSVANSGLAALITDGPGGAKRMYVGRQN
```

Fig. 1C

```
                    451                                           500
SEQ ID NO: 1   (445) AGETWHDITGNRSEPVVINSEGWGEFHVNGGSVSIYVQR-----------
SEQ ID NO: 2   (445) AGKVFYDLTGNRSDTVTINSDGWGEFKVNGGSVSVWVPRKTT---VSTIA
SEQ ID NO: 3   (447) AGKVFYDLTGNRSDTVTINADGWGEFKVNGGSVSIWVAKTSN---VTFTV
SEQ ID NO: 4   (444) AGKTFYDLTGNRSDTVTINADGWGEFKVNGGSVSIWVPKISTTSQITFTV
SEQ ID NO: 5   (446) AGKTFYDLTGNRSDTVTINADGWGEFKVNGGSVSIWVPKTSTTSQITFTV
SEQ ID NO: 6   (445) AGETWYDITGNRSDTVKIGSDGWGEFHVNDGSVSIYVQK-----------
SEQ ID NO: 7   (447) AGQVWRDITGNRTGTVTINADGWGNFSVNGGSVSVWVKQ-----------
SEQ ID NO: 8   (447) AGQVWHDITGNKPGTVTINADGWANFSVNGGSVSIWVKR-----------
SEQ ID NO: 9   (447) AGQVWTDITGNRAGTVTINADGWGNFSVNGGSVSIWVNK-----------
SEQ ID NO: 10  (447) AGQVWRDITGNRSGTVTINADGWGNFSVNGGSVSIWVNN-----------
SEQ ID NO: 11  (447) AGQVWSDITGNRTGTVTINADGWANFSVNGGSVSIWVNK-----------
SEQ ID NO: 12  (442) AGQTWDLTGNNGASVTINGDGWGEFFTNGGSVSVYVNQ-----------
SEQ ID NO: 13  (445) AGETWYDITGNRSEPVVINSEGWGEFHVNDGSVSIYVQR-----------
SEQ ID NO: 14  (443) AGETWHDITGNRSEPVVINSEGWGEFHVNGGSVSIYVQR-----------

501                                           550
SEQ ID NO: 1   (484) --------------------------------------------------
SEQ ID NO: 2   (492) RPITTRPWTGEFVRWTEPRLVAWP--------------------------
SEQ ID NO: 3   (494) NNATTTSGQNVYVVANIPELGNWNTANAIKMNPSSYPTWKATIALPQGKA
SEQ ID NO: 4   (494) NNATTVWGQNVYVVGNISQLGNWDPVHAVQMTPSSYPTWTVTIPLLQGQN
SEQ ID NO: 5   (496) NNATTVWGQNVYVVGNISQLGNWDPVNAVQMTPSSYPTWVVTVPLPQSQN
SEQ ID NO: 6   (484) --------------------------------------------------
SEQ ID NO: 7   (486) --------------------------------------------------
SEQ ID NO: 8   (486) --------------------------------------------------
SEQ ID NO: 9   (486) --------------------------------------------------
SEQ ID NO: 10  (486) --------------------------------------------------
SEQ ID NO: 11  (486) --------------------------------------------------
SEQ ID NO: 12  (481) --------------------------------------------------
SEQ ID NO: 13  (484) --------------------------------------------------
SEQ ID NO: 14  (482) --------------------------------------------------

551                                    591
SEQ ID NO: 1   (484) -----------------------------------------
SEQ ID NO: 2   (516) -----------------------------------------
SEQ ID NO: 3   (544) IEFKFIKKDQAGNVIWESTSNRTYTVPFSSTGSYTASWNVP
SEQ ID NO: 4   (544) IQFKFIKKDSAGNVIWEDISNRTYTVPTAASGAYTASWNVP
SEQ ID NO: 5   (546) IQFKFIKKDGSGNVIWENISNRTYTVPTAASGAYTANWNVP
SEQ ID NO: 6   (484) -----------------------------------------
SEQ ID NO: 7   (486) -----------------------------------------
SEQ ID NO: 8   (486) -----------------------------------------
SEQ ID NO: 9   (486) -----------------------------------------
SEQ ID NO: 10  (486) -----------------------------------------
SEQ ID NO: 11  (486) -----------------------------------------
SEQ ID NO: 12  (481) -----------------------------------------
SEQ ID NO: 13  (484) -----------------------------------------
SEQ ID NO: 14  (482) -----------------------------------------
```

Fig. 1D

ALPHA-AMYLASE VARIANTS AND POLYNUCLEOTIDES ENCODING SAME

CROSS-REFERENCE TO RELATED APPLICATIONS

This application is a divisional of U.S. application Ser. No. 16/425,184 filed on May 29, 2019, now pending, which is a divisional of U.S. application Ser. No. 15/062,644 filed on Mar. 7, 2016, now U.S. patent Ser. No. 10/351,836, which is a continuation of U.S. application Ser. No. 14/346,107 filed on Mar. 20, 2014, now abandoned, which is a 35 U.S.C. 371 national application of international application no. PCT/EP2012/070578 filed on Oct. 17, 2012, which claims priority or the benefit under 35 U.S.C. 119 of European application no. 11185479.0 filed Oct. 17, 2011 and U.S. provisional application No. 61/548,416 filed Oct. 18, 2011. The content of each application is fully incorporated herein by reference.

REFERENCE TO A SEQUENCE LISTING

This application contains a Sequence Listing in computer readable form, which is incorporated herein by reference. The name of the file containing the Sequence Listing is SQ.txt, which was created on Mar. 20, 2020 and has 125 KB.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (E.C. 3.2.1.1) constitute a group of enzymes which catalyze hydrolysis of starch, glycogen and related polysaccharides and oligosaccharides.

Alpha-amylases are used commercially for a variety of purposes such as in the initial stages of starch processing (e.g., liquefaction); in wet milling processes; and in alcohol production from carbohydrate sources. They are also used as cleaning agents or adjuncts in detergent matrices; in the textile industry for starch desizing; in baking applications; in the beverage industry; in oil fields in drilling processes; in recycling processes, e.g., for de-inking paper; and in animal feed.

Some commercial alpha-amylases for, e.g., starch liquefaction originate from *Bacillus licheniformis* or *Bacillus stearothermophilus*. Protein engineered variants of wild type enzymes have been developed to overcome process issues. There is still a need, though, for novel alpha-amylases with improved properties, such as higher stability at low pH, low calcium and high temperature. Such enzymes will allow the starch liquefaction process to be run at reduced pH which has a positive influence on chemical savings.

It is an object of the present invention to provide novel alpha-amylase variants having an increased stability at low pH and/or at high temperature, in particular at low calcium concentrations.

SUMMARY OF THE INVENTION

The present inventors have found that alpha-amylase variants comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1 have an increased stability when incubated at low pH and/or at high temperature, in particular at low calcium concentrations, and in particular in the presence of at least 0.1% starch, e.g., in the presence of 0.9% or 1% starch.

The present invention therefore relates to alpha-amylase variants comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1, wherein the variant has at least 60% and less than 100% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14, and wherein the variant has alpha-amylase activity.

The present invention also relates to isolated polynucleotides encoding the variants; nucleic acid constructs, vectors, and host cells comprising the polynucleotides; and methods of producing the variants.

The present invention also relates to uses of the variants of the invention and to a method of producing liquefied starch and a method of producing a fermentation product.

BRIEF DESCRIPTION OF THE FIGURES

FIGS. 1A, 1B, 1C and 1D show an alignment of alpha-amylases with the amino acid sequences of:

SEQ ID NO: 1 is a *Bacillus licheniformis* alpha-amylase.

SEQ ID NO: 2 is a *Bacillus stearothermophilus* alpha-amylase.

SEQ ID NO: 3 is the *Bacillus* alpha-amylase TS-23 described in J. Appl. Microbiology, 1997, 82: 325-334 (SWALL:q59222).

SEQ ID NO: 4 is *Bacillus* flavothermus alpha-amylase AMY1048 described in WO 2005/001064.

SEQ ID NO: 5 is *Bacillus* alpha-amylase TS-22 described as SEQ ID NO: 21 in WO 2004/113511.

SEQ ID NO: 6 is a *Bacillus amyloliquefaciens* alpha-amylase.

SEQ ID NO: 7 is *Bacillus* alkaline sp. SP690 amylase described as SEQ ID NO: 1 in WO 95/26397.

SEQ ID NO: 8 is *Bacillus halmapalus* alpha-amylase described as SEQ ID NO: 2 in WO 95/26397.

SEQ ID NO: 9 is *Bacillus* alkaline sp. AA560 amylase described as SEQ ID NO: 4 in WO 00/60060.

SEQ ID NO: 10 is *Bacillus* alkaline sp. A 7-7 amylase described as SEQ ID NO: 2 in WO 02/10356.

SEQ ID NO: 11 is *Bacillus* alkaline sp. SP707 amylase described in Tsukamoto et al., 1988, Biochem. Biophys. Res. Commun. 151: 25-33).

SEQ ID NO: 12 is *Bacillus* alkaline sp. K-38 amylase described as SEQ ID NO: 2 in EP 1022334.

SEQ ID NO: 13 is a *Bacillus licheniformis* alpha-amylase described in Lee et al, 2006, J. Biochem., 139: 997-1005.

SEQ ID NO: 14 is a variant alpha-amylase LE399 previously disclosed in, e.g., WO 02/010355.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylase: Alpha-amylases (E.C. 3.2.1.1) are a group of enzymes which catalyze the hydrolysis of starch and other linear and branched 1,4 glucosidic oligo- and polysaccharides. The skilled person will know how to determine alpha-amylase activity. It may be determined according to the procedure described in the Examples, e.g., by the PNP-G7 assay. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1. In another aspect, a variant of the present application has at least 20%, e.g., at least 40%, at least 50%, at least 60%, at least 70%, at least 80%, at least 90%, at least 95%, or at least 100% of the alpha-amylase activity of its parent.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity. In one aspect, a fragment contains at least 300 amino acid residues, at least 350 amino acid residues, at least 400 amino acid residues, at least 450 amino acid residues, at least 470 amino acid residues, or at least 480 amino acid residues.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two or more different mature polypeptides (i.e., with a different C-terminal and/or N-terminal amino acid) expressed by the same polynucleotide. The mature form of some alpha-amylases, e.g., some bacterial alpha-amylases, comprises a catalytic domain containing the active site for substrate hydrolysis and one or more carbohydrate-binding modules (CBM) for binding to the carbohydrate substrate (starch) and optionally a polypeptide linking the CBM(s) with the catalytic domain, a region of the latter type usually being denoted a "linker".

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means an alpha-amylase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to the amino acid occupying a position. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1. In another aspect, a variant of the present application has at least 20%, e.g., at least 40%, at least 50%, at least 60%, at least 70%, at least 80%, at least 90%, at least 95%, or at least 100% of the alpha-amylase activity of its parent. The alpha-amylase activity may be determined by the PNP-G7 assay described in the Examples.

Wild-type alpha-amylase: The term "wild-type" alpha-amylase means an alpha-amylase expressed by a naturally occurring microorganism, such as a bacterium, yeast, or filamentous fungus found in nature.

Conventions for Designation of Variants

For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later); Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. In the Examples of the present application, multiple mutations are separated by a space, e.g., G205R S411F representing G205R+S411F.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to alpha-amylase variants comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1, wherein the variant has at least 60% and less than 100% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14, and wherein the variant has alpha-amylase activity.

Preferably, the variants are isolated.

Variants

A variant of the invention comprises an alteration at one or more (several) positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1.

In one embodiment, the variant comprises an insertion or a substitution at a position corresponding to position 1 with Arg, Asn, Asp, Cys, Gin, Glu, Gly, His, Ile, Leu, Lys, Met, Phe, Pro, Ser, Thr, Trp, Tyr or Val, in particular an insertion of or a substitution with Phe, His, Tyr or Trp, preferably His or Trp.

In one embodiment, the variant comprises an insertion or a substitution at a position corresponding to position 2 with Ala, Arg, Asp, Cys, Gin, Glu, Gly, His, Ile, Leu, Lys, Met, Phe, Pro, Ser, Thr, Trp, Tyr or Val, in particular an insertion of or a substitution with Phe, His, Tyr or Trp, preferably His or Trp.

In one embodiment, the variant comprises a substitution at a position corresponding to position 68 with Ala, Arg, Asn, Asp, Cys, Gin, Glu, Gly, Ile, Leu, Lys, Met, Phe, Pro, Ser, Thr, Trp, Tyr or Val, in particular with Phe, Tyr or Trp, preferably with Trp.

In one embodiment, the variant comprises a substitution at a position corresponding to position 71 with Ala, Arg, Asn, Asp, Cys, Gin, Glu, His, Ile, Leu, Lys, Met, Phe, Pro, Ser, Thr, Trp, Tyr or Val, in particular with Phe, His, Tyr or Trp, preferably with Trp.

In one embodiment, the variant comprises a substitution at a position corresponding to position 126 with Ala, Arg, Asp, Cys, Gin, Glu, Gly, His, Ile, Leu, Lys, Met, Phe, Pro, Ser, Thr, Trp, Tyr or Val, in particular with Phe, His, Tyr or Trp, preferably with Trp.

In one embodiment, the variant comprises a substitution at a position corresponding to position 133 with Ala, Arg, Asn, Asp, Cys, Gin, Glu, Gly, Ile, Leu, Met, Phe, Pro, Ser, Thr, Trp, Tyr or Val, in particular with Phe, Tyr or Trp, preferably with Tyr.

In one embodiment, the variant comprises a substitution at a position corresponding to position 142 with Ala, Arg, Asn, Asp, Cys, Gin, Glu, Gly, Ile, Leu, Lys, Met, Phe, Pro, Ser, Thr, Trp, Tyr or Val, in particular with Phe, Tyr or Trp, preferably with Trp.

In one embodiment, the variant comprises a substitution at a position corresponding to position 144 with Ala, Arg, Asn, Asp, Cys, Gin, Glu, Gly, His, Ile, Leu, Lys, Met, Phe, Ser, Thr, Trp, Tyr or Val, in particular with Phe, His, Tyr or Trp, preferably with Trp.

In one embodiment, the variant comprises a substitution at a position corresponding to position 156 with Ala, Arg, Asn, Asp, Cys, Gin, Glu, Gly, His, Ile, Leu, Lys, Met, Phe, Pro, Ser, Thr, Trp or Val, in particular with Phe, His or Trp, preferably with Trp.

In one embodiment, the variant comprises a substitution at a position corresponding to position 158 with Ala, Arg, Asn, Asp, Cys, Gin, Glu, Gly, His, Ile, Leu, Lys, Met, Phe, Pro, Ser, Thr, Trp, Tyr or Val, in particular with Phe, His or Trp, preferably with Trp.

In one embodiment, the variant comprises a substitution at a position corresponding to position 176 with Ala, Arg, Asn, Asp, Cys, Gin, Glu, Gly, His, Ile, Leu, Met, Phe, Pro, Ser, Thr, Trp, Tyr or Val, in particular with Leu.

In one embodiment, the variant comprises a substitution at a position corresponding to position 185 with Ala, Arg, Asn, Asp, Cys, Gin, Gly, His, Ile, Leu, Lys, Met, Phe, Ser, Thr, Trp, Tyr or Val, in particular with Pro.

In one embodiment, the variant comprises a substitution at a position corresponding to position 201 with Ala, Arg, Asn, Asp, Cys, Gin, Glu, Gly, His, Leu, Lys, Met, Phe, Pro, Ser, Thr, Trp, Tyr or Val, in particular with Tyr.

In one embodiment, the variant comprises a substitution at a position corresponding to position 205 with Ala, Arg, Asn, Asp, Cys, Gin, Glu, Gly, Ile, Leu, Lys, Met, Phe, Pro, Ser, Thr, Trp, Tyr or Val, in particular with Tyr.

In one embodiment, the variant comprises a substitution at a position corresponding to position 213 with Ala, Arg, Asn, Asp, Cys, Gin, Glu, Gly, His, Ile, Leu, Met, Phe, Pro, Ser, Thr, Trp, Tyr or Val, in particular with Thr.

In one embodiment, the variant comprises a substitution at a position corresponding to position 239 with Ala, Arg, Asn, Asp, Cys, Gin, Glu, Gly, His, Ile, Leu, Lys, Met, Phe, Pro, Thr, Trp, Tyr or Val, in particular with Ala or Gin.

In one embodiment, the variant comprises a substitution at a position corresponding to position 279 with Ala, Arg, Asn, Asp, Cys, Gin, Glu, Gly, His, Ile, Leu, Lys, Met, Pro, Ser, Thr, Trp, Tyr or Val, in particular with His, Tyr or Trp, preferably with Trp.

In one embodiment, the variant comprises a substitution at a position corresponding to position 316 with Ala, Arg, Asn, Asp, Cys, Gin, Glu, Gly, Ile, Leu, Lys, Met, Phe, Pro, Ser, Thr, Trp, Tyr or Val, in particular with Phe, Tyr or Trp, preferably with Trp.

In one embodiment, the variant comprises a substitution at a position corresponding to position 318 with Ala, Arg, Asn, Asp, Cys, Gin, Glu, Gly, His, Ile, Lys, Met, Phe, Pro, Ser, Thr, Trp, Tyr or Val, in particular with Phe, His, Tyr or Trp, preferably with Trp.

In one embodiment, the variant comprises a substitution at a position corresponding to position 360 with Ala, Arg, Asn, Asp, Cys, Glu, Gly, His, Ile, Leu, Lys, Met, Phe, Pro, Ser, Thr, Trp, Tyr or Val, in particular with Ser.

In one embodiment, the variant comprises a substitution at a position corresponding to position 416 with Ala, Arg, Asp, Cys, Gin, Glu, Gly, His, Ile, Leu, Lys, Met, Phe, Pro, Ser, Thr, Trp, Tyr or Val, in particular with Val.

In one embodiment, the variant comprises a substitution at a position corresponding to position 437 with Ala, Asn, Asp, Cys, Gin, Glu, Gly, His, Ile, Leu, Lys, Met, Phe, Pro, Ser, Thr, Trp, Tyr or Val, in particular with Phe, His, Tyr or Trp, preferably with Trp.

In one embodiment, the variant comprises a substitution at a position corresponding to position 450 with Ala, Arg, Asn, Asp, Cys, Gln, Glu, Gly, Ile, Leu, Lys, Met, Phe, Pro, Ser, Thr, Trp, Tyr or Val, in particular with Phe, Tyr or Trp, preferably with Trp.

The variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14.

In a preferred embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 1, or (ii) amino acids 1-483 of SEQ ID NO: 1.

In one embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 2, (ii) the mature polypeptide of SEQ ID NO: 2 comprising the deletions I181*+G182*, (iii) amino acids 1-483 of SEQ ID NO: 2, or (iv) amino acids 1-483 of SEQ ID NO: 2 comprising the deletions I181*+G182*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 3, (ii) the mature polypeptide of SEQ ID NO: 3 comprising the deletions T183*+G184*, (iii) amino acids 1-485 of SEQ ID NO: 3, or (iv) amino acids 1-485 of SEQ ID NO: 3 comprising the deletions T183*+G184*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 4, (ii) the mature polypeptide of SEQ ID NO: 4 comprising the deletions T180*+G181*, (iii) amino acids 1-482 of SEQ ID NO: 4, or (iv) amino acids 1-482 of SEQ ID NO: 4 comprising the deletions T180*+G181*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 5, (ii) the mature polypeptide of SEQ ID NO: 5 comprising the deletions T182*+G183*, (iii) amino acids 1-484 of SEQ ID NO: 5, or (iv) amino acids 1-484 of SEQ ID NO: 5 comprising the deletions T182*+G183*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 6, (ii) the mature polypeptide of SEQ ID NO: 6 comprising the deletions E178*+G179*, (iii) amino acids 1-483 of SEQ ID NO: 6, or (iv) amino acids 1-483 of SEQ ID NO: 6 comprising the deletions E178*+G179*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 7, (ii) the mature polypeptide of SEQ ID NO: 7 comprising the deletions T183*+G184*, (iii) amino acids 1-485 of SEQ ID NO: 7, or (iv) amino acids 1-485 of SEQ ID NO: 7 comprising the deletions T183*+G184*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 8, (ii) the mature polypeptide of SEQ ID NO: 8 comprising the deletions D183*+G184*, (iii) amino acids 1-485 of SEQ ID NO: 8, or (iv) amino acids 1-485 of SEQ ID NO: 8 comprising the deletions D183*+G184*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 9, (ii) the mature polypeptide of SEQ ID NO: 9 comprising the deletions D183*+G184*, (iii) amino acids 1-485 of SEQ ID NO: 9, or (iv) amino acids 1-485 of SEQ ID NO: 9 comprising the deletions D183*+G184*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 10, (ii) the mature polypeptide of SEQ ID NO: 10 comprising the deletions D183*+G184*, (iii) amino acids 1-485 of SEQ ID NO: 10, or (iv) amino acids 1-485 of SEQ ID NO: 10 comprising the deletions D183*+G184*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 11, (ii) the mature polypeptide of SEQ ID NO: 11 comprising the deletions H183*+G184*, (iii) amino acids 1-485 of SEQ ID NO: 11, or (iv) amino acids 1-485 of SEQ ID NO: 11 comprising the deletions H183*+G184*.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 12, or (ii) amino acids 1-480 of SEQ ID NO: 12.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 13, or (ii) amino acids 1-483 of SEQ ID NO: 13.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 14, or (ii) amino acids 1-483 of SEQ ID NO: 14.

A variant of the invention comprises an alteration at one or more (e.g., several) positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1. In one embodiment, the variant comprises an alteration at one position corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at two positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at three positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at four positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at more than four, e.g., five, six, seven, eight, nine or ten, positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at more than 10 positions, e.g., 11, 12, 13, 14, 15, 16, 17, 18, 19 or 20 positions, corresponding to any of positions 1, 2, 68, 71, 126, 133, 142, 144, 156, 158, 176, 185, 201, 205, 213, 239, 279, 316, 318, 360, 416, 437 and 450.

In an embodiment, the variant comprises an alteration at two or more positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at three or more positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at four or more positions corresponding to any of positions 1, 2, 68, 71, 126, 133, 142, 144, 156, 158, 176, 185, 201, 205, 213, 239, 279, 316, 318, 360, 416, 437 and 450. In another embodiment, the variant comprises an alteration at five or more positions corresponding to any of positions 1, 2, 68, 71, 126, 133, 142, 144, 156, 158, 176, 185, 201, 205, 213, 239, 279, 316, 318, 360, 416, 437 and 450.

In a preferred embodiment, the variant comprises an alteration at two or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises an alteration at two or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In another preferred embodiment, the variant comprises an alteration at three or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises an alteration at three or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In another preferred embodiment, the variant comprises an alteration at four or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises an alteration at four or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In another preferred embodiment, the variant comprises an alteration at five or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises an alteration at five or more positions corresponding to any of positions 1, 2, 68, 71, 126, 133, 142, 144, 156, 158, 176, 185, 201, 205, 213, 239, 279, 316, 318, 360, 416, 437 and 450, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant of the invention comprises one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W.

In a preferred embodiment, the variant of the invention comprises one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In another preferred embodiment, the variant comprises two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In another embodiment, the variant comprises three or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W. In another embodiment, the variant comprises four or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises an alteration at one or more positions corresponding to any of positions 2, 68, 133, 142, 156, 158, 176, 185, 201, 205, 213, 279, 360, 416 and 437. In another preferred embodiment, the variant comprises an alteration at two or more positions corresponding to any of positions 2, 68, 133, 142, 156, 158, 176, 185, 201, 205, 213, 279, 360, 416 and 437. In another preferred embodiment, the variant comprises an alteration at three or more positions corresponding to any of positions 2, 68, 133, 142, 156, 158, 176, 185, 201, 205, 213, 279, 360, 416 and 437. In another preferred embodiment, the variant comprises an alteration at four or more positions corresponding to any of positions 2, 68, 133, 142, 156, 158, 176, 185, 201, 205, 213, 279, 360, 416 and 437. In another preferred embodiment, the variant comprises an alteration at five or more positions corresponding to any of positions 2, 68, 133, 142, 156, 158, 176, 185, 201, 205, 213, 279, 360, 416 and 437. In another preferred embodiment, the variant comprises an alteration at six or more positions corresponding to any of positions 2, 68, 133, 142, 156, 158, 176, 185, 201, 205, 213, 279, 360, 416 and 437.

In a preferred embodiment, the variant comprises one or more substitutions selected from the group consisting of N2H, H68W, H133Y, H142W, Y156W, Y158W, K176L, E185P, I201Y, H205Y, K213T, F279W, Q360S, D416V and R437W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises two or more substitutions selected from the group consisting of N2H, H68W, H133Y, H142W, Y156W, Y158W, K176L, E185P, I201Y, H205Y, K213T, F279W, Q360S, D416V and R437W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises three or more substitutions selected from the group consisting of N2H, H68W, H133Y, H142W, Y156W, Y158W, K176L, E185P, I201Y, H205Y, K213T, F279W, Q360S, D416V and R437W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises four or more substitutions selected from the group consisting of N2H, H68W, H133Y, H142W, Y156W, Y158W, K176L, E185P, I201Y, H205Y, K213T, F279W, Q360S, D416V and R437W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In one embodiment, the variant comprises an insertion or a substitution at a position corresponding to position 1, in particular the insertion A1AH or A1AW or the substitution A1H or A1W, in combination with an alteration at one or more positions corresponding to any of positions 2, 68, 71, 126, 133, 142, 144, 156, 158, 176, 185, 201, 205, 213, 239, 279, 316, 318, 360, 416, 437 and 450, in particular one or more alterations selected from the group consisting of N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises an insertion or a substitution at a position corresponding to position 1, in particular the insertion A1AH or A1AW or the substitution A1H or A1W, in combination with an alteration at one or more positions corresponding to any of positions 2, 68, 71, 126, 133, 142, 144, 156, 158, 176, 185, 201, 205, 213, 239, 279, 316, 318, 360, 416, 437 and 450, in particular one or more alterations selected from the group consisting of N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises an insertion or a substitution at a position corresponding to position 1, in particular the insertion A1AH or A1AW or the substitution A1H or A1W, in combination with an alteration at one or more positions corresponding to any of positions 2, 68, 71, 126, 133, 142, 144, 156, 158, 176, 185, 201, 205, 213, 239, 279, 316, 318, 360, 416, 437 and 450, in particular one or more alterations selected from the group consisting of N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises an insertion or a substitution at a position corresponding to position 2, in particular the insertion N2NH or N2NW or the substitution N2H or N2W, in combination with an alteration at one or more positions corresponding to any of positions 1, 68, 71, 126, 133, 142, 144, 156, 158, 176, 185, 201, 205, 213, 239, 279, 316, 318, 360, 416, 437 and 450, in particular one or more alterations selected from the group consisting of A1AH, A1AW, A1H, A1W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises an insertion or a substitution at a position corresponding to position 2, in particular the insertion N2NH or N2NW or the substitution N2H or N2W, in combination with an alteration at one or more positions corresponding to any of positions 1, 68, 71, 126, 133, 142, 144, 156, 158, 176, 185, 201, 205, 213, 239, 279, 316, 318, 360, 416, 437 and 450, in particular one or more alterations selected from the group consisting of A1AH, A1AW, A1H, A1W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises an insertion or a substitution at a position corresponding to position 2, in particular the insertion N2NH or N2NW or the substitution N2H or N2W, in combination with an alteration at one or more positions corresponding to any of positions 1, 68, 71, 126, 133, 142, 144, 156, 158, 176, 185, 201, 205, 213, 239, 279, 316, 318, 360, 416, 437 and 450, in particular one or more alterations selected from the group consisting of A1AH, A1AW, A1H, A1W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 68, in particular the substitution H68W, in combination with a substitution at one or more positions corresponding to any of positions 1, 2, 71, 126, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 68, in particular the substitution H68W, in combination with a substitution at one or more positions corresponding to any of positions 1, 2, 71, 126, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 68, in particular the substitution H68W, in combination with a substitution at one or more positions corresponding to any of positions 1, 2, 71, 126, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 71, in particular the substitution G71W, in combination with a substitution at one or more positions corresponding to any of positions 1, 2, 68, 126, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 71, in particular the substitution G71W, in combination with a substitution at one or more positions corresponding to any of positions 1, 2, 68, 126, 133, 142, 144, 156, 158, 176, 185, 201, 205, 213, 239, 279, 316, 318, 360, 416, 437 and 450, in particular one or more substitutions selected from the group consisting of A1H, A1 W, N2H, N2W, H68W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 71, in particular the substitution G71W, in combination with a substitution at one or more positions corresponding to any of positions 1, 2, 68, 126, 133, 142, 144, 156, 158, 176, 185, 201, 205, 213, 239, 279, 316, 318, 360, 416, 437 and 450, in particular one or more substitutions selected from the group consisting of A1H, A1 W, N2H, N2W, H68W, N126W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 126, in particular the substitution N126W, in combination with a substitution at one or more positions corresponding to any of positions 1, 2, 68, 71, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, H133Y, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 126, in particular the substitution N126W, in combination with a substitution at one or more positions corresponding to any of positions 1, 2, 68, 71, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 126, in particular the substitution N126W, in combination with a substitution at one or more positions corresponding to any of positions 1, 2, 68, 71, 133, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, H133Y, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 133, in particular the substitution H133Y, in combination with a substitution at one or more positions corresponding to any of positions 1, 2, 68, 71, 126, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H142W, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 133, in particular the substitution H133Y, in combination with a substitution at one or more positions corresponding to any of positions 1, 2, 68, 71, 126, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 133, in particular the substitution H133Y, in combination with a substitution at one or more positions corresponding to any of positions 1, 2, 68, 71, 126, 142, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H142W, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 142, in particular the substitution H142W, in combination with a substitution at one or more positions corresponding to any of positions 1, 2, 68, 71, 126, 133, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, P144W, Y156W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 142, in particular the substitution H142W, in combination with a substitution at one or more positions corresponding to any of positions 1, 2, 68, 71, 126, 133, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 142, in particular the substitution H142W, in combination with a substitution at one or more positions corresponding to any of positions 1, 2, 68, 71, 126, 133, 144, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, P144W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 144, in particular the substitution P144W, in combination with a substitution at one or more positions corresponding to any of positions 1, 2, 68, 71, 126, 133, 142, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, Y156W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 144, in particular the substitution P144W, in combination with a substitution at one or more positions corresponding to any of positions 1, 2, 68, 71, 126, 133, 142, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 144, in particular the substitution P144W, in combination with a substitution at one or more positions corresponding to any of positions 1, 2, 68, 71, 126, 133, 142, 156, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, Y156W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 156, in particular the substitution Y156W, in combination with a substitution at one or more positions corresponding to any of positions 1, 2, 68, 71, 126, 133, 142, 144, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y158W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 156, in particular the substitution Y156W, in combination with a substitution at one or more positions corresponding to any of positions 1, 2, 68, 71, 126, 133, 142, 144, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 156, in particular the substitution Y156W, in combination with a substitution at one or more positions corresponding to any of positions 1, 2, 68, 71, 126, 133, 142, 144, 158, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y158W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 158, in particular the substitution Y158W, in combination with a substitution at one or more positions corresponding to any of positions 1, 2, 68, 71, 126, 133, 142, 144, 156, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, K176L, E185P, I201Y, H205Y, K213T, S239A, S239Q, F279W, H316W, L318W, Q360S, D416V, R437W and H450W.

In a preferred embodiment, the variant comprises a substitution at a position corresponding to position 158, in particular the substitution Y158W, in combination with a substitution at one or more positions corresponding to any of positions 1, 2, 68, 71, 126, 133, 142, 144, 156, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 158, in particular the substitution Y158W, in combination with a substitution at one or more positions corresponding to any of positions 1, 2, 68, 71, 126, 133, 142, 144, 156, 176, 185, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, K176L, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W.

In a preferred embodiment, the variant comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 185, in particular the substitution E185P, in combination with a substitution at one or more positions corresponding to any of positions 1, 2, 68, 71, 126, 133, 142, 144, 156, 158, 176, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W.

In a preferred embodiment, the variant comprises a substitution at a position corresponding to position 185, in particular the substitution E185P, in combination with a substitution at one or more positions corresponding to any of positions 1, 2, 68, 71, 126, 133, 142, 144, 156, 158, 176, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 185, in particular the substitution E185P, in combination with a substitution at one or more positions corresponding to any of positions 1, 2, 68, 71, 126, 133, 142, 144, 156, 158, 176, 201, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 201, in particular the substitution I201Y, in combination with a substitution at one or more positions corresponding to any of positions 1, 2, 68, 71, 126, 133, 142, 144, 156, 158, 176, 185, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V, R437W and H450W.

In a preferred embodiment, the variant comprises a substitution at a position corresponding to position 201, in particular the substitution I201Y, in combination with a substitution at one or more positions corresponding to any of positions 1, 2, 68, 71, 126, 133, 142, 144, 156, 158, 176, 185, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 201, in particular the substitution I201Y, in combination with a substitution at one or more positions corresponding to any of positions 1, 2, 68, 71, 126, 133, 142, 144, 156, 158, 176, 185, 205, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 205, in particular the substitution H205Y, in combination with a substitution at one or more positions corresponding to any of positions 1, 2, 68, 71, 126, 133, 142, 144, 156, 158, 176, 185, 201, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V, R437W and H450W.

In a preferred embodiment, the variant comprises a substitution at a position corresponding to position 205, in particular the substitution H205Y, in combination with a substitution at one or more positions corresponding to any of positions 1, 2, 68, 71, 126, 133, 142, 144, 156, 158, 176, 185, 201, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 205, in particular the substitution H205Y, in combination with a substitution at one or more positions corresponding to any of positions 1, 2, 68, 71, 126, 133, 142, 144, 156, 158, 176, 185, 201, 213, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 213, in particular the substitution K213T, in combination with a substitution at one or more positions corresponding to any of positions 1, 2, 68, 71, 126, 133, 142, 144, 156, 158, 176, 185, 201, 205, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V, R437W and H450W.

In a preferred embodiment, the variant comprises a substitution at a position corresponding to position 213, in particular the substitution K213T, in combination with a substitution at one or more positions corresponding to any of positions 1, 2, 68, 71, 126, 133, 142, 144, 156, 158, 176, 185, 201, 205, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 213, in particular the substitution K213T, in combination with a substitution at one or more positions corresponding to any of positions 1, 2, 68, 71, 126, 133, 142, 144, 156, 158, 176, 185, 201, 205, 239, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 239, in particular the substitution S239A or S239Q, in combination with a substitution at one or more positions corresponding to any of positions 1, 2, 68, 71, 126, 133, 142, 144, 156, 158, 176, 185, 201, 205, 213, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, F279W, H316W, L318W, Q360S, D416V, R437W and H450W.

In a preferred embodiment, the variant comprises a substitution at a position corresponding to position 239, in particular the substitution S239A or S239Q, in combination with a substitution at one or more positions corresponding to any of positions 1, 2, 68, 71, 126, 133, 142, 144, 156, 158, 176, 185, 201, 205, 213, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 239, in particular the substitution S239A or S239Q, in combination with a substitution at one or more positions corresponding to any of positions 1, 2, 68, 71, 126, 133, 142, 144, 156, 158, 176, 185, 201, 205, 213, 279, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, F279W, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 279, in particular the substitution F279W, in combination with a substitution at one or more positions corresponding to any of positions 1, 2, 68, 71, 126, 133, 142, 144, 156, 158, 176, 185, 201, 205, 213, 239, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, H316W, L318W, Q360S, D416V, R437W and H450W.

In a preferred embodiment, the variant comprises a substitution at a position corresponding to position 279, in particular the substitution F279W, in combination with a substitution at one or more positions corresponding to any of positions 1, 2, 68, 71, 126, 133, 142, 144, 156, 158, 176, 185, 201, 205, 213, 239, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 279, in particular the substitution F279W, in combination with a substitution at one or more positions corresponding to any of positions 1, 2, 68, 71, 126, 133, 142, 144, 156, 158, 176, 185, 201, 205, 213, 239, 316, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, H316W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 316, in particular the substitution H316W, in combination with a substitution at one or more positions corresponding to any of positions 1, 2, 68, 71, 126, 133, 142, 144, 156, 158, 176, 185, 201, 205, 213, 239, 279, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, L318W, Q360S, D416V, R437W and H450W.

In a preferred embodiment, the variant comprises a substitution at a position corresponding to position 316, in particular the substitution H316W, in combination with a substitution at one or more positions corresponding to any of positions 1, 2, 68, 71, 126, 133, 142, 144, 156, 158, 176, 185, 201, 205, 213, 239, 279, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 316, in particular the substitution H316W, in combination with a substitution at one or more positions corresponding to any of positions 1, 2, 68, 71, 126, 133, 142, 144, 156, 158, 176, 185, 201, 205, 213, 239, 279, 318, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, L318W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 318, in particular the substitution L318W, in combination with a substitution at one or more positions corresponding to any of positions 1, 2, 68, 71, 126, 133, 142, 144, 156, 158, 176, 185, 201, 205, 213, 239, 279, 316, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, Q360S, D416V, R437W and H450W.

In a preferred embodiment, the variant comprises a substitution at a position corresponding to position 318, in particular the substitution L318W, in combination with a substitution at one or more positions corresponding to any of positions 1, 2, 68, 71, 126, 133, 142, 144, 156, 158, 176, 185, 201, 205, 213, 239, 279, 316, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 318, in particular the substitution L318W, in combination with a substitution at one or more positions corresponding to any of positions 1, 2, 68, 71, 126, 133, 142, 144, 156, 158, 176, 185, 201, 205, 213, 239, 279, 316, 360, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, Q360S, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 360, in particular the substitution Q360S, in combination with a substitution at one or more positions corresponding to any of positions 1, 2, 68, 71, 126, 133, 142, 144, 156, 158, 176, 185, 201, 205, 213, 239, 279, 316, 318, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W.

In a preferred embodiment, the variant comprises a substitution at a position corresponding to position 360, in particular the substitution Q360S, in combination with a substitution at one or more positions corresponding to any of positions 1, 2, 68, 71, 126, 133, 142, 144, 156, 158, 176, 185, 201, 205, 213, 239, 279, 316, 318, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 360, in particular the substitution Q360S, in combination with a substitution at one or more positions corresponding to any of positions 1, 2, 68, 71, 126, 133, 142, 144, 156, 158, 176, 185, 201, 205, 213, 239, 279, 316, 318, 416, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 416, in particular the substitution D416V, in combination with a substitution at one or more positions corresponding to any of positions 1, 2, 68, 71, 126, 133, 142, 144, 156, 158, 176, 185, 201, 205, 213, 239, 279, 316, 318, 360, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, R437W and H450W.

In a preferred embodiment, the variant comprises a substitution at a position corresponding to position 416, in particular the substitution D416V, in combination with a substitution at one or more positions corresponding to any of positions 1, 2, 68, 71, 126, 133, 142, 144, 156, 158, 176, 185, 201, 205, 213, 239, 279, 316, 318, 360, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 416, in particular the substitution D416V, in combination with a substitution at one or more positions corresponding to any of positions 1, 2, 68, 71, 126, 133, 142, 144, 156, 158, 176, 185, 201, 205, 213, 239, 279, 316, 318, 360, 437 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, R437W and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 437, in particular the substitution R437W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W.

In a preferred embodiment, the variant comprises a substitution at a position corresponding to position 437, in particular the substitution R437W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 437, in particular the substitution R437W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 450, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 450, in particular the substitution H450W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 437, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and R437W.

In a preferred embodiment, the variant comprises a substitution at a position corresponding to position 450, in particular the substitution H450W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 437, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and R437W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant comprises a substitution at a position corresponding to position 450, in particular the substitution H450W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 437, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and R437W, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant further comprises a substitution at one or more positions, e.g., at two or more positions or at three or more positions, corresponding to positions 15, 48, 49, 107, 138, 156, 181, 187, 188, 190, 197, 209, 239, 255, 264, 299, 474 and 475 of SEQ ID NO: 1.

In a preferred embodiment, the variant further comprises a substitution at one or more positions, e.g., at two or more positions or at three or more positions, corresponding to positions 15, 48, 49, 107, 138, 156, 181, 187, 188, 190, 197, 209, 239, 255, 264, 299, 474 and 475 of SEQ ID NO: 1, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In a preferred embodiment, the variant further comprises a substitution at one or more positions, e.g., at two or more positions or at three or more positions, corresponding to positions 15, 48, 49, 107, 138, 156, 181, 187, 188, 190, 197, 209, 239, 255, 264, 299, 474 and 475 of SEQ ID NO: 1, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant comprises a substitution at a position corresponding to position 15 with Ala, Arg, Asn, Asp, Cys, Gln, Glu, Gly, His, Ile, Leu, Lys, Phe, Pro, Ser, Thr, Trp, Tyr or Val, in particular with Leu, Ser or Thr.

In one embodiment, the variant comprises a substitution at a position corresponding to position 48 with Ala, Arg, Asn, Asp, Cys, Gln, Glu, His, Ile, Leu, Lys, Met, Phe, Pro, Ser, Thr, Trp, Tyr or Val, in particular with Ala.

In one embodiment, the variant comprises a substitution at a position corresponding to position 49 with Ala, Arg, Asn, Asp, Cys, Gln, Glu, Gly, His, Ile, Leu, Lys, Met, Phe, Pro, Ser, Trp, Tyr or Val, in particular with Gly, His, Ile or Leu.

In one embodiment, the variant comprises a substitution at a position corresponding to position 107 with Ala, Arg, Asn, Asp, Cys, Gln, Glu, His, Ile, Leu, Lys, Met, Phe, Pro, Ser, Thr, Trp, Tyr or Val, in particular with Ala.

In one embodiment, the variant comprises a substitution at a position corresponding to position 138 with Ala, Arg, Asn, Asp, Cys, Gin, Glu, Gly, His, Ile, Leu, Lys, Met, Phe, Pro, Ser, Thr, Trp, Tyr or Val, in particular with Phe or Tyr.

In one embodiment, the variant comprises a substitution at a position corresponding to position 156 with Ala, Arg, Asn, Asp, Cys, Gin, Glu, Gly, Ile, Leu, Lys, Met, Phe, Pro, Ser, Thr, Trp, Tyr or Val, in particular with Tyr.

In one embodiment, the variant comprises a substitution at a position corresponding to position 181 with Arg, Asn, Asp, Cys, Gin, Glu, Gly, His, Ile, Leu, Lys, Met, Phe, Pro, Ser, Thr, Trp, Tyr or Val, in particular with Asp, Glu or Thr.

In one embodiment, the variant comprises a substitution at a position corresponding to position 187 with Ala, Arg, Asn, Asp, Cys, Gin, Glu, Gly, His, Ile, Leu, Lys, Met, Phe, Pro, Thr, Trp, Tyr or Val, in particular with Asp.

In one embodiment, the variant comprises a substitution at a position corresponding to position 188 with Ala, Arg, Asp, Cys, Gin, Glu, Gly, His, Ile, Leu, Lys, Met, Phe, Pro, Ser, Thr, Trp, Tyr or Val, in particular with Ser or Thr.

In one embodiment, the variant comprises a substitution at a position corresponding to position 190 with Ala, Arg, Asp, Cys, Gin, Glu, Gly, His, Ile, Leu, Lys, Met, Phe, Pro, Ser, Thr, Trp, Tyr or Val, in particular with Phe.

In one embodiment, the variant comprises a substitution at a position corresponding to position 197 with Ala, Arg, Asn, Asp, Cys, Gin, Glu, Gly, His, Ile, Leu, Lys, Phe, Pro, Ser, Thr, Trp, Tyr or Val, in particular with Ile, Leu, Ser, Thr or Val.

In one embodiment, the variant comprises a substitution at a position corresponding to position 209 with Arg, Asn, Asp, Cys, Gin, Glu, Gly, His, Ile, Leu, Lys, Met, Phe, Pro, Ser, Thr, Trp, Tyr or Val, in particular with Val.

In one embodiment, the variant comprises a substitution at a position corresponding to position 239 with Ala, Arg, Asn, Asp, Cys, Gin, Glu, Gly, His, Ile, Leu, Lys, Met, Phe, Pro, Thr, Trp, Tyr or Val, in particular with Ala, Asn, Asp, Gin, Glu or Met.

In one embodiment, the variant comprises a substitution at a position corresponding to position 255 with Ala, Arg, Asn, Asp, Cys, Gin, Gly, His, Ile, Leu, Lys, Met, Phe, Pro, Ser, Thr, Trp, Tyr or Val, in particular with Gly or Pro.

In one embodiment, the variant comprises a substitution at a position corresponding to position 264 with Ala, Arg, Asn, Asp, Cys, Glu, Gly, His, Ile, Leu, Lys, Met, Phe, Pro, Ser, Thr, Trp, Tyr or Val, in particular with Ser.

In one embodiment, the variant comprises a substitution at a position corresponding to position 299 with Ala, Arg, Asn, Asp, Cys, Gin, Glu, His, Ile, Leu, Lys, Met, Phe, Pro, Ser, Thr, Trp, Tyr or Val, in particular with Arg.

In one embodiment, the variant comprises a substitution at a position corresponding to position 474 with Ala, Arg, Asn, Asp, Cys, Gln, Glu, His, Ile, Leu, Lys, Met, Phe, Pro, Ser, Thr, Trp, Tyr or Val, in particular with Arg, Gin, Glu or Lys.

In one embodiment, the variant comprises a substitution at a position corresponding to position 475 with Ala, Arg, Asn, Asp, Cys, Gln, Glu, His, Ile, Leu, Lys, Met, Phe, Pro, Ser, Thr, Trp, Tyr or Val, in particular with Arg, Gin, Glu or Lys.

In a preferred embodiment, the variant comprises one or more, e.g., two or more, or three or more, substitutions selected from the group consisting of M15T, M15S, M15L, G48A, T49L, T49I, G107A, W138Y, W138F, H156Y, A181T, A181E, A181D, S187D, N188S, N188T, N190F, M197S, M197T, M197V, M197L, M197I, A209V, S239Q, S239E, S239N, S239D, S239A, S239M, E255P, E255G, Q264S, G299R, G474K, G474R, G474E, G474Q, G475K, G475R, G475E and G475Q.

In another preferred embodiment, the variant comprises one or more, e.g., two or more, or three or more, substitutions selected from the group consisting of M15T, M15S, M15L, G48A, T49L, T49I, G107A, W138Y, W138F, H156Y, A181T, A181E, A181D, S187D, N188S, N188T, N190F, M197S, M197T, M197V, M197L, M197I, A209V, S239Q, S239E, S239N, S239D, S239A, S239M, E255P, E255G, Q264S, G299R, G474K, G474R, G474E, G474Q, G475K, G475R, G475E and G475Q, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 1, or (ii) amino acids 1-483 of SEQ ID NO: 1.

In another preferred embodiment, the variant comprises one or more, e.g., two or more, or three or more, substitutions selected from the group consisting of M15T, M15S, M15L, G48A, T49L, T49I, G107A, W138Y, W138F, H156Y, A181T, A181E, A181D, S187D, N188S, N188T, N190F, M197S, M197T, M197V, M197L, M197I, A209V, S239Q, S239E, S239N, S239D, S239A, S239M, E255P, E255G, Q264S, G299R, G474K, G474R, G474E, G474Q, G475K, G475R, G475E and G475Q, and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In a preferred embodiment, a variant of the invention comprises a set of substitutions selected from the group consisting of:
A1H+N2W+K176L+E185P,
A1W+N2H+K176L+E185P,
N2H+H68W+H133Y+K176L+E185P,
N2H+H68W+Y156W+K176L+E185P,
N2H+H68W+Y158W+K176L+E185P,
N2H+H68W+K176L+E185P,
N2H+H68W+K176L+E185P+I201Y+H205Y+D207V+V209D,
N2H+H68W+K176L+E185P+F279W,
N2H+H133Y+K176L+E185P+H316W+R437W,
N2H+H133Y+K176L+E185P+Q360S+R437W,
N2H+H142W+K176L+E185P+H316W+R437W,
N2H+H142W+K176L+E185P+Q360S+R437W,
N2H+P144W+K176L+E185P,
N2H+Y156W+Y158W+K176L+E185P+H316W+R437W,
N2H+Y156W+K176L+E185P+Q360S+R437W,
N2H+Y158W+K176L+E185P+I201Y+H205Y+D207V+V209D+H316W,
N2H+K176L+E185P,
N2H+K176L+E185P+H316W,
N2H+K176L+E185P+H316W+L318W+R437W,
N2H+K176L+E185P+H316W+Q360S+R437W,
N2H+K176L+E185P+H316W+R437W,
N2H+K176L+E185P+R437W,
N2H+K176L+E185P+Q360S+R437W,
N2H+K176L+E185P+H316W+Q360S+R437W,
N2H+K176L+I201Y+H205Y+K213T+Q360S+D416V+R437W,
H68W+K176L+E185P,
H68W+K176L+E185P+I201Y+H205Y+K213T+Q360S+D416V+R437W,
H68W+K176L+I201Y+H205Y+K213T+Q360S+D416V+R437W,
G71W+K176L+E185P,
N126W+K176L+I201Y+H205Y+K213T+Q360S+D416V+R437W,
H133Y+Y158W+K176L+E185P+I201Y+H205Y+K213T+Q360S+D416V+R437W,
H133Y+K176L+I201Y+H205Y+K213T+Q360S+D416V+R437W,
H142W+Y158W+K176L+E185P+I201Y+H205Y+K213T+Q360S+D416V+R437W,
H142W+K176L+E185P,
H142W+K176L+E185P+I201Y+H205Y+K213T+Q360S+D416V+R437W,
H142W+K176L+I201Y+H205Y+K213T+Q360S+D416V+R437W,
P144W+K176L+E185P,
Y156W+Y158W+K176L+E185P+I201Y+H205Y+K213T+Q360S+D416V+R437W,
Y156W+Y158W+K176L+E185P+H316W+R437W,
Y156W+K176L+E185P+Q360S+R437W,
Y156W+K176L+I201Y+H205Y+K213T+Q360S+D416V+R437W,
Y158W+K176L+E185P,
Y158W+K176L+E185P+I201Y+H205Y+D207V+V209D+H316W,
Y158W+K176L+E185P+I201Y+H205Y+K213T+H316L+L318W+Q360S+D416V+R437W,
Y158W+K176L+E185P+I201Y+H205Y+K213T+H316W+Q360S+D416V+R437W,
Y158W+K176L+E185P+I201Y+H205Y+K213T+Q360S+D416V+R437W,
Y158W+K176L+I201Y+H205Y+K213T+Q360S+D416V+R437W,
K176L+E185P,
K176L+E185P+I201Y+H205Y+K213T+Q360S+D416V+R437W,
K176L+E185P+I201Y+H205Y+R437W,
K176L+E185P+F279W,
K176L+E185P+H316W,
K176L+E185P+L318W,
K176L+E185P+H450W,
K176L+I201Y+H205Y+K213T+S239Q+Q360S+D416V+R437W,
K176L+I201Y+H205Y+K213T+H316W+Q360S+D416V+R437W,
K176L+I201Y+H205Y+K213T+L318W+Q360S+D416V+R437W,
K176L+I201Y+H205Y+K213T+Q360S+D416V+R437W,
K176L+I201Y+H205Y+K213T+Q360S+R437W,
K176L+I201Y+H205Y+K213T+D416V+R437W, and
K176L+I201Y+H205Y+Q360S+D416V+R437W.

In another preferred embodiment, a variant of the invention comprises a set of substitutions selected from the group consisting of:

A1H+N2W+K176L+E185P,
A1W+N2H+K176L+E185P,
N2H+H68W+H133Y+K176L+E185P,
N2H+H68W+Y156W+K176L+E185P,
N2H+H68W+Y158W+K176L+E185P,
N2H+H68W+K176L+E185P,
N2H+H68W+K176L+E185P+I201Y+H205Y+D207V+V209D,
N2H+H68W+K176L+E185P+F279W,
N2H+H133Y+K176L+E185P+H316W+R437W,
N2H+H133Y+K176L+E185P+Q360S+R437W,
N2H+H142W+K176L+E185P+H316W+R437W,
N2H+H142W+K176L+E185P+Q360S+R437W,
N2H+P144W+K176L+E185P,
N2H+Y156W+Y158W+K176L+E185P+H316W+R437W,
N2H+Y156W+K176L+E185P+Q360S+R437W,
N2H+Y158W+K176L+E185P+I201Y+H205Y+D207V+V209D+H316W,
N2H+K176L+E185P,
N2H+K176L+E185P+H316W,
N2H+K176L+E185P+H316W+L318W+R437W,
N2H+K176L+E185P+H316W+Q360S+R437W,
N2H+K176L+E185P+H316W+R437W,
N2H+K176L+E185P+R437W,
N2H+K176L+E185P+Q360S+R437W,
N2H+K176L+E185P+H316W+Q360S+R437W,
N2H+K176L+I201Y+H205Y+K213T+Q360S+D416V+R437W,
H68W+K176L+E185P,
H68W+K176L+E185P+I201Y+H205Y+K213T+Q360S+D416V+R437W,
H68W+K176L+I201Y+H205Y+K213T+Q360S+D416V+R437W,
G71W+K176L+E185P,
N126W+K176L+I201Y+H205Y+K213T+Q360S+D416V+R437W,
H133Y+Y158W+K176L+E185P+I201Y+H205Y+K213T+Q360S+D416V+R437W,
H133Y+K176L+I201Y+H205Y+K213T+Q360S+D416V+R437W,
H142W+Y158W+K176L+E185P+I201Y+H205Y+K213T+Q360S+D416V+R437W,
H142W+K176L+E185P,

H142W+K176L+E185P+I201Y+H205Y+K213T+Q360S+ D416V+R437W,
H142W+K176L+I201Y+H205Y+K213T+Q360S+D416V+ R437W,
P144W+K176L+E185P,
Y156W+Y158W+K176L+E185P+I201Y+H205Y+ K213T+Q360S+D416V+R437W,
Y156W+Y158W+K176L+E185P+H316W+R437W,
Y156W+K176L+E185P+Q360S+R437W,
Y156W+K176L+I201Y+H205Y+K213T+Q360S+D416V+ R437W,
Y158W+K176L+E185P,
Y158W+K176L+E185P+I201Y+H205Y+D207V+V209D+ H316W,
Y158W+K176L+E185P+I201Y+H205Y+K213T+H316L+ L318W+Q360S+D416V+R437W,
Y158W+K176L+E185P+I201Y+H205Y+K213T+ H316W+Q360S+D416V+R437W,
Y158W+K176L+E185P+I201Y+H205Y+K213T+Q360S+ D416V+R437W,
Y158W+K176L+I201Y+H205Y+K213T+Q360S+D416V+ R437W,
K176L+E185P,
K176L+E185P+I201Y+H205Y+K213T+Q360S+D416V+ R437W,
K176L+E185P+I201Y+H205Y+R437W,
K176L+E185P+F279W,
K176L+E185P+H316W,
K176L+E185P+L318W,
K176L+E185P+H450W,
K176L+I201Y+H205Y+K213T+S239Q+Q360S+D416V+ R437W,
K176L+I201Y+H205Y+K213T+H316W+Q360S+D416V+ R437W,
K176L+I201Y+H205Y+K213T+L318W+Q360S+D416V+ R437W,
K176L+I201Y+H205Y+K213T+Q360S+D416V+R437W,
K176L+I201Y+H205Y+K213T+Q360S+R437W,
K176L+I201Y+H205Y+K213T+D416V+R437W, and
K176L+I201Y+H205Y+Q360S+D416V+R437W. 6 and the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to (i) the mature polypeptide of SEQ ID NO: 14, or (ii) amino acids 1-481 of SEQ ID NO: 14.

In one embodiment, the variant further comprises a deletion at both of the two positions immediately before the position corresponding to position 180 of SEQ ID NO: 1. i.e., a deletion of the two amino acids corresponding to positions 181 and 182 of SEQ ID NO: 2.

In another embodiment, the variant further comprises a deletion of two amino acids after the position corresponding to position 177 of SEQ ID NO: 1 and before the position corresponding to position 180 of SEQ ID NO: 1. I.e., a deletion of two amino acids in the R179-G180-I181-G182 peptide of SEQ ID NO: 2, or homologous amino acids in any of SEQ ID NO: 3 to 11.

The variants may further comprise one or more (e.g., several) additional alterations, e.g., one or more (e.g., several) additional substitutions.

The additional amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of 300 to 700, e.g., 350 to 650, 400 to 600, 450 to 500 or 470 to 490, amino acids.

In a preferred embodiment, the variant has increased thermostability compared to the mature polypeptide of SEQ ID NO: 1 at high temperature, low calcium and low pH in the presence of at least 0.1% starch, e.g., in the presence of 0.9% or 1% starch.

In the context of the present invention "high temperature" means temperatures from 70-120° C., preferably 80-100° C., more preferably 85-95° C.

In the context of the present invention the term "low pH" means a pH in the range from 4-6, preferably 4.2-5.5, more preferably 4.5-5.

In the context of the present invention the term "low calcium" means free calcium levels lower than 60 ppm, preferably 40 ppm, more preferably 25 ppm, even more preferably 5 ppm calcium. 0.125 mM $CaCl_2$ provides 5 ppm calcium.

In one embodiment, the variant has increased thermostability compared to the mature polypeptide of SEQ ID NO: 1 when incubated with 0.125 mM $CaCl_2$, 0.1% starch at 95° C. and pH 4.8. In another embodiment, the variant has increased thermostability compared to the mature polypeptide of SEQ ID NO: 1 when incubated with 0.125 mM $CaCl_2$, 0.1% starch at 95° C. and pH 4.5.

In another embodiment, the variant has increased thermostability compared to the mature polypeptide of SEQ ID NO: 1 when incubated with 0.125 mM $CaCl_2$, 0.9% starch at 95° C. and pH 4.8. In another embodiment, the variant has increased thermostability compared to the mature polypeptide of SEQ ID NO: 1 when incubated with 0.125 mM $CaCl_2$, 0.9% starch at 95° C. and pH 4.5.

In another embodiment, the variant has increased thermostability compared to the mature polypeptide of SEQ ID NO: 1 when incubated with 0.125 mM $CaCl_2$, 1% starch at 95° C. and pH 4.8. In another embodiment, the variant has increased thermostability compared to the mature polypeptide of SEQ ID NO: 1 when incubated with 0.125 mM $CaCl_2$, 1% starch at 95° C. and pH 4.5.

The skilled person will know how to determine thermostabiity of the enzymes. It may be done by determining the residual activity half-life as shown in the Examples of the present application. The skilled person will know how to choose the relevant conditions for the assay, such as the incubation time.

In a preferred embodiment, the variant has an increased residual activity half-life compared to the mature polypeptide of SEQ ID NO: 1 at high temperature, low calcium and low pH in the presence of at least 0.1% starch, e.g., in the presence of 0.9% or 1% starch. In one preferred embodiment, the variant has an increased residual activity half-life compared to the mature polypeptide of SEQ ID NO: 1 when incubated with 0.125 mM $CaCl_2$, 0.1% starch at 95° C. and pH 4.8. In another preferred embodiment, the variant has an increased residual activity half-life compared to the mature polypeptide of SEQ ID NO: 1 when incubated with 0.125 mM $CaCl_2$, 0.1% starch at 95° C. and pH 4.5. In another preferred embodiment, the variant has an increased residual activity half-life compared to the mature polypeptide of SEQ ID NO: 1 when incubated with 0.125 mM $CaCl_2$, 0.9% starch at 95° C. and pH 4.8. In another preferred embodiment, the variant has an increased residual activity half-life compared to the mature polypeptide of SEQ ID NO: 1 when incubated with 0.125 mM $CaCl_2$, 0.9% starch at 95° C. and pH 4.5. In another preferred embodiment, the variant has an increased residual activity half-life compared to the mature polypeptide of SEQ ID NO: 1 when incubated with 0.125 mM $CaCl_2$, 1% starch at 95° C. and pH 4.8. In another preferred embodiment, the variant has an increased residual activity half-life compared to the mature polypeptide of SEQ ID NO: 1 when incubated with 0.125 mM $CaCl_2$, 1% starch at 95° C. and pH 4.5.

In a preferred embodiment, the variant has a residual activity half-life, when incubated with 0.125 mM $CaCl_2$, 0.9% starch at 95° C. and pH 4.8, which is at least 5 minutes, e.g., at least 7 minutes or at least 10 minutes. In a more preferred embodiment, the variant has a residual activity half-life, when incubated with 0.125 mM $CaCl_2$, 0.9% starch at 95° C. and pH 4.8, which is at least 15 minutes, e.g., at least 20 minutes or at least 30 minutes. In one embodiment, the variant has a residual activity half-life, when incubated with 0.125 mM $CaCl_2$, 0.9% starch at 95° C. and pH 4.8, which is at least 40 minutes, e.g., at least 50 minutes or at least 60 minutes. In a preferred embodiment, the variant has a residual activity half-life, when incubated with 0.125 mM $CaCl_2$, 0.9% starch at 95° C. and pH 4.5, which is at least 1 minute, e.g., at least 2 minutes or at least 5 minutes. In a more preferred embodiment, the variant has a residual activity half-life, when incubated with 0.125 mM $CaCl_2$, 0.9% starch at 95° C. and pH 4.5, which is at least 8 minutes, e.g., at least 10 minutes or at least 12 minutes. In one embodiment, the variant has a residual activity half-life, when incubated with 0.125 mM $CaCl_2$, 0.9% starch at 95° C. and pH 4.8, which is at least 15 minutes, e.g., at least 20 minutes or at least 25 minutes.

In a preferred embodiment, the variant has increased thermostability compared to the parent enzyme at high temperature, low calcium and low pH in the presence of at least 0.1% starch, e.g., in the presence of 0.9% or 1% starch.

In another preferred embodiment, the variant has an increased residual activity half-life compared to the parent enzyme at high temperature, low calcium and low pH in the presence of at least 0.1% starch, e.g., in the presence of 0.9% or 1% starch.

In one embodiment, the variant has increased thermostability, e.g., an increased residual activity half-life, compared to the parent enzyme when incubated with 0.125 mM $CaCl_2$, 0.1% starch at 95° C. and pH 4.8. In another embodiment, the variant has increased thermostability, e.g., an increased residual activity half-life, compared to the parent enzyme when incubated with 0.125 mM $CaCl_2$, 0.1% starch at 95° C. and pH 4.5.

In one embodiment, the variant has increased thermostability, e.g., an increased residual activity half-life, compared to the parent enzyme when incubated with 0.125 mM $CaCl_2$, 0.9% starch at 95° C. and pH 4.8. In another embodiment, the variant has increased thermostability, e.g., an increased residual activity half-life, compared to the parent enzyme when incubated with 0.125 mM $CaCl_2$, 0.9% starch at 95° C. and pH 4.5.

In one embodiment, the variant has increased thermostability, e.g., an increased residual activity half-life, compared to the parent enzyme when incubated with 0.125 mM $CaCl_2$, 1% starch at 95° C. and pH 4.8. In another embodiment, the variant has increased thermostability, e.g., an increased residual activity half-life, compared to the parent enzyme when incubated with 0.125 mM $CaCl_2$, 1% starch at 95° C. and pH 4.5.

In other embodiments, the variant has improved catalytic efficiency, improved catalytic rate, improved chemical stability, improved oxidation stability, improved specific activity, improved stability under storage conditions, improved substrate binding, improved substrate cleavage, improved substrate specificity, improved substrate stability, improved surface properties, improved thermal activity, or improved thermostability compared to the parent enzyme.

Parent Alpha-Amylase

The variant is preferably a variant of a parent alpha-amylase selected from the group consisting of:

(a) a polypeptide having at least 60% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14; or (b) a fragment of the mature polypeptide of any of SEQ ID NOs: 1, 2, 3, 4, 5, 6, 7, 8, 9, 10, 11, 12, 13 or 14, which has alpha-amylase activity.

In one embodiment, the parent alpha-amylase has at least 65%, e.g., at least 70%, at least 75%, at least 80%, at least 85%, at least 90%, at least 95%, at least 96%, at least 97%, at least 98%, at least 99% or 100% sequence identity to (i)

the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14.

In one embodiment, the parent alpha-amylase has at least 60%, e.g., at least 65%, at least 70%, at least 75%, at least 80%, at least 85%, at least 90%, at least 95%, at least 96%, at least 97%, at least 98%, at least 99% or 100% sequence identity to (i) the mature polypeptide of SEQ ID NO: 1, or (ii) amino acids 1-483 of SEQ ID NO: 1.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 2, (ii) the mature polypeptide of SEQ ID NO: 2 comprising the deletions I181*+G182*, (iii) amino acids 1-483 of SEQ ID NO: 2, or (iv) amino acids 1-483 of SEQ ID NO: 2 comprising the deletions I181*+G182*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 3, (ii) the mature polypeptide of SEQ ID NO: 3 comprising the deletions T183*+G184*, (iii) amino acids 1-485 of SEQ ID NO: 3, or (iv) amino acids 1-485 of SEQ ID NO: 3 comprising the deletions T183*+G184*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 4, (ii) the mature polypeptide of SEQ ID NO: 4 comprising the deletions T180*+G181*, (iii) amino acids 1-482 of SEQ ID NO: 4, or (iv) amino acids 1-482 of SEQ ID NO: 4 comprising the deletions T180*+G181*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 5, (ii) the mature polypeptide of SEQ ID NO: 5 comprising the deletions T182*+G183*, (iii) amino acids 1-484 of SEQ ID NO: 5, or (iv) amino acids 1-484 of SEQ ID NO: 5 comprising the deletions T182*+G183*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 6, (ii) the mature polypeptide of SEQ ID NO: 6 comprising the deletions E178*+G179*, (iii) amino acids 1-483 of SEQ ID NO: 6, or (iv) amino acids 1-483 of SEQ ID NO: 6 comprising the deletions E178*+G179*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 7, (ii) the mature polypeptide of SEQ ID NO: 7 comprising the deletions T183*+G184*, (iii) amino acids 1-485 of SEQ ID NO: 7, or (iv) amino acids 1-485 of SEQ ID NO: 7 comprising the deletions T183*+G184*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 8, (ii) the mature polypeptide of SEQ ID NO: 8 comprising the deletions D183*+G184*, (iii) amino acids 1-486 of SEQ ID NO: 8, or (iv) amino acids 1-486 of SEQ ID NO: 8 comprising the deletions D183*+G184*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 9, (ii) the mature polypeptide of SEQ ID NO: 9 comprising the deletions D183*+G184*, (iii) amino acids 1-485 of SEQ ID NO: 9, or (iv) amino acids 1-485 of SEQ ID NO: 9 comprising the deletions D183*+G184*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 10, (ii) the mature polypeptide of SEQ ID NO: 10 comprising the deletions D183*+G184*, (iii) amino acids 1-485 of SEQ ID NO: 10, or (iv) amino acids 1-485 of SEQ ID NO: 10 comprising the deletions D183*+G184*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 11, (ii) the mature polypeptide of SEQ ID NO: 11 comprising the deletions H183*+G184*, (iii) amino acids 1-485 of SEQ ID NO: 11, or (iv) amino acids 1-485 of SEQ ID NO: 11 comprising the deletions H183*+G184*.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 12, or (ii) amino acids 1-480 of SEQ ID NO: 12.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 13, or (ii) amino acids 1-483 of SEQ ID NO: 13.

In another embodiment, the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 14, or (ii) amino acids 1-481 of SEQ ID NO: 14.

In one embodiment, the parent alpha-amylase comprises or consists of the mature polypeptide of any of SEQ ID NOs: 1, 2, 3, 4, 5, 6, 7, 8, 9, 10, 11, 12, 13 or 14.

In one embodiment, the parent alpha-amylase comprises or consists of amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14.

In another embodiment, the parent alpha-amylase is a fragment of the mature polypeptide of any of SEQ ID NOs: 1, 2, 3, 4, 5, 6, 7, 8, 9, 10, 11, 12, 13 or 14, wherein the fragment has alpha-amylase activity.

In one embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the parent alpha-amylase.

In one embodiment, the total number of substitutions in the variants of the present invention is 2-20, e.g., 2-10 and 2-5, such as 2, 3, 4, 5, 6, 7, 8, 9 or 10 substitutions.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial alpha-amylase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* alpha-amylase, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* alpha-amylase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* alpha-amylase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and *Agricultural Research* Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having alpha-amylase activity, comprising: (a) introducing into a parent alpha-amylase an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Sac-*

*charomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene. Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor,*

*Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising an alpha-amylase variant and at least one additional enzyme. The additional enzyme(s) may be selected from the group consisting of beta-amylase, cellulase (beta-glucosidase, cellobiohydrolase and endoglucanase), glucoamylase, hemicellulsae (e.g., xylanase), isoamylase, isomerase, lipase, phytase, protease, pullulanase, and/or other enzymes useful in a commercial process in conjunction with an alpha-amylase. The additional enzyme may also be a second alpha-amylase. Such enzymes are known in the art in starch processing, sugar conversion, fermentations for alcohol and other useful end-products, commercial detergents and cleaning aids, stain removal, fabric treatment or desizing, and the like.

Uses

The variants of the present invention possess valuable properties allowing for a variety of industrial applications. In particular, the variants may be used in detergents, in particular laundry detergent compositions and dishwashing detergent compositions, hard surface cleaning compositions, and for desizing textiles, fabrics or garments, production of pulp and paper, beer making, ethanol production, and starch conversion processes.

The alpha-amylase variants may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the variant of the invention also comprise an AMG, pullulanase, and other alpha-amylases.

Further, the variants are particularly useful in the production of sweeteners and ethanol (see, e.g., U.S. Pat. No. 5,231,017, which is hereby incorporated by reference), such as fuel, drinking and industrial ethanol, from starch or whole grains.

The variants may also be used for desizing of textiles, fabrics, and garments (see, e.g., WO 95/21247, U.S. Pat. No. 4,643,736, and EP 119920, which are incorporated herein by reference), beer making or brewing, and in pulp and paper production or related processes.

Starch Processing

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

In general, alcohol production (ethanol) from whole grain can be separated into 4 main steps: milling, liquefaction, saccharification, and fermentation.

The grain is milled in order to open up the structure and allow for further processing. Two processes used are wet or dry milling. In dry milling, the whole kernel is milled and used in the remaining part of the process. Wet milling gives a very good separation of germ and meal (starch granules and protein) and is with a few exceptions applied at locations where there is a parallel production of syrups.

In the liquefaction process the starch granules are solubilized by hydrolysis to maltodextrins mostly of a DP higher than 4. The hydrolysis may be carried out by acid treatment or enzymatically by an alpha-amylase. Acid hydrolysis is used on a limited basis. The raw material can be milled whole grain or a side stream from starch processing.

During a typical enzymatic liquefaction, the long-chained starch is degraded into branched and linear shorter units (maltodextrins) by an alpha-amylase. Enzymatic liquefaction is generally carried out as a three-step hot slurry process. The slurry is heated to between 60-95° C. (e.g., 77-86° C., 80-85° C., or 83-85° C.) and the enzyme(s) is (are) added. The liquefaction process is carried out at 85° C. for 1-2 hours. The pH is generally between 5.5 and 6.2. In order to ensure optimal enzyme stability under these conditions, 1 mM of calcium is added (to provide about 40 ppm free calcium ions). After such treatment, the liquefied starch will have a "dextrose equivalent" (DE) of 10-15.

The slurry is subsequently jet-cooked at between 95-140° C., e.g., 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Liquefied starch-containing material is saccharified in the presence of saccharifying enzymes such as glucoamylases. The saccharification process may last for 12 hours to 120 hours (e.g., 12 to 90 hours, 12 to 60 hours and 12 to 48 hours).

However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours.

Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc p$\alpha$1-6Glc p$\alpha$1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list is only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn. Accordingly, in the first aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. In an embodiment a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect the invention relates to processes for producing fermentation products, especially ethanol, from starch-containing material, which process includes a liquefaction step and sequentially or simultaneously performed saccharification and fermentation steps.

Consequently, the invention relates to processes for producing fermentation products from starch-containing material comprising the steps of:

(a) liquefying starch-containing material in the presence of an alpha-amylase variant, or;

(b) saccharifying the liquefied material obtained in step (a) using a carbohydrate-source generating enzyme;

(c) fermenting using a fermenting organism.

In an aspect, a pullulanase such as a family GH57 pullulanase is also used in the liquefaction step. In an embodiment a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In an embodiment the carbohydrate-source generating enzyme is a glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; a strain of the genus *Pachykytospora*, e.g., a strain of *Pachykytospora papyracea*; or a strain of the genus *Leucopaxillus*, e.g., *Leucopaxillus giganteus*; or a strain of the genus *Peniophora*, e.g., a strain of the species *Peniophora rufomarginata*; or a mixture thereof. Saccharification step (b) and fermentation step (c) may be carried out either sequentially or simultaneously. A pullulanase and/or metalloprotease may be added during saccharification and/or fermentation when the process is carried out as a sequential saccharification and fermentation process and before or during fermentation when steps (b) and (c) are carried out simultaneously (SSF process). The pullulanase and/or metalloprotease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase variant and optionally pullulanase variant and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Beer Making

The alpha-amylase variants may also be used in a beer-making process and similar fermentations; the alpha-amylases will typically be added during the mashing process.

The process is substantially similar to the milling, liquefaction, saccharification, and fermentation processes described above.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5.

During ethanol production, acids can be added to lower the pH in the beer well, to reduce the risk of microbial contamination prior to distillation.

In some embodiments, a phytase is added to the slurry. In other embodiments, in addition to phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

Currently, it is believed that commercially available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at low pH.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hrs, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch maybe further hydrolyzed at a temperature ranging from about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Pulp and Paper Production

The alpha-amylase variants may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase variants are especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylase variants may also be useful in modifying starch where enzymatically modified starch is used in papermaking together with alkaline fillers such as calcium carbonate, kaolin and clays. With the alpha-amylase variants it is possible to modify the starch in the presence of the filler thus allowing for a simpler integrated process.

Desizinq of Textiles, Fabrics and Garments

The alpha-amylase variants may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing process is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size leads to some fiber damage because of the rather aggressive chemicals used. Accordingly, it would be desirable to use the alpha-amylase variants as they have an improved performance in alkaline solutions. The alpha-amylase variants may be used alone or in combination with a cellulase when desizing cellulose-containing fabric or textile.

Desizing and bleaching processes are well known in the art. For instance, such processes are described in e.g., WO 95/21247, U.S. Pat. No. 4,643,736, EP 119920, which are hereby incorporated by reference.

Cleaning Processes and Detergent Compositions

The alpha-amylase variants may be added as a component of a detergent composition for various cleaning or washing processes, including laundry and dishwashing. For example, the variants may be used in the detergent compositions described in WO 96/23874 and WO 97/07202.

The alpha-amylase variants may be incorporated in detergents at conventionally employed concentrations. For example, a variant of the invention may be incorporated in an amount corresponding to 0.00001-10 mg (calculated as pure, active enzyme protein) of alpha-amylase per liter of wash/dishwash liquor using conventional dosing levels of detergent.

The detergent composition may for example be formulated as a hand or machine laundry detergent composition, including a laundry additive composition suitable for pre-treatment of stained fabrics and a rinse added fabric softener composition or be formulated as a detergent composition for use in general household hard surface cleaning operations, or be formulated for hand or machine dishwashing operations.

The detergent composition may further comprise one or more other enzymes, such as a lipase, peroxidase, protease, another amylolytic enzyme, e.g., another alpha-amylase, glucoamylase, maltogenic amylase, CGTase, cellulase, mannanase (such as Mannaway™ from Novozymes, Denmark)), pectinase, pectin lyase, cutinase, and/or laccase.

In general the properties of the chosen enzyme(s) should be compatible with the selected detergent (i.e., pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive, e.g., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols, fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition may be in any convenient form, e.g., a bar, a tablet, a powder, a granule, a paste or a liquid. A liquid detergent may be aqueous, typically containing up to about 70% water and 0 to about 30% organic solvent, or non-aqueous.

The detergent composition comprises one or more surfactants, which may be non-ionic including semi-polar and/or anionic and/or cationic and/or zwitterionic. The surfactants are typically present at a level of from about 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0 to about 65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as polyacrylates, maleiclacrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxy acids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19708 and WO 92/19709.

The detergent may also contain other conventional detergent ingredients such as, e.g., fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

The detergent compositions may comprise any enzyme in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor.

One or more of the variant enzymes described herein may additionally be incorporated in the detergent formulations disclosed in WO 97/07202, which is hereby incorporated as reference. The invention is further defined by the following embodiments:

Embodiment 1

An alpha-amylase variant comprising an alteration at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1, wherein the variant has at least 60% and less than 100% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14, and wherein the variant has alpha-amylase activity.

Embodiment 2

The variant of Embodiment 1, which is an isolated alpha-amylase variant.

Embodiment 3

The variant of any of Embodiments 1-2, wherein the variant comprises:
an insertion or a substitution at a position corresponding to position 1 with Arg, Asn, Asp, Cys, Gln, Glu, Gly, His, Ile, Leu, Lys, Met, Phe, Pro, Ser, Thr, Trp, Tyr or Val, in particular an insertion of or a substitution with His, Phe, Trp or Tyr, preferably His or Trp;
an insertion or a substitution at a position corresponding to position 2 with Ala, Arg, Asp, Cys, Gln, Glu, Gly, His, Ile, Leu, Lys, Met, Phe, Pro, Ser, Thr, Trp, Tyr or Val, in particular an insertion of or a substitution with His, Phe, Trp or Tyr, preferably His or Trp;

a substitution at a position corresponding to position 68 with Ala, Arg, Asn, Asp, Cys, Gln, Glu, Gly, Ile, Leu, Lys, Met, Phe, Pro, Ser, Thr, Trp, Tyr or Val, in particular with Phr, Trp or Tyr, preferably with Trp;

a substitution at a position corresponding to position 71 with Ala, Arg, Asn, Asp, Cys, Gln, Glu, His, Ile, Leu, Lys, Met, Phe, Pro, Ser, Thr, Trp, Tyr or Val, in particular with His, Phe, Trp or Tyr, preferably with Trp;

a substitution at a position corresponding to position 126 with Ala, Arg, Asp, Cys, Gln, Glu, Gly, His, Ile, Leu, Lys, Met, Phe, Pro, Ser, Thr, Trp, Tyr or Val, in particular with His, Phe, Trp or Tyr, preferably with Trp;

a substitution at a position corresponding to position 133 with Ala, Arg, Asn, Asp, Cys, Gln, Glu, Gly, Ile, Leu, Lys, Met, Phe, Pro, Ser, Thr, Trp, Tyr or Val, in particular with Phe, Trp or Tyr, preferably with Tyr;

a substitution at a position corresponding to position 142 with Ala, Arg, Asn, Asp, Cys, Gln, Glu, Gly, Ile, Leu, Lys, Met, Phe, Pro, Ser, Thr, Trp, Tyr or Val, in particular with Phe, Trp or Tyr, preferably with Trp;

a substitution at a position corresponding to position 144 with Ala, Arg, Asn, Asp, Cys, Gln, Glu, Gly, His, Ile, Leu, Lys, Met, Phe, Ser, Thr, Trp, Tyr or Val, in particular with His, Phe, Trp or Tyr, preferably with Trp;

a substitution at a position corresponding to position 156 with Ala, Arg, Asn, Asp, Cys, Gln, Glu, Gly, His, Ile, Leu, Lys, Met, Phe, Pro, Ser, Thr, Trp, Tyr or Val, in particular with His, Phe or Trp, preferably with Trp;

a substitution at a position corresponding to position 158 with Ala, Arg, Asn, Asp, Cys, Gln, Glu, Gly, His, Ile, Leu, Lys, Met, Phe, Pro, Ser, Thr, Trp, Tyr or Val, in particular with His, Phe or Trp, preferably with Trp;

a substitution at a position corresponding to position 176 with Ala, Arg, Asn, Asp, Cys, Gln, Glu, Gly, His, Ile, Leu, Met, Phe, Pro, Ser, Thr, Trp, Tyr or Val, in particular with Leu;

a substitution at a position corresponding to position 185 with Ala, Arg, Asn, Asp, Cys, Gln, Gly, His, Ile, Leu, Lys, Met, Phe, Pro, Ser, Thr, Trp, Tyr or Val, in particular with Pro;

a substitution at a position corresponding to position 201 with Ala, Arg, Asn, Asp, Cys, Gln, Glu, Gly, His, Leu, Lys, Met, Phe, Pro, Ser, Thr, Trp, Tyr or Val, in particular with Tyr;

a substitution at a position corresponding to position 205 with Ala, Arg, Asn, Asp, Cys, Gln, Glu, Gly, Ile, Leu, Lys, Met, Phe, Pro, Ser, Thr, Trp, Tyr or Val, in particular with Tyr;

a substitution at a position corresponding to position 213 with Ala, Arg, Asn, Asp, Cys, Gln, Glu, Gly, His, Ile, Leu, Met, Phe, Pro, Ser, Thr, Trp, Tyr or Val, in particular with Thr;

a substitution at a position corresponding to position 239 with Ala, Arg, Asn, Asp, Cys, Gln, Glu, Gly, His, Ile, Leu, Lys, Met, Phe, Pro, Thr, Trp, Tyr or Val, in particular with Ala or Gln;

a substitution at a position corresponding to position 279 with Ala, Arg, Asn, Asp, Cys, Gln, Glu, Gly, His, Ile, Leu, Lys, Met, Pro, Ser, Thr, Trp, Tyr or Val, in particular with His, Trp or Tyr, preferably with Trp;

a substitution at a position corresponding to position 316 with Ala, Arg, Asn, Asp, Cys, Gln, Glu, Gly, Ile, Leu, Lys, Met, Phe, Pro, Ser, Thr, Trp, Tyr or Val, in particular with Phe, Trp or Tyr, preferably with Trp;

a substitution at a position corresponding to position 318 with Ala, Arg, Asn, Asp, Cys, Gln, Glu, Gly, His, Ile, Lys, Met, Phe, Pro, Ser, Thr, Trp, Tyr or Val, in particular with His, Phe, Trp or Tyr, preferably with Trp;

a substitution at a position corresponding to position 360 with Ala, Arg, Asn, Asp, Cys, Glu, Gly, His, Ile, Leu, Lys, Met, Phe, Pro, Ser, Thr, Trp, Tyr or Val, in particular with Ser;

a substitution at a position corresponding to position 416 with Ala, Arg, Asp, Cys, Gln, Glu, Gly, His, Ile, Leu, Lys, Met, Phe, Pro, Ser, Thr, Trp, Tyr or Val, in particular with Val;

a substitution at a position corresponding to position 437 with Ala, Asn, Asp, Cys, Gln, Glu, Gly, His, Ile, Leu, Lys, Met, Phe, Pro, Ser, Thr, Trp, Tyr or Val, in particular with His, Phe, Trp or Tyr, preferably with Trp; or a substitution at a position corresponding to position 450 with Ala, Arg, Asn, Asp, Cys, Gln, Glu, Gly, Ile, Leu, Lys, Met, Phe, Pro, Ser, Thr, Trp, Tyr or Val, in particular with Phe, Trp or Tyr, preferably with Trp.

Embodiment 4

The variant of any of Embodiments 1-3, wherein the variant has at least 65%, e.g., at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14.

Embodiment 5

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 1, or (ii) amino acids 1-483 of SEQ ID NO: 1.

Embodiment 6

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 2, (ii) the mature polypeptide of SEQ ID NO: 2 comprising the deletions I181*+G182*, (iii) amino acids 1-483 of SEQ ID NO: 2, or (iv) amino acids 1-483 of SEQ ID NO: 2 comprising the deletions I181*+G182*.

Embodiment 7

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 3, (ii) the mature polypeptide of SEQ ID NO: 3 comprising the deletions T183*+G184*, (iii) amino acids 1-485 of SEQ ID NO: 3, or (iv) amino acids 1-485 of SEQ ID NO: 3 comprising the deletions T183*+G184*.

Embodiment 8

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 4, (ii) the mature polypeptide of SEQ ID NO: 4 comprising the deletions T180*+G181*, (iii) amino acids 1-482 of SEQ ID NO: 4, or (iv) amino acids 1-482 of SEQ ID NO: 4 comprising the deletions T180*+G181*.

Embodiment 9

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 5, (ii) the mature polypeptide of SEQ ID NO: 5 comprising the deletions T182*+G183*, (iii) amino acids 1-484 of SEQ ID NO: 5, or (iv) amino acids 1-484 of SEQ ID NO: 5 comprising the deletions T182*+G183*.

Embodiment 10

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 6, (ii) the mature polypeptide of SEQ ID NO: 6 comprising the deletions E178*+G179*, (iii) amino acids 1-483 of SEQ ID NO: 6, or (iv) amino acids 1-483 of SEQ ID NO: 6 comprising the deletions E178*+G180*.

Embodiment 11

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 7, (ii) the mature polypeptide of SEQ ID NO: 7 comprising the deletions T183*+G184*, (iii) amino acids 1-485 of SEQ ID NO: 7, or (iv) amino acids 1-485 of SEQ ID NO: 7 comprising the deletions T183*+G184*.

Embodiment 12

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 8, (ii) the mature polypeptide of SEQ ID NO: 8 comprising the deletions D183*+G184*, (iii) amino acids 1-485 of SEQ ID NO: 8, or (iv) amino acids 1-485 of SEQ ID NO: 8 comprising the deletions D183*+G184*.

Embodiment 13

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 9, (ii) the mature polypeptide of SEQ ID NO: 9 comprising the deletions D183*+G184*, (iii) amino acids 1-485 of SEQ ID NO: 9, or (iv) amino acids 1-485 of SEQ ID NO: 9 comprising the deletions D183*+G184*.

Embodiment 14

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 10, (ii) the mature polypeptide of SEQ ID NO: 10 comprising the deletions D183*+G184*, (iii) amino acids 1-485 of SEQ ID NO: 10, or (iv) amino acids 1-485 of SEQ ID NO: 10 comprising the deletions D183*+G184*.

Embodiment 15

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 11, (ii) the mature polypeptide of SEQ ID NO: 11 comprising the deletions H183*+G184*, (iii) amino acids 1-485 of SEQ ID NO: 11, or (iv) amino acids 1-485 of SEQ ID NO: 11 comprising the deletions H183*+G184*.

Embodiment 16

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 12, or (ii) amino acids 1-480 of SEQ ID NO: 12.

Embodiment 17

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 13, or (ii) amino acids 1-483 of SEQ ID NO: 13.

Embodiment 18

The variant of any of Embodiments 1-3, wherein the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98% or at least 99%, but less than 100%, sequence identity to (i) the mature polypeptide of SEQ ID NO: 14, or (ii) amino acids 1-481 of SEQ ID NO: 14.

Embodiment 19

The variant of any of Embodiments 1-18, which is a variant of a parent alpha-amylase selected from the group consisting of:
(a) a polypeptide having at least 60% sequence identity to (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13, amino acids 1 to 481 of SEQ ID NO: 14; or
(b) a fragment of the mature polypeptide of any of SEQ ID NOs: 1, 2, 3, 4, 5, 6, 7, 8, 9, 10, 11, 12, 13 or 14, which has alpha-amylase activity.

Embodiment 20

The variant of Embodiment 19, wherein the parent alpha-amylase has at least 60%, e.g., at least 65%, at least 70%, at least 75%, at least 80%, at least 85%, at least 90%, at least 95%, at least 96%, at least 97%, at least 98%, at least 99% or 100% sequence identity to (i) the mature polypeptide of any of SEQ ID NOs: 1, 2, 3, 4, 5, 6, 7, 8, 9, 10, 11, 12 or 13, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13, amino acids 1 to 481 of SEQ ID NO: 14.

Embodiment 21

The variant of Embodiment 19, wherein the parent alpha-amylase has at least 60%, e.g., at least 65%, at least 70%, at least 75%, at least 80%, at least 85%, at least 90%, at least 95%, at least 96%, at least 97%, at least 98%, at least 99% or 100% sequence identity to (i) the mature polypeptide of SEQ ID NO: 1, or (ii) amino acids 1-483 of SEQ ID NO: 1.

Embodiment 22

The variant of Embodiment 19, wherein the parent alpha-amylase has at least 60%, e.g., at least 65%, at least 70%, at least 75%, at least 80%, at least 85%, at least 90%, at least 95%, at least 96%, at least 97%, at least 98%, at least 99% or 100% sequence identity to (i) the mature polypeptide of SEQ ID NO: 2, (ii) the mature polypeptide of SEQ ID NO: 2 comprising the deletions I181*+G182*, (iii) amino acids 1-483 of SEQ ID NO: 2, or (iv) amino acids 1-483 of SEQ ID NO: 2 comprising the deletions I181*+G182*.

Embodiment 23

The variant of Embodiment 19, wherein the parent alpha-amylase has at least 60%, e.g., at least 65%, at least 70%, at least 75%, at least 80%, at least 85%, at least 90%, at least 95%, at least 96%, at least 97%, at least 98%, at least 99% or 100% sequence identity to (i) the mature polypeptide of SEQ ID NO: 3, (ii) the mature polypeptide of SEQ ID NO: 3 comprising the deletions T183*+G184*, (iii) amino acids 1-485 of SEQ ID NO: 3, or (iv) amino acids 1-485 of SEQ ID NO: 3 comprising the deletions T183*+G184*.

Embodiment 24

The variant of Embodiment 19, wherein the parent alpha-amylase has at least 60%, e.g., at least 65%, at least 70%, at least 75%, at least 80%, at least 85%, at least 90%, at least 95%, at least 96%, at least 97%, at least 98%, at least 99% or 100% sequence identity to (i) the mature polypeptide of SEQ ID NO: 4, (ii) the mature polypeptide of SEQ ID NO: 4 comprising the deletions T180*+G181*, (iii) amino acids 1-482 of SEQ ID NO: 4, or (iv) amino acids 1-482 of SEQ ID NO: 4 comprising the deletions T180*+G181*.

Embodiment 25

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 5, (ii) the mature polypeptide of SEQ ID NO: 5 comprising the deletions T182*+G183*, (iii) amino acids 1-484 of SEQ ID NO: 5, or (iv) amino acids 1-484 of SEQ ID NO: 5 comprising the deletions T182*+G183*.

Embodiment 26

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 6, (ii) the mature polypeptide of SEQ ID NO: 6 comprising the deletions E178*+G179*, (iii) amino acids 1-483 of SEQ ID NO: 6, or (iv) amino acids 1-483 of SEQ ID NO: 6 comprising the deletions E178*+G179*.

Embodiment 27

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 7, (ii) the mature polypeptide of SEQ ID NO: 7 comprising the deletions T183*+G184*, (iii) amino acids 1-485 of SEQ ID NO: 7, or (iv) amino acids 1-485 of SEQ ID NO: 7 comprising the deletions T183*+G184*.

Embodiment 28

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 8, (ii) the mature polypeptide of SEQ ID NO: 8 comprising the deletions D183*+G184*, (iii) amino acids 1-485 of SEQ ID NO: 8, or (iv) amino acids 1-485 of SEQ ID NO: 8 comprising the deletions D183*+G184*.

Embodiment 29

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 9, (ii) the mature polypeptide of SEQ ID NO: 9 comprising the deletions D183*+G184*, (iii) amino acids 1-485 of SEQ ID NO: 9, or (iv) amino acids 1-485 of SEQ ID NO: 9 comprising the deletions D183*+G184*.

Embodiment 30

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 10, (ii) the mature polypeptide of SEQ ID NO: 10 comprising the deletions D183*+G184*, (iii) amino acids 1-485 of SEQ ID NO: 10, or (iv) amino acids 1-485 of SEQ ID NO: 10 comprising the deletions D183*+G184*.

Embodiment 31

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 11, (ii) the mature polypeptide of SEQ ID NO: 11 comprising the deletions H183*+G184*, (iii) amino acids 1-485 of SEQ ID NO: 11, or (iv) amino acids 1-485 of SEQ ID NO: 11 comprising the deletions H183*+G184*.

Embodiment 32

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 12, or (ii) amino acids 1-480 of SEQ ID NO: 12.

Embodiment 33

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 13, or (ii) amino acids 1-483 of SEQ ID NO: 13.

Embodiment 34

The variant of Embodiment 19, wherein the parent alpha-amylase has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to (i) the mature polypeptide of SEQ ID NO: 14, or (ii) amino acids 1-481 of SEQ ID NO: 14.

Embodiment 35

The variant of Embodiment 19, wherein the parent alpha-amylase comprises or consists of (i) the mature polypeptide of any of SEQ ID NOs: 1, 2, 3, 4, 5, 6, 7, 8, 9, 10, 11, 12, 13 or 14, or (ii) amino acids 1 to 483 of SEQ ID NO: 1, amino acids 1 to 483 of SEQ ID NO: 2, amino acids 1 to 485 of SEQ ID NO: 3, amino acids 1 to 482 of SEQ ID NO: 4, amino acids 1 to 484 of SEQ ID NO: 5, amino acids 1 to 483 of SEQ ID NO: 6, amino acids 1 to 485 of SEQ ID NO: 7, amino acids 1 to 485 of SEQ ID NO: 8, amino acids 1 to 485 of SEQ ID NO: 9, amino acids 1 to 485 of SEQ ID NO: 10, amino acids 1 to 485 of SEQ ID NO: 11, amino acids 1 to 480 of SEQ ID NO: 12, amino acids 1 to 483 of SEQ ID NO: 13 or amino acids 1 to 481 of SEQ ID NO: 14.

Embodiment 36

The variant of Embodiment 19, wherein the parent alpha-amylase is a fragment of the mature polypeptide of any of SEQ ID NOs: 1, 2, 3, 4, 5, 6, 7, 8, 9, 10, 11, 12, 13 or 14, wherein the fragment has alpha-amylase activity.

Embodiment 37

The variant of any of Embodiments 1 to 36, wherein the variant consists of 300 to 700, e.g., 350 to 650, 400 to 600, 450 to 500 or 470 to 490, amino acids.

Embodiment 38

The variant of any of Embodiments 1 to 37, which comprises an alteration at two or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1.

Embodiment 39

The variant of any of Embodiments 1 to 37, which comprises an alteration at three or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1.

Embodiment 40

The variant of any of Embodiments 1 to 37, which comprises an alteration at four or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1.

Embodiment 41

The variant of any of Embodiments 1 to 37, which comprises an alteration at five or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1.

Embodiment 42

The variant of any of Embodiments 1 to 37, which comprises an alteration at six or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1.

Embodiment 43

The variant of any of Embodiments 1 to 37, which comprises an alteration at two or more positions corresponding to any of positions 2, 68, 133, 142, 176, 185, 201, 205, 213, 360, 416 and 437 of SEQ ID NO: 1.

Embodiment 44

The variant of any of Embodiments 1 to 37, which comprises an alteration at three or more positions corresponding to any of positions 2, 68, 133, 142, 176, 185, 201, 205, 213, 360, 416 and 437 of SEQ ID NO: 1.

Embodiment 45

The variant of any of Embodiments 1 to 37, which comprises an alteration at four or more positions corresponding to any of positions 2, 68, 133, 142, 176, 185, 201, 205, 213, 360, 416 and 437 of SEQ ID NO: 1.

Embodiment 46

The variant of any of Embodiments 1 to 37, which comprises an alteration at five or more positions corresponding to any of positions 2, 68, 133, 142, 176, 185, 201, 205, 213, 360, 416 and 437 of SEQ ID NO: 1.

Embodiment 47

The variant of any of Embodiments 1 to 37, which comprises an alteration at six or more positions corresponding to any of positions 2, 68, 133, 142, 176, 185, 201, 205, 213, 360, 416 and 437 of SEQ ID NO: 1.

Embodiment 48

The variant of any of Embodiments 1 to 37, which comprises a substitution at two or more positions corresponding to any of positions 68, 176, 185, 201, 205, 213, 360, 416 and 437 of SEQ ID NO: 1.

Embodiment 49

The variant of any of Embodiments 1 to 37, which comprises a substitution at three or more positions corresponding to any of positions 68, 176, 185, 201, 205, 213, 360, 416 and 437 of SEQ ID NO: 1.

Embodiment 50

The variant of any of Embodiments 1 to 37, which comprises a substitution at four or more positions corresponding to any of positions 68, 176, 185, 201, 205, 213, 360, 416 and 437 of SEQ ID NO: 1.

Embodiment 51

The variant of any of Embodiments 1 to 37, which comprises a substitution at five or more positions corresponding to any of positions 68, 176, 185, 201, 205, 213, 360, 416 and 437 of SEQ ID NO: 1.

Embodiment 52

The variant of any of Embodiments 1 to 37, which comprises a substitution at six or more positions corresponding to any of positions 68, 176, 185, 201, 205, 213, 360, 416 and 437 of SEQ ID NO: 1.

Embodiment 53

The variant of any of Embodiments 1 to 37, which comprises one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 54

The variant of any of Embodiments 1 to 37, which comprises two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 55

The variant of any of Embodiments 1 to 37, which comprises three or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 56

The variant of any of Embodiments 1 to 37, which comprises four or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 57

The variant of any of Embodiments 1 to 37, which comprises five or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 58

The variant of any of Embodiments 1 to 37, which comprises six or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 59

The variant of any of Embodiments 1 to 37, which comprises one or more substitutions selected from the group consisting of N2H, H68W, H133Y, H142W, K176L, E185P, I201Y, H205Y, K213T, Q360S, D416V and R437W.

Embodiment 60

The variant of any of Embodiments 1 to 37, which comprises two or more substitutions selected from the group consisting of N2H, H68W, H133Y, H142W, K176L, E185P, I201Y, H205Y, K213T, Q360S, D416V and R437W.

Embodiment 61

The variant of any of Embodiments 1 to 37, which comprises three or more substitutions selected from the group consisting of N2H, H68W, H133Y, H142W, K176L, E185P, I201Y, H205Y, K213T, Q360S, D416V and R437W.

Embodiment 62

The variant of any of Embodiments 1 to 37, which comprises four or more substitutions selected from the group consisting of N2H, H68W, H133Y, H142W, K176L, E185P, I201Y, H205Y, K213T, Q360S, D416V and R437W.

Embodiment 63

The variant of any of Embodiments 1 to 37, which comprises five or more substitutions selected from the group consisting of N2H, H68W, H133Y, H142W, K176L, E185P, I201Y, H205Y, K213T, Q360S, D416V and R437W.

Embodiment 64

The variant of any of Embodiments 1 to 37, which comprises six or more substitutions selected from the group consisting of N2H, H68W, H133Y, H142W, K176L, E185P, I201Y, H205Y, K213T, Q360S, D416V and R437W.

Embodiment 65

The variant of any of Embodiments 1 to 37, which comprises one or more substitutions selected from the group consisting of H68W, K176L, E185P, I201Y, H205Y, K213T, Q360S, D416V and R437W.

Embodiment 66

The variant of any of Embodiments 1 to 37, which comprises two or more substitutions selected from the group consisting of H68W, K176L, E185P, I201Y, H205Y, K213T, Q360S, D416V and R437W.

Embodiment 67

The variant of any of Embodiments 1 to 37, which comprises three or more substitutions selected from the group consisting of H68W, K176L, E185P, I201Y, H205Y, K213T, Q360S, D416V and R437W.

Embodiment 68

The variant of any of Embodiments 1 to 37, which comprises four or more substitutions selected from the group consisting of H68W, K176L, E185P, I201Y, H205Y, K213T, Q360S, D416V and R437W.

Embodiment 69

The variant of any of Embodiments 1 to 37, which comprises five or more substitutions selected from the group consisting of H68W, K176L, E185P, I201Y, H205Y, K213T, Q360S, D416V and R437W.

Embodiment 70

The variant of any of Embodiments 1 to 37, which comprises six or more substitutions selected from the group consisting of H68W, K176L, E185P, I201Y, H205Y, K213T, Q360S, D416V and R437W.

Embodiment 71

The variant of any of Embodiments 1 to 37, which comprises an insertion at a position corresponding to position 1.

Embodiment 72

The variant of any of Embodiments 1 to 37, which comprises the insertion A1AH.

Embodiment 73

The variant of any of Embodiments 1 to 37, which comprises the insertion A1AW.

Embodiment 74

The variant of any of Embodiments 1 to 37, which comprises a substitution at a position corresponding to position 1.

Embodiment 75

The variant of any of Embodiments 1 to 37, which comprises the substitution A1H.

Embodiment 76

The variant of any of Embodiments 1 to 37, which comprises the substitution A1 W.

Embodiment 77

The variant of any of Embodiments 1 to 37, which comprises an insertion at a position corresponding to position 2.

Embodiment 78

The variant of any of Embodiments 1 to 37, which comprises the insertion N2NH.

Embodiment 79

The variant of any of Embodiments 1 to 37, which comprises the insertion N2NW

Embodiment 80

The variant of any of Embodiments 1 to 37, which comprises a substitution at a position corresponding to position 2.

Embodiment 81

The variant of any of Embodiments 1 to 37, which comprises the substitution N2H.

Embodiment 82

The variant of any of Embodiments 1 to 37, which comprises the substitution N2W.

Embodiment 83

The variant of any of Embodiments 1 to 37, which comprises a substitution at a position corresponding to position 68.

Embodiment 84

The variant of any of Embodiments 1 to 37, which comprises the substitution H68W.

Embodiment 85

The variant of any of Embodiments 1 to 37, which comprises a substitution at a position corresponding to position 71.

Embodiment 86

The variant of any of Embodiments 1 to 37, which comprises the substitution G71W.

Embodiment 87

The variant of any of Embodiments 1 to 37, which comprises a substitution at a position corresponding to position 126.

Embodiment 88

The variant of any of Embodiments 1 to 37, which comprises the substitution N126W.

Embodiment 89

The variant of any of Embodiments 1 to 37, which comprises a substitution at a position corresponding to position 133.

Embodiment 90

The variant of any of Embodiments 1 to 37, which comprises the substitution H133Y.

Embodiment 91

The variant of any of Embodiments 1 to 37, which comprises a substitution at a position corresponding to position 142.

Embodiment 92

The variant of any of Embodiments 1 to 37, which comprises the substitution H142W.

Embodiment 93

The variant of any of Embodiments 1 to 37, which comprises a substitution at a position corresponding to position 144.

Embodiment 94

The variant of any of Embodiments 1 to 37, which comprises the substitution P144W.

Embodiment 95

The variant of any of Embodiments 1 to 37, which comprises a substitution at a position corresponding to position 156.

Embodiment 96

The variant of any of Embodiments 1 to 37, which comprises the substitution Y156W.

Embodiment 97

The variant of any of Embodiments 1 to 37, which comprises a substitution at a position corresponding to position 158.

Embodiment 98

The variant of any of Embodiments 1 to 37, which comprises the substitution Y158W.

Embodiment 99

The variant of any of Embodiments 1 to 37, which comprises a substitution at a position corresponding to position 176.

Embodiment 100

The variant of any of Embodiments 1 to 37, which comprises the substitution K176L.

Embodiment 101

The variant of any of Embodiments 1 to 37, which comprises a substitution at a position corresponding to position 185.

Embodiment 102

The variant of any of Embodiments 1 to 37, which comprises the substitution E185P.

Embodiment 103

The variant of any of Embodiments 1 to 37, which comprises a substitution at a position corresponding to position 201.

Embodiment 104

The variant of any of Embodiments 1 to 37, which comprises the substitution I201Y.

Embodiment 105

The variant of any of Embodiments 1 to 37, which comprises a substitution at a position corresponding to position 205.

Embodiment 106

The variant of any of Embodiments 1 to 37, which comprises the substitution H205Y.

Embodiment 107

The variant of any of Embodiments 1 to 37, which comprises a substitution at a position corresponding to position 213.

Embodiment 108

The variant of any of Embodiments 1 to 37, which comprises the substitution K213T.

Embodiment 109

The variant of any of Embodiments 1 to 37, which comprises a substitution at a position corresponding to position 239.

Embodiment 110

The variant of any of Embodiments 1 to 37, which comprises the substitution S239A.

Embodiment 111

The variant of any of Embodiments 1 to 37, which comprises the substitution S239Q.

Embodiment 112

The variant of any of Embodiments 1 to 37, which comprises a substitution at a position corresponding to position 279.

Embodiment 113

The variant of any of Embodiments 1 to 37, which comprises the substitution F279W.

Embodiment 114

The variant of any of Embodiments 1 to 37, which comprises a substitution at a position corresponding to position 316.

Embodiment 115

The variant of any of Embodiments 1 to 37, which comprises the substitution H316W.

Embodiment 116

The variant of any of Embodiments 1 to 37, which comprises a substitution at a position corresponding to position 318.

Embodiment 117

The variant of any of Embodiments 1 to 37, which comprises the substitution L318W.

Embodiment 118

The variant of any of Embodiments 1 to 37, which comprises a substitution at a position corresponding to position 360.

Embodiment 119

The variant of any of Embodiments 1 to 37, which comprises the substitution Q360S.

Embodiment 120

The variant of any of Embodiments 1 to 37, which comprises a substitution at a position corresponding to position 416.

Embodiment 121

The variant of any of Embodiments 1 to 37, which comprises the substitution D416V.

Embodiment 122

The variant of any of Embodiments 1 to 37, which comprises a substitution at a position corresponding to position 437.

Embodiment 123

The variant of any of Embodiments 1 to 37, which comprises the substitution R437W.

Embodiment 124

The variant of any of Embodiments 1 to 37, which comprises a substitution at a position corresponding to position 450.

Embodiment 125

The variant of any of Embodiments 1 to 37, which comprises the substitution H450W.

Embodiment 126

The variant of any of Embodiment 1 to 37, which comprises a set of substitutions selected from the group consisting of:
A1H+N2H,
A1H+N2W,
A1H+H68W,
A1H+G71W,
A1H+N126W,
A1H+H133Y,
A1H+H142W,
A1H+P144W,
A1H+Y156W,
A1H+Y158W,
A1H+K176L,
A1H+E185P,
A1H+I201Y,
A1H+H205Y,
A1H+K213T,
A1H+S239A,
A1H+S239Q,
A1H+F279W,
A1H+H316W,
A1H+L318W,
A1H+Q360S,
A1H+D416V,
A1H+R437W,
A1H+H450W,
A1W+N2H,
A1W+N2W,
A1W+H68W,
A1W+G71W,
A1W+N126W,
A1W+H133Y,
A1W+H142W,
A1 W+P144W,
A1W+Y156W,
A1W+Y158W,
A1W+K176L,
A1W+E185P,
A1 W+I201Y,
A1 W+H205Y,
A1 W+K213T,
A1W+S239A,
A1W+S239Q,
A1W+F279W,
A1W+H316W,
A1W+L318W,
A1W+Q360S,
A1W+D416V,
A1W+R437W,
A1W+H450W,
N2H+H68W
N2H+G71W,
N2H+N126W,
N2H+H133Y,
N2H+H142W,
N2H+P144W,
N2H+Y156W,
N2H+Y158W,
N2H+K176L,
N2H+E185P,
N2H+I201Y,
N2H+H205Y,
N2H+K213T,
N2H+S239A,
N2H+S239Q,
N2H+F279W,
N2H+H316W,
N2H+L318W,
N2H+Q360S,
N2H+D416V,
N2H+R437W,
N2H+H450W,
N2W+H68W
N2W+G71W,
N2W+N126W,
N2W+H133Y,
N2W+H142W,
N2W+P144W,
N2W+Y156W,
N2W+Y158W,
N2W+K176L,
N2W+E185P,
N2W+I201Y,
N2W+H205Y,
N2W+K213T,
N2W+S239A,
N2W+S239Q,
N2W+F279W,
N2W+H316W,
N2W+L318W,
N2W+Q360S,
N2W+D416V,
N2W+R437W,
N2W+H450W,
H68W+G71W,
H68W+N126W,
H68W+H133Y,
H68W+H142W,
H68W+P144W,
H68W+Y156W,
H68W+Y158W,
H68W+K176L,
H68W+E185P,
H68W+I201Y,
H68W+H205Y,
H68W+K213T,
H68W+S239A,
H68W+S239Q,
H68W+F279W,
H68W+H316W,
H68W+L318W,
H68W+Q360S,
H68W+D416V,
H68W+R437W,
H68W+H450W,
G71W+N126W,
G71W+H133Y,
G71W+H142W,
G71W+P144W,
G71W+Y156W, G71W+Y158W,
G71W+K176L,
G71W+E185P,
G71W+I201Y,
G71W+H205Y,
G71W+K213T,
G71W+S239A,
G71W+S239Q,
G71W+F279W,
G71W+H316W,
G71W+L318W,
G71W+Q360S,
G71W+D416V,
G71W+R437W,
G71W+H450W,
N126W+H133Y,
N126W+H142W,
N126W+P144W,
N126W+Y156W,
N126W+Y158W,
N126W+K176L,
N126W+E185P,
N126W+I201Y,
N126W+H205Y,
N126W+K213T,
N126W+S239A,
N126W+S239Q,
N126W+F279W,
N126W+H316W,
N126W+L318W,
N126W+Q360S,
N126W+D416V,
N126W+R437W,
N126W+H450W,
H133Y+H142W,
H133Y+P144W,
H133Y+Y156W,
H133Y+Y158W,
H133Y+K176L,
H133Y+E185P,
H133Y+I201Y,
H133Y+H205Y,
H133Y+K213T,
H133Y+S239A,
H133Y+S239Q,
H133Y+F279W,
H133Y+H316W,
H133Y+L318W,
H133Y+Q360S,
H133Y+D416V,
H133Y+R437W,
H133Y+H450W,
H142W+P144W,
H142W+Y156W,
H142W+Y158W,
H142W+K176L,
H142W+E185P,
H142W+I201Y,
H142W+H205Y,
H142W+K213T,
H142W+S239A,
H142W+S239Q,
H142W+F279W,
H142W+H316W,
H142W+L318W,
H142W+Q360S,
H142W+D416V,
H142W+R437W,
H142W+H450W,
P144W+Y156W,
P144W+Y158W,
P144W+K176L,
P144W+E185P,
P144W+I201Y,
P144W+H205Y,
P144W+K213T,
P144W+S239A,
P144W+S239Q,
P144W+F279W,
P144W+H316W,
P144W+L318W,
P144W+Q360S,
P144W+D416V,
P144W+R437W,
P144W+H450W,
Y156W+Y158W,
Y156W+K176L,
Y156W+E185P,
Y156W+I201Y,
Y156W+H205Y,
Y156W+K213T,
Y156W+S239A,
Y156W+S239Q,
Y156W+F279W,
Y156W+H316W,
Y156W+L318W,
Y156W+Q360S,
Y156W+D416V,
Y156W+R437W,
Y156W+H450W,
Y158W+K176L,
Y158W+E185P,
Y158W+I201Y,
Y158W+H205Y,
Y158W+K213T,
Y158W+S239A,
Y158W+S239Q,
Y158W+F279W,
Y158W+H316W,
Y158W+L318W,
Y158W+Q360S,
Y158W+D416V,
Y158W+R437W,
Y158W+H450W,
K176L+E185P,
K176L+I201Y,
K176L+H205Y,
K176L+K213T,
K176L+S239A,
K176L+S239Q,
K176L+F279W,
K176L+H316W,
K176L+L318W,
K176L+Q360S,
K176L+D416V,
K176L+R437W,
K176L+H450W,
E185P+I201Y,
E185P+H205Y,
E185P+K213T,
E185P+S239A,
E185P+S239Q,
E185P+F279W,
E185P+H316W, E185P+L318W,
E185P+Q360S,
E185P+D416V,
E185P+R437W,
E185P+H450W,
I201Y+H205Y,
I201Y+K213T,
I201Y+S239A,
I201Y+S239Q,
I201Y+F279W,
I201Y+H316W,
I201Y+L318W,
I201Y+Q360S,
I201Y+D416V,
I201Y+R437W,
I201Y+H450W,
H205Y+K213T,
H205Y+S239A,
H205Y+S239Q,
H205Y+F279W,
H205Y+H316W,
H205Y+L318W,
H205Y+Q360S,
H205Y+D416V,
H205Y+R437W,
H205Y+H450W,
K213T+S239A,
K213T+S239Q,
K213T+F279W,
K213T+H316W,
K213T+L318W,
K213T+Q360S,
K213T+D416V,
K213T+R437W,
K213T+H450W,
S239A+F279W,
S239A+H316W,
S239A+L318W,
S239A+Q360S,
S239A+D416V,
S239A+R437W,
S239A+H450W,
S239Q+F279W,
S239Q+H316W,
S239Q+L318W,
S239Q+Q360S,
S239Q+D416V,
S239Q+R437W,
S239Q+H450W,
F279W+H316W,
F279W+L318W,
F279W+Q360S,
F279W+D416V,
F279W+R437W,
F279W+H450W,
H316W+L318W,
H316W+Q360S,
H316W+D416V,
H316W+R437W,
H316W+H450W,
L318W+Q360S,
L318W+D416V,
L318W+R437W,
L318W+H450W,
Q360S+D416V,
Q360S+R437W,
Q360S+H450W,
D416V+R437W,
D416V+H450W, and
R437W+H450W.

Embodiment 127

The variant of any of Embodiments 1 to 37, which comprises an alteration at a position corresponding to position 1, in particular the insertion A1AH or A1AW or the substitution A1H or A1 W, in combination with an alteration at one or more positions corresponding to any of positions 2, 68, 71, 126, 133, 142, 144, 156, 158, 176, 185, 201, 205, 213, 239, 279, 316, 318, 360, 416, 437 and 450, in particular one or more alterations selected from the group consisting of N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 128

The variant of any of Embodiments 1 to 37, which comprises an alteration at a position corresponding to position 1, in particular the insertion A1AH or A1AW or the substitution A1H or A1 W, in combination with an alteration at two or more positions corresponding to any of positions 2, 68, 71, 126, 133, 142, 144, 156, 158, 176, 185, 201, 205, 213, 239, 279, 316, 318, 360, 416, 437 and 450, in particular two or more alterations selected from the group consisting of N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 129

The variant of any of Embodiments 1 to 37, which comprises an alteration at a position corresponding to position 2, in particular the insertion N2NH or N2NW or the substitution N2H or N2W, preferably the substitution N2H, in combination with an alteration at one or more positions corresponding to any of positions 1, 68, 71, 126, 133, 142, 144, 156, 158, 176, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 130

The variant of any of Embodiments 1 to 37, which comprises an alteration at a position corresponding to position 2, in particular the insertion N2NH or N2NW or the substitution N2H or N2W, preferably the substitution N2H, in combination with a substitution at one or more positions corresponding to any of positions 68, 176, 185, 201, 205, 213, 360, 416 and 437, in particular one or more substitutions selected from the group consisting of H68W, K176L, E185P, I201Y, H205Y, K213T, Q360S, D416V and R437W.

Embodiment 131

The variant of any of Embodiments 1 to 37, which comprises an alteration at a position corresponding to position 2, in particular the insertion N2NH or N2NW or the substitution N2H or N2W, preferably the substitution N2H, in combination with a substitution at one or more positions corresponding to any of positions 68, 133, 142, 156, 158, 279 and 437, in particular one or more substitutions selected from the group consisting of H68W, H133Y, H142W, Y156W, Y158W, F279W and R437W.

Embodiment 132

The variant of any of Embodiments 1 to 37, which comprises an alteration at a position corresponding to position 2, in particular the insertion N2NH or N2NW or the substitution N2H or N2W, preferably the substitution N2H, in combination with an alteration at two or more positions corresponding to any of positions 1, 68, 71, 126, 133, 142, 144, 156, 158, 176, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, H68W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 133

The variant of any of Embodiments 1 to 37, which comprises an alteration at a position corresponding to position 2, in particular the insertion N2NH or N2NW or the substitution N2H or N2W, preferably the substitution N2H, in combination with a substitution at two or more positions corresponding to any of positions 68, 176, 185, 201, 205, 213, 360, 416 and 437, in particular two or more substitutions selected from the group consisting of H68W, K176L, E185P, I201Y, H205Y, K213T, Q360S, D416V and R437W.

Embodiment 134

The variant of any of Embodiments 1 to 37, which comprises an alteration at a position corresponding to position 2, in particular the insertion N2NH or N2NW or the substitution N2H or N2W, preferably the substitution N2H, in combination with a substitution at two or more positions corresponding to any of positions 68, 133, 142, 156, 158, 279 and 437, in particular two or more substitutions selected from the group consisting of H68W, H133Y, H142W, Y156W, Y158W, F279W and R437W.

Embodiment 135

The variant of any of Embodiments 1 to 37, which comprises a substitution at a position corresponding to position 68, in particular the substitution H68W, in combination with an alteration at one or more positions corresponding to any of positions 1, 2, 71, 126, 133, 142, 144, 156, 158, 176, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 136

The variant of any of Embodiments 1 to 37, which comprises a substitution at a position corresponding to position 68, in particular the substitution H68W, in combination with a substitution at one or more positions corresponding to any of positions 176, 185, 201, 205, 213, 360, 416 and 437, in particular one or more substitutions selected from the group consisting of K176L, E185P, I201Y, H205Y, K213T, Q360S, D416V and R437W.

Embodiment 137

The variant of any of Embodiments 1 to 37, which comprises a substitution at a position corresponding to position 68, in particular the substitution H68W, in combination with a substitution at one or more positions corresponding to any of positions 2, 133, 142, 156, 158, 279 and 437, in particular one or more substitutions selected from the group consisting of N2H, H133Y, H142W, Y156W, Y158W, F279W and R437W.

Embodiment 138

The variant of any of Embodiments 1 to 37, which comprises a substitution at a position corresponding to position 68, in particular the substitution H68W, in combination with an alteration at two or more positions corresponding to any of positions 1, 2, 71, 126, 133, 142, 144, 156, 158, 176, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 139

The variant of any of Embodiments 1 to 37, which comprises a substitution at a position corresponding to position 68, in particular the substitution H68W, in combination with a substitution at two or more positions corresponding to any of positions 176, 185, 201, 205, 213, 360, 416 and 437, in particular two or more substitutions selected from the group consisting of K176L, E185P, I201Y, H205Y, K213T, Q360S, D416V and R437W.

Embodiment 140

The variant of any of Embodiments 1 to 37, which comprises a substitution at a position corresponding to position 68, in particular the substitution H68W, in combination with a substitution at two or more positions corresponding to any of positions 2, 133, 142, 156, 158, 279 and 437, in particular two or more substitutions selected from the group consisting of N2H, H133Y, H142W, Y156W, Y158W, F279W and R437W.

Embodiment 141

The variant of any of Embodiments 1 to 37, which comprises a substitution at a position corresponding to position 71, in particular the substitution G71W, in combination with a substitution at one or more positions corresponding to any of positions 1, 2, 68, 126, 133, 142, 144, 156, 158, 176, 185, 201, 205, 213, 239, 279, 316, 318, 360, 416, 437 and 450, in particular one or more substitutions selected from the group consisting of A1H, A1 W, N2H, N2W, H68W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 142

The variant of any of Embodiments 1 to 37, which comprises a substitution at a position corresponding to position 71, in particular the substitution G71W, in combination with a substitution at two or more positions corresponding to any of positions 1, 2, 68, 126, 133, 142, 144, 156, 158, 176, 185, 201, 205, 213, 239, 279, 316, 318, 360, 416, 437 and 450, in particular two or more substitutions selected from the group consisting of A1H, A1 W, N2H, N2W, H68W, N126W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 143

The variant of any of Embodiments 1 to 37, which comprises a substitution at a position corresponding to position 126, in particular the substitution N126W, in combination with a substitution at one or more positions corresponding to any of positions 1, 2, 68, 71, 133, 142, 144, 156, 158, 176, 185, 201, 205, 213, 239, 279, 316, 318, 360, 416, 437 and 450, in particular one or more substitutions selected from the group consisting of A1H, A1 W, N2H, N2W, H68W, G71W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 144

The variant of any of Embodiments 1 to 37, which comprises a substitution at a position corresponding to position 126, in particular the substitution N126W, in combination with a substitution at two or more positions corresponding to any of positions 1, 2, 68, 71, 133, 142, 144, 156, 158, 176, 185, 201, 205, 213, 239, 279, 316, 318, 360, 416, 437 and 450, in particular two or more substitutions selected from the group consisting of A1H, A1W, N2H, N2W, H68W, G71W, H133Y, H142W, P144W, Y156W, Y158W, K176L, E185P, I201Y, H205Y, K213T, S239A, S239Q, F279W, H316W, L318W, Q360S, D416V, R437W and H450W.

Embodiment 145

The variant of any of Embodiments 1 to 37, which comprises a substitution at a position corresponding to position 133, in particular the substitution H133Y, in combination with an alteration at one or more positions corresponding to any of positions 1, 2, 68, 71, 126, 142, 144, 156, 158, 176, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H142W, P144W, Y156W, Y158W, K176L, E185P, I201Y, H205Y, K213T, S239A, S239Q, F279W, H316W, L318W, Q360S, D416V, R437W and H450W.

Embodiment 146

The variant of any of Embodiments 1 to 37, which comprises a substitution at a position corresponding to position 133, in particular the substitution H133Y, in combination with a substitution at one or more positions corresponding to any of positions 68, 176, 185, 201, 205, 213, 360, 416 and 437, in particular one or more substitutions selected from the group consisting of H68W, K176L, E185P, I201Y, H205Y, K213T, Q360S, D416V and R437W.

Embodiment 147

The variant of any of Embodiments 1 to 37, which comprises a substitution at a position corresponding to position 133, in particular the substitution H133Y, in combination with a substitution at one or more positions corresponding to any of positions 2, 68, 142, 156, 158, 279 and 437, in particular one or more substitutions selected from the group consisting of N2H, H68W, H142W, Y156W, Y158W, F279W and R437W.

Embodiment 148

The variant of any of Embodiments 1 to 37, which comprises a substitution at a position corresponding to

89 position 133, in particular the substitution H133Y, in combination with an alteration at two or more positions corresponding to any of positions 1, 2, 68, 71, 126, 142, 144, 156, 158, 176, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H142W, P144W, Y156W, Y158W, K176L, E185P, I201Y, H205Y, K213T, S239A, S239Q, F279W, H316W, L318W, Q360S, D416V, R437W and H450W.

Embodiment 149

The variant of any of Embodiments 1 to 37, which comprises a substitution at a position corresponding to position 133, in particular the substitution H133Y, in combination with a substitution at two or more positions corresponding to any of positions 68, 176, 185, 201, 205, 213, 360, 416 and 437, in particular two or more substitutions selected from the group consisting of H68W, K176L, E185P, I201Y, H205Y, K213T, Q360S, D416V and R437W.

Embodiment 150

The variant of any of Embodiments 1 to 37, which comprises a substitution at a position corresponding to position 133, in particular the substitution H133Y, in combination with a substitution at two or more positions corresponding to any of positions 2, 68, 142, 156, 158, 279 and 437, in particular two or more substitutions selected from the group consisting of N2H, H68W, H142W, Y156W, Y158W, F279W and R437W.

Embodiment 151

The variant of any of Embodiments 1 to 37, which comprises a substitution at a position corresponding to position 142, in particular the substitution H142W, in combination with an alteration at one or more positions corresponding to any of positions 1, 2, 68, 71, 126, 133, 144, 156, 158, 176, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, P144W, Y156W, Y158W, K176L, E185P, I201Y, H205Y, K213T, S239A, S239Q, F279W, H316W, L318W, Q360S, D416V, R437W and H450W.

90

Embodiment 152

The variant of any of Embodiments 1 to 37, which comprises a substitution at a position corresponding to position 142, in particular the substitution H142W, in combination with a substitution at one or more positions corresponding to any of positions 68, 176, 185, 201, 205, 213, 360, 416 and 437, in particular one or more substitutions selected from the group consisting of H68W, K176L, E185P, I201Y, H205Y, K213T, Q360S, D416V and R437W.

Embodiment 153

The variant of any of Embodiments 1 to 37, which comprises a substitution at a position corresponding to position 142, in particular the substitution H142W, in combination with a substitution at one or more positions corresponding to any of positions 2, 68, 133, 156, 158, 279 and 437, in particular one or more substitutions selected from the group consisting of N2H, H68W, H133Y, Y156W, Y158W, F279W and R437W.

Embodiment 154

The variant of any of Embodiments 1 to 37, which comprises a substitution at a position corresponding to position 142, in particular the substitution H142W, in combination with an alteration at two or more positions corresponding to any of positions 1, 2, 68, 71, 126, 133, 144, 156, 158, 176, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, P144W, Y156W, Y158W, K176L, E185P, I201Y, H205Y, K213T, S239A, S239Q, F279W, H316W, L318W, Q360S, D416V, R437W and H450W.

Embodiment 155

The variant of any of Embodiments 1 to 37, which comprises a substitution at a position corresponding to position 142, in particular the substitution H142W, in combination with a substitution at two or more positions corresponding to any of positions 68, 176, 185, 201, 205, 213, 360, 416 and 437, in particular two or more substitutions selected from the group consisting of H68W, K176L, E185P, I201Y, H205Y, K213T, Q360S, D416V and R437W.

Embodiment 156

The variant of any of Embodiments 1 to 37, which comprises a substitution at a position corresponding to position 142, in particular the substitution H142W, in combination with a substitution at two or more positions corresponding to any of positions 2, 68, 133, 156, 158, 279 and 437, in particular two or more substitutions selected from the group consisting of N2H, H68W, H133Y, Y156W, Y158W, F279W and R437W.

Embodiment 157

The variant of any of Embodiments 1 to 37, which comprises a substitution at a position corresponding to position 144, in particular the substitution P144W, in combination with a substitution at one or more positions corresponding to any of positions 1, 2, 68, 71, 126, 133, 142, 156, 158, 176, 185, 201, 205, 213, 239, 279, 316, 318, 360, 416, 437 and 450, in particular one or more substitutions selected from the group consisting of A1H, A1 W, N2H, N2W, H68W, G71W, N126W, H133Y, H142W, Y156W, Y158W, K176L, E185P, I201Y, H205Y, K213T, S239A, S239Q, F279W, H316W, L318W, Q360S, D416V, R437W and H450W.

Embodiment 158

The variant of any of Embodiments 1 to 37, which comprises a substitution at a position corresponding to position 144, in particular the substitution P144W, in combination with a substitution at two or more positions corresponding to any of positions 1, 2, 68, 71, 126, 133, 142, 156, 158, 176, 185, 201, 205, 213, 239, 279, 316, 318, 360, 416, 437 and 450, in particular two or more substitutions selected from the group consisting of A1H, A1 W, N2H, N2W, H68W, G71W, N126W, H133Y, H142W, Y156W, Y158W, K176L, E185P, I201Y, H205Y, K213T, S239A, S239Q, F279W, H316W, L318W, Q360S, D416V, R437W and H450W.

Embodiment 159

The variant of any of Embodiments 1 to 37, which comprises a substitution at a position corresponding to position 156, in particular the substitution Y156W, in combination with an alteration at one or more positions corresponding to any of positions 1, 2, 68, 71, 126, 133, 142, 144, 158, 176, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y158W, K176L, E185P, I201Y, H205Y, K213T, S239A, S239Q, F279W, H316W, L318W, Q360S, D416V, R437W and H450W.

Embodiment 160

The variant of any of Embodiments 1 to 37, which comprises a substitution at a position corresponding to position 156, in particular the substitution Y156W, in combination with a substitution at one or more positions corresponding to any of positions 68, 176, 185, 201, 205, 213, 360, 416 and 437, in particular one or more substitutions selected from the group consisting of H68W, K176L, E185P, I201Y, H205Y, K213T, Q360S, D416V and R437W.

Embodiment 161

The variant of any of Embodiments 1 to 37, which comprises a substitution at a position corresponding to position 156, in particular the substitution Y156W, in combination with a substitution at one or more positions corresponding to any of positions 2, 68, 133, 142, 158, 279 and 437, in particular one or more substitutions selected from the group consisting of N2H, H68W, H133Y, H142W, Y158W, F279W and R437W.

Embodiment 162

The variant of any of Embodiments 1 to 37, which comprises a substitution at a position corresponding to position 156, in particular the substitution Y156W, in combination with an alteration at two or more positions corresponding to any of positions 1, 2, 68, 71, 126, 133, 142, 144, 158, 176, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y158W, K176L, E185P, I201Y, H205Y, K213T, S239A, S239Q, F279W, H316W, L318W, Q360S, D416V, R437W and H450W.

Embodiment 163

The variant of any of Embodiments 1 to 37, which comprises a substitution at a position corresponding to position 156, in particular the substitution Y156W, in combination with a substitution at two or more positions corresponding to any of positions 68, 176, 185, 201, 205, 213, 360, 416 and 437, in particular two or more substitutions selected from the group consisting of H68W, K176L, E185P, I201Y, H205Y, K213T, Q360S, D416V and R437W.

Embodiment 164

The variant of any of Embodiments 1 to 37, which comprises a substitution at a position corresponding to position 156, in particular the substitution Y156W, in combination with a substitution at two or more positions corresponding to any of positions 2, 68, 133, 142, 158, 279 and 437, in particular two or more substitutions selected from the group consisting of N2H, H68W, H133Y, H142W, Y158W, F279W and R437W.

Embodiment 165

The variant of any of Embodiments 1 to 37, which comprises a substitution at a position corresponding to position 158, in particular the substitution Y158W, in combination with an alteration at one or more positions corresponding to any of positions 1, 2, 68, 71, 126, 133, 142, 144, 156, 176, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, K176L, E185P, I201Y, H205Y, K213T, S239A, S239Q, F279W, H316W, L318W, Q360S, D416V, R437W and H450W.

Embodiment 166

The variant of any of Embodiments 1 to 37, which comprises a substitution at a position corresponding to position 158, in particular the substitution Y158W, in combination with a substitution at one or more positions corresponding to any of positions 68, 176, 185, 201, 205, 213, 360, 416 and 437, in particular one or more substitutions selected from the group consisting of H68W, K176L, E185P, I201Y, H205Y, K213T, Q360S, D416V and R437W.

Embodiment 167

The variant of any of Embodiments 1 to 37, which comprises a substitution at a position corresponding to position 158, in particular the substitution Y158W, in combination with a substitution at one or more positions corresponding to any of positions 2, 68, 133, 142, 156, 279 and 437, in particular one or more substitutions selected from the group consisting of N2H, H68W, H133Y, H142W, Y156W, F279W and R437W.

Embodiment 168

The variant of any of Embodiments 1 to 37, which comprises a substitution at a position corresponding to position 158, in particular the substitution Y158W, in combination with an alteration at two or more positions corresponding to any of positions 1, 2, 68, 71, 126, 133, 142, 144, 156, 176, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, K176L, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, K176L, E185P, I201Y, H205Y, K213T, S239A, S239Q, F279W, H316W, L318W, Q360S, D416V, R437W and H450W.

Embodiment 169

The variant of any of Embodiments 1 to 37, which comprises a substitution at a position corresponding to position 158, in particular the substitution Y158W, in combination with a substitution at two or more positions corresponding to any of positions 68, 176, 185, 201, 205, 213, 360, 416 and 437, in particular two or more substitutions selected from the group consisting of H68W, K176L, E185P, I201Y, H205Y, K213T, Q360S, D416V and R437W.

Embodiment 170

The variant of any of Embodiments 1 to 37, which comprises a substitution at a position corresponding to position 158, in particular the substitution Y158W, in combination with a substitution at two or more positions corresponding to any of positions 2, 68, 133, 142, 156, 279 and 437, in particular two or more substitutions selected from the group consisting of N2H, H68W, H133Y, H142W, Y156W, F279W and R437W.

Embodiment 171

The variant of any of Embodiments 1 to 37, which comprises a substitution at a position corresponding to position 176, in particular the substitution K176L, in combination with an alteration at one or more positions corresponding to any of positions 1, 2, 68, 71, 126, 133, 142, 144, 156, 158, 185, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W.

Embodiment 172

The variant of any of Embodiments 1 to 37, which comprises a substitution at a position corresponding to position 176, in particular the substitution K176L, in combination with a substitution at one or more positions corresponding to any of positions 68, 185, 201, 205, 213, 360, 416 and 437, in particular one or more substitutions selected from the group consisting of H68W, E185P, I201Y, H205Y, K213T, Q360S, D416V and R437W.

Embodiment 173

The variant of any of Embodiments 1 to 37, which comprises a substitution at a position corresponding to position 176, in particular the substitution K176L, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 174

The variant of any of Embodiments 1 to 37, which comprises a substitution at a position corresponding to position 176, in particular the substitution K176L, in combination with an alteration at two or more positions corresponding to any of positions 1, 2, 68, 71, 126, 133, 142, 144, 156, 158, 185, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, E185P, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V, R437W and H450W.

Embodiment 175

The variant of any of Embodiments 1 to 37, which comprises a substitution at a position corresponding to position 176, in particular the substitution K176L, in combination with a substitution at two or more positions corresponding to any of positions 68, 185, 201, 205, 213, 360, 416 and 437, in particular two or more substitutions selected from the group consisting of H68W, E185P, I201Y, H205Y, K213T, Q360S, D416V and R437W.

Embodiment 176

The variant of any of Embodiments 1 to 37, which comprises a substitution at a position corresponding to position 176, in particular the substitution K176L, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 177

The variant of any of Embodiments 1 to 37, which comprises a substitution at a position corresponding to position 185, in particular the substitution E185P, in combination with an alteration at one or more positions corresponding to any of positions 1, 2, 68, 71, 126, 133, 142, 144, 156, 158, 176, 201, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W.

Embodiment 178

The variant of any of Embodiments 1 to 37, which comprises a substitution at a position corresponding to position 185, in particular the substitution E185P, in combination with a substitution at one or more positions corresponding to any of positions 68, 176, 201, 205, 213, 360, 416 and 437, in particular one or more substitutions selected from the group consisting of H68W, K176L, I201Y, H205Y, K213T, Q360S, D416V and R437W.

Embodiment 179

The variant of any of Embodiments 1 to 37, which comprises a substitution at a position corresponding to position 185, in particular the substitution E185P, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 180

The variant of any of Embodiments 1 to 37, which comprises a substitution at a position corresponding to position 185, in particular the substitution E185P, in combination with an alteration at two or more positions corresponding to any of positions 1, 2, 68, 71, 126, 133, 142, 144, 156, 158, 176, 201, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, I201F, I201Y, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V, R437W and H450W.

Embodiment 181

The variant of any of Embodiments 1 to 37, which comprises a substitution at a position corresponding to position 185, in particular the substitution E185P, in combination with a substitution at two or more positions corresponding to any of positions 68, 176, 201, 205, 213, 360, 416 and 437, in particular two or more substitutions selected from the group consisting of H68W, K176L, I201Y, H205Y, K213T, Q360S, D416V and R437W.

Embodiment 182

The variant of any of Embodiments 1 to 37, which comprises a substitution at a position corresponding to position 185, in particular the substitution E185P, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 183

The variant of any of Embodiments 1 to 37, which comprises a substitution at a position corresponding to position 201, in particular the substitution I201Y, in combination with an alteration at one or more positions corresponding to any of positions 1, 2, 68, 71, 126, 133, 142, 144, 156, 158, 176, 185, 205, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V, R437W and H450W.

Embodiment 184

The variant of any of Embodiments 1 to 37, which comprises a substitution at a position corresponding to position 201, in particular the substitution I201Y, in combination with a substitution at one or more positions corresponding to any of positions 68, 176, 185, 205, 213, 360, 416 and 437, in particular one or more substitutions selected from the group consisting of H68W, K176L, E185P, H205Y, K213T, Q360S, D416V and R437W.

Embodiment 185

The variant of any of Embodiments 1 to 37, which comprises a substitution at a position corresponding to position 201, in particular the substitution I201Y, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 186

The variant of any of Embodiments 1 to 37, which comprises a substitution at a position corresponding to position 201, in particular the substitution I201Y, in combination with an alteration at two or more positions corresponding to any of positions 1, 2, 68, 71, 126, 133, 142, 144, 156, 158, 176, 185, 205, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, H205Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V, R437W and H450W.

Embodiment 187

The variant of any of Embodiments 1 to 37, which comprises a substitution at a position corresponding to position 201, in particular the substitution I201Y, in combination with a substitution at two or more positions corresponding to any of positions 68, 176, 185, 205, 213, 360, 416 and 437, in particular two or more substitutions selected from the group consisting of H68W, K176L, E185P, H205Y, K213T, Q360S, D416V and R437W.

Embodiment 188

The variant of any of Embodiments 1 to 37, which comprises a substitution at a position corresponding to position 201, in particular the substitution I201Y, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 189

The variant of any of Embodiments 1 to 37, which comprises a substitution at a position corresponding to position 205, in particular the substitution H205Y, in combination with an alteration at one or more positions corresponding to any of positions 1, 2, 68, 71, 126, 133, 142, 144, 156, 158, 176, 185, 201, 213, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V, R437W and H450W.

Embodiment 190

The variant of any of Embodiments 1 to 37, which comprises a substitution at a position corresponding to position 205, in particular the substitution H205Y, in combination with a substitution at one or more positions corresponding to any of positions 68, 176, 185, 201, 213, 360, 416 and 437, in particular one or more substitutions selected from the group consisting of H68W, K176L, E185P, I201Y, K213T, Q360S, D416V and R437W.

Embodiment 191

The variant of any of Embodiments 1 to 37, which comprises a substitution at a position corresponding to position 205, in particular the substitution H205Y, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 192

The variant of any of Embodiments 1 to 37, which comprises a substitution at a position corresponding to position 205, in particular the substitution H205Y, in combination with an alteration at two or more positions corresponding to any of positions 1, 2, 68, 71, 126, 133, 142, 144, 156, 158, 176, 185, 201, 213, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, K213T, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V, R437W and H450W.

Embodiment 193

The variant of any of Embodiments 1 to 37, which comprises a substitution at a position corresponding to position 205, in particular the substitution H205Y, in combination with a substitution at two or more positions corresponding to any of positions 68, 176, 185, 201, 213, 360, 416 and 437, in particular two or more substitutions selected from the group consisting of H68W, K176L, E185P, I201Y, K213T, Q360S, D416V and R437W.

Embodiment 194

The variant of any of Embodiments 1 to 37, which comprises a substitution at a position corresponding to position 205, in particular the substitution H205Y, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 195

The variant of any of Embodiments 1 to 37, which comprises a substitution at a position corresponding to position 213, in particular the substitution K213T, in combination with an alteration at one or more positions corresponding to any of positions 1, 2, 68, 71, 126, 133, 142, 144, 156, 158, 176, 185, 201, 205, 239, 279, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V, R437W and H450W.

Embodiment 196

The variant of any of Embodiments 1 to 37, which comprises a substitution at a position corresponding to position 213, in particular the substitution K213T, in combination with a substitution at one or more positions corresponding to any of positions 68, 176, 185, 201, 205, 360, 416 and 437, in particular one or more substitutions selected from the group consisting of H68W, K176L, E185P, I201Y, H205Y, Q360S, D416V and R437W.

Embodiment 197

The variant of any of Embodiments 1 to 37, which comprises a substitution at a position corresponding to position 213, in particular the substitution K213T, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 198

The variant of any of Embodiments 1 to 37, which comprises a substitution at a position corresponding to position 213, in particular the substitution K213T, in combination with an alteration at two or more positions corresponding to any of positions 1, 2, 68, 71, 126, 133, 142, 144, 156, 158, 176, 185, 201, 205, 239, 279, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, S239A, S239Q, F279Y, F279W, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V, R437W and H450W.

Embodiment 199

The variant of any of Embodiments 1 to 37, which comprises a substitution at a position corresponding to position 213, in particular the substitution K213T, in combination with a substitution at two or more positions corresponding to any of positions 68, 176, 185, 201, 205, 360, 416 and 437, in particular two or more substitutions selected from the group consisting of H68W, K176L, E185P, I201Y, H205Y, Q360S, D416V and R437W.

Embodiment 200

The variant of any of Embodiments 1 to 37, which comprises a substitution at a position corresponding to position 213, in particular the substitution K213T, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 201

The variant of any of Embodiments 1 to 37, which comprises a substitution at a position corresponding to position 239, in particular the substitution S239A or S239Q, in combination with a substitution at one or more positions corresponding to any of positions 1, 2, 68, 71, 126, 133, 142, 144, 156, 158, 176, 185, 201, 205, 213, 279, 316, 318, 360, 416, 437 and 450, in particular one or more substitutions selected from the group consisting of A1H, A1 W, N2H, N2W, H68W, G71W, N126W, H133Y, H142W, P144W, Y156W, Y158W, K176L, E185P, I201Y, H205Y, K213T, F279W, H316W, L318W, Q360S, D416V, R437W and H450W.

Embodiment 202

The variant of any of Embodiments 1 to 37, which comprises a substitution at a position corresponding to position 239, in particular the substitution S239A or S239Q, in combination with a substitution at two or more positions corresponding to any of positions 1, 2, 68, 71, 126, 133, 142, 144, 156, 158, 176, 185, 201, 205, 213, 279, 316, 318, 360, 416, 437 and 450, in particular two or more substitutions selected from the group consisting of A1H, A1 W, N2H, N2W, H68W, G71W, N126W, H133Y, H142W, P144W, Y156W, Y158W, K176L, E185P, I201Y, H205Y, K213T, F279W, H316W, L318W, Q360S, D416V, R437W and H450W.

Embodiment 203

The variant of any of Embodiments 1 to 37, which comprises a substitution at a position corresponding to position 279, in particular the substitution F279W, in combination with an alteration at one or more positions corresponding to any of positions 1, 2, 68, 71, 126, 133, 142, 144, 156, 158, 176, 185, 201, 205, 213, 239, 316, 318, 360, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, H316F, H316Y, H316W, L318F, L318H, L318Y, L318W, Q360S, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, H316W, L318W, Q360S, D416V, R437W and H450W.

Embodiment 204

The variant of any of Embodiments 1 to 37, which comprises a substitution at a position corresponding to position 279, in particular the substitution F279W, in combination with a substitution at one or more positions corresponding to any of positions 68, 176, 185, 201, 205, 213, 360, 416 and 437, in particular one or more substitutions selected from the group consisting of H68W, K176L, E185P, I201Y, H205Y, K213T, Q360S, D416V and R437W.

Embodiment 205

The variant of any of Embodiments 1 to 37, which comprises a substitution at a position corresponding to position 279, in particular the substitution F279W, in combination with a substitution at one or more positions corresponding to any of positions 2, 68, 133, 142, 156, 158 and 437, in particular one or more substitutions selected from the group consisting of N2H, H68W, H133Y, H142W, Y156W, Y158W, and R437W.

Embodiment 206

The variant of any of Embodiments 1 to 37, which comprises a substitution at a position corresponding to position 279, in particular the substitution F279W, in combination with an alteration at two or more positions corresponding to any of positions 1, 2, 68, 71, 126, 133, 142, 144, 156, 158, 176, 185, 201, 205, 213, 239, 316, 318, 360, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, H316F, H316Y, H316W, L318F, L318H, L318Y, L318W, Q360S, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, H316W, L318W, Q360S, D416V, R437W and H450W.

Embodiment 207

The variant of any of Embodiments 1 to 37, which comprises a substitution at a position corresponding to position 279, in particular the substitution F279W, in combination with a substitution at two or more positions corresponding to any of positions 68, 176, 185, 201, 205, 213, 360, 416 and 437, in particular two or more substitutions selected from the group consisting of H68W, K176L, E185P, I201Y, H205Y, K213T, Q360S, D416V and R437W.

Embodiment 208

The variant of any of Embodiments 1 to 37, which comprises a substitution at a position corresponding to position 279, in particular the substitution F279W, in combination with a substitution at two or more positions corresponding to any of positions 2, 68, 133, 142, 156, 158 and 437, in particular two or more substitutions selected from the group consisting of N2H, H68W, H133Y, H142W, Y156W, Y158W and R437W.

Embodiment 209

The variant of any of Embodiments 1 to 37, which comprises a substitution at a position corresponding to position 316, in particular the substitution H316W, in combination with a substitution at one or more positions corresponding to any of positions 1, 2, 68, 71, 126, 133, 142, 144, 156, 158, 176, 185, 201, 205, 213, 239, 279, 318, 360, 416, 437 and 450, in particular one or more substitutions selected from the group consisting of A1H, A1 W, N2H, N2W, H68W, G71W, N126W, H133Y, H142W, P144W, Y156W, Y158W, K176L, E185P, I201Y, H205Y, K213T, S239A, S239Q, F279W, L318W, Q360S, D416V, R437W and H450W.

Embodiment 210

The variant of any of Embodiments 1 to 37, which comprises a substitution at a position corresponding to position 316, in particular the substitution H316W, in combination with a substitution at two or more positions corresponding to any of positions 1, 2, 68, 71, 126, 133, 142, 144, 156, 158, 176, 185, 201, 205, 213, 239, 279, 318, 360, 416, 437 and 450, in particular two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, L318W, Q360S, D416V, R437W and H450W.

Embodiment 211

The variant of any of Embodiments 1 to 37, which comprises a substitution at a position corresponding to position 318, in particular the substitution L318W, in combination with a substitution at one or more positions corresponding to any of positions 1, 2, 68, 71, 126, 133, 142, 144, 156, 158, 176, 185, 201, 205, 213, 239, 279, 316, 360, 416, 437 and 450, in particular one or more substitutions selected from the group consisting of A1H, A1 W, N2H, N2W, H68W, G71W, N126W, H133Y, H142W, P144W, Y156W, Y158W, K176L, E185P, I201Y, H205Y, K213T, S239A, S239Q, F279W, H316W, Q360S, D416V, R437W and H450W.

Embodiment 212

The variant of any of Embodiments 1 to 37, which comprises a substitution at a position corresponding to position 318, in particular the substitution L318W, in combination with a substitution at two or more positions corresponding to any of positions 1, 2, 68, 71, 126, 133, 142, 144, 156, 158, 176, 185, 201, 205, 213, 239, 279, 316, 360, 416, 437 and 450, in particular two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, Q360S, D416V, R437W and H450W.

Embodiment 213

The variant of any of Embodiments 1 to 37, which comprises a substitution at a position corresponding to position 360, in particular the substitution Q360S, in combination with an alteration at one or more positions corresponding to any of positions 1, 2, 68, 71, 126, 133, 142, 144, 156, 158, 176, 185, 201, 205, 213, 239, 279, 316, 318, 416, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, D416V, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W.

Embodiment 214

The variant of any of Embodiments 1 to 37, which comprises a substitution at a position corresponding to position 360, in particular the substitution Q360S, in combination with a substitution at one or more positions corresponding to any of positions 68, 176, 185, 201, 205, 213, 416 and 437, in particular one or more substitutions selected from the group consisting of H68W, K176L, E185P, I201Y, H205Y, K213T, D416V and R437W.

Embodiment 215

The variant of any of Embodiments 1 to 37, which comprises a substitution at a position corresponding to position 360, in particular the substitution Q360S, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 216

The variant of any of Embodiments 1 to 37, which comprises a substitution at a position corresponding to position 360, in particular the substitution Q360S, in combination with an alteration at two or more positions corresponding to any of positions 1, 2, 68, 71, 126, 133, 142, 144, 156, 158, 176, 185, 201, 205, 213, 239, 279, 316, 318, 416, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, D416V, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V, R437W and H450W.

Embodiment 217

The variant of any of Embodiments 1 to 37, which comprises a substitution at a position corresponding to position 360, in particular the substitution Q360S, in combination with a substitution at two or more positions corresponding to any of positions 68, 176, 185, 201, 205, 213, 416 and 437, in particular two or more substitutions selected from the group consisting of H68W, K176L, E185P, I201Y, H205Y, K213T, D416V and R437W.

Embodiment 218

The variant of any of Embodiments 1 to 37, which comprises a substitution at a position corresponding to position 360, in particular the substitution Q360S, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 219

The variant of any of Embodiments 1 to 37, which comprises a substitution at a position corresponding to position 416, in particular the substitution D416V, in combination with an alteration at one or more positions corresponding to any of positions 1, 2, 68, 71, 126, 133, 142, 144, 156, 158, 176, 185, 201, 205, 213, 239, 279, 316, 318, 360, 437 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, R437F, R437H, R437Y, R437W, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, R437W and H450W.

Embodiment 220

The variant of any of Embodiments 1 to 37, which comprises a substitution at a position corresponding to position 416, in particular the substitution D416V, in combination with a substitution at one or more positions corresponding to any of positions 68, 176, 185, 201, 205, 213, 360 and 437, in particular one or more substitutions selected from the group consisting of H68W, K176L, E185P, I201Y, H205Y, K213T, Q360S and R437W.

Embodiment 221

The variant of any of Embodiments 1 to 37, which comprises a substitution at a position corresponding to position 416, in particular the substitution D416V, in combination with a substitution at one or more positions corresponding to any of positions 2, 68, 133, 142, 156, 158, 279 and 437, in particular one or more substitutions selected from the group consisting of N2H, H68W, H133Y, H142W, Y156W, Y158W, F279W and R437W.

Embodiment 222

The variant of any of Embodiments 1 to 37, which comprises a substitution at a position corresponding to position 416, in particular the substitution D416V, in combination with an alteration at two or more positions corresponding to any of positions 1, 2, 68, 71, 126, 133, 142, 144, 156, 158, 176, 185, 201, 205, 213, 239, 279, 316, 318, 360, 437 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, R437F, R437H, R437Y, R437W, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, R437W and H450W.

Embodiment 223

The variant of any of Embodiments 1 to 37, which comprises a substitution at a position corresponding to position 416, in particular the substitution D416V, in combination with a substitution at two or more positions corresponding to any of positions 68, 176, 185, 201, 205, 213, 360 and 437, in particular two or more substitutions selected from the group consisting of H68W, K176L, E185P, I201Y, H205Y, K213T, Q360S and R437W.

Embodiment 224

The variant of any of Embodiments 1 to 37, which comprises a substitution at a position corresponding to position 416, in particular the substitution D416V, in combination with a substitution at two or more positions corresponding to any of positions 2, 68, 133, 142, 156, 158, 279 and 437, in particular two or more substitutions selected from the group consisting of N2H, H68W, H133Y, H142W, Y156W, Y158W, F279W and R437W.

Embodiment 225

The variant of any of Embodiments 1 to 37, which comprises a substitution at a position corresponding to position 437, in particular the substitution R437W, in combination with an alteration at one or more positions corresponding to any of positions 1, 2, 68, 71, 126, 133, 142, 144, 156, 158, 176, 185, 201, 205, 213, 239, 279, 316, 318, 360, 416 and 450, in particular one or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, H450F, H450Y and H450W, preferably one or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W.

Embodiment 226

The variant of any of Embodiments 1 to 37, which comprises a substitution at a position corresponding to position 437, in particular the substitution R437W, in combination with a substitution at one or more positions corresponding to any of positions 68, 176, 185, 201, 205, 213, 360 and 416, in particular one or more substitutions selected from the group consisting of H68W, K176L, E185P, I201Y, H205Y, K213T, Q360S and D416V.

Embodiment 227

The variant of any of Embodiments 1 to 37, which comprises a substitution at a position corresponding to position 437, in particular the substitution R437W, in combination with a substitution at one or more positions corresponding to any of positions 2, 68, 133, 142, 156, 158 and 279, in particular one or more substitutions selected from the group consisting of N2H, H68W, H133Y, H142W, Y156W, Y158W and F279W.

Embodiment 228

The variant of any of Embodiments 1 to 37, which comprises a substitution at a position corresponding to position 437, in particular the substitution R437W, in combination with an alteration at two or more positions corresponding to any of positions 1, 2, 68, 71, 126, 133, 142, 144, 156, 158, 176, 185, 201, 205, 213, 239, 279, 316, 318, 360, 416 and 450, in particular two or more alterations selected from the group consisting of A1AH, A1AF, A1AY, A1AW, A1H, A1F, A1Y, A1W, N2NH, N2N2F, N2NY, N2NW, N2H, N2F, N2Y, N2W, H68F, H68Y, H68W, G71F, G71H, G71Y, G71W, N126F, N126H, N126Y, N126W, H133F, H133Y, H133W, H142F, H142Y, H142W, P144F, P144H, P144Y, P144W, Y156F, Y156H, Y156W, Y158F, Y158H, Y158W, K176L, E185P, I201F, I201Y, H205Y, K213T, S239A, S239Q, F279Y, F279W, H316F, H316Y, H316W, L318F, L318H, L318Y, L318W, Q360S, D416V, H450F, H450Y and H450W, preferably two or more alterations selected from the group consisting of A1AH, A1AW, A1H, A1W, N2NH, N2NW, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and H450W.

Embodiment 229

The variant of any of Embodiments 1 to 37, which comprises a substitution at a position corresponding to position 437, in particular the substitution R437W, in combination with a substitution at two or more positions corresponding to any of positions 68, 176, 185, 201, 205, 213, 360 and 416, in particular two or more substitutions selected from the group consisting of H68W, K176L, E185P, I201Y, H205Y, K213T, Q360S and D416V.

Embodiment 230

The variant of any of Embodiments 1 to 37, which comprises a substitution at a position corresponding to position 437, in particular the substitution R437W, in combination with a substitution at two or more positions corresponding to any of positions 2, 68, 133, 142, 156, 158 and 279, in particular two or more substitutions selected from the group consisting of N2H, H68W, H133Y, H142W, Y156W, Y158W and F279W.

Embodiment 231

The variant of any of Embodiments 1 to 37, which comprises a substitution at a position corresponding to position 450, in particular the substitution H450W, in combination with a substitution at one or more positions corresponding to any of positions 1, 2, 68, 71, 126, 133, 142, 144, 156, 158, 176, 185, 201, 205, 213, 239, 279, 316, 318, 360, 416 and 437, in particular one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and R437W.

Embodiment 232

The variant of any of Embodiments 1 to 37, which comprises a substitution at a position corresponding to position 450, in particular the substitution H450W, in combination with a substitution at two or more positions corresponding to any of positions 1, 2, 68, 71, 126, 133, 142, 144, 156, 158, 176, 185, 201, 205, 213, 239, 279, 316, 318, 360, 416 and 437, in particular two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S, D416V and R437W.

Embodiment 233

The variant of any of embodiments 1 to 37 which comprises the substitutions H68W and K176L in combination with one or more substitutions selected from the group consisting of A1H, A1W, N2H, N2W, G71W, N126W, H133Y, H142W, P144W, Y156W, Y158W, E185P, I201Y, H205Y, K213T, S239A, S239Q, F279W, H316W, L318W, Q360S, D416V, R437W and H450W, in particular one or more substitutions selected from the group consisting of E185P, I201Y, H205Y, K213T, Q360S, D416V and R437W.

Embodiment 234

The variant of any of embodiments 1 to 37 which comprises the substitutions H68W and K176L in combination with two or more substitutions selected from the group consisting of A1H, A1W, N2H, N2W, G71W, N126W, H133Y, H142W, P144W, Y156W, Y158W, E185P, I201Y, H205Y, K213T, S239A, S239Q, F279W, H316W, L318W, Q360S, D416V, R437W and H450W, in particular two or more substitutions selected from the group consisting of E185P, I201Y, H205Y, K213T, Q360S, D416V and R437W.

Embodiment 235

The variant of any of embodiments 1 to 37 which comprises the substitutions H68W and E185P in combination with one or more substitutions selected from the group consisting of A1H, A1W, N2H, N2W, G71W, N126W, H133Y, H142W, P144W, Y156W, Y158W, K176L, I201Y, H205Y, K213T, S239A, S239Q, F279W, H316W, L318W, Q360S, D416V, R437W and H450W, in particular one or more substitutions selected from the group consisting of K176L, I201Y, H205Y, K213T, Q360S, D416V and R437W.

Embodiment 236

The variant of any of embodiments 1 to 37 which comprises the substitutions H68W and E185P in combination with two or more substitutions selected from the group consisting of A1H, A1W, N2H, N2W, G71W, N126W, H133Y, H142W, P144W, Y156W, Y158W, K176L, I201Y, H205Y, K213T, S239A, S239Q, F279W, H316W, L318W, Q360S, D416V, R437W and H450W, in particular two or more substitutions selected from the group consisting of K176L, I201Y, H205Y, K213T, Q360S, D416V and R437W.

Embodiment 237

The variant of any of embodiments 1 to 37 which comprises the substitutions H68W and I201Y in combination with one or more substitutions selected from the group consisting of A1H, A1W, N2H, N2W, G71W, N126W, H133Y, H142W, P144W, Y156W, Y158W, K176L, E185P, H205Y, K213T, S239A, S239Q, F279W, H316W, L318W, Q360S, D416V, R437W and H450W, in particular one or more substitutions selected from the group consisting of K176L, E185P, H205Y, K213T, Q360S, D416V and R437W.

Embodiment 238

The variant of any of embodiments 1 to 37 which comprises the substitutions H68W and I201Y in combination with two or more substitutions selected from the group consisting of A1H, A1W, N2H, N2W, G71W, N126W, H133Y, H142W, P144W, Y156W, Y158W, K176L, E185P, H205Y, K213T, S239A, S239Q, F279W, H316W, L318W, Q360S, D416V, R437W and H450W, in particular two or more substitutions selected from the group consisting of K176L, E185P, H205Y, K213T, Q360S, D416V and R437W.

Embodiment 239

The variant of any of embodiments 1 to 37 which comprises the substitutions H68W and H205Y in combination with one or more substitutions selected from the group consisting of A1H, A1W, N2H, N2W, G71W, N126W, H133Y, H142W, P144W, Y156W, Y158W, K176L, E185P, I201Y, K213T, S239A, S239Q, F279W, H316W, L318W, Q360S, D416V, R437W and H450W, in particular one or more substitutions selected from the group consisting of K176L, E185P, I201Y, K213T, Q360S, D416V and R437W.

Embodiment 240

The variant of any of embodiments 1 to 37 which comprises the substitutions H68W and H205Y in combination with two or more substitutions selected from the group consisting of A1H, A1W, N2H, N2W, G71W, N126W, H133Y, H142W, P144W, Y156W, Y158W, K176L, E185P, I201Y, K213T, S239A, S239Q, F279W, H316W, L318W, Q360S, D416V, R437W and H450W, in particular two or more substitutions selected from the group consisting of K176L, E185P, I201Y, K213T, Q360S, D416V and R437W.

Embodiment 241

The variant of any of embodiments 1 to 37 which comprises the substitutions H68W and K213T in combination with one or more substitutions selected from the group consisting of A1H, A1W, N2H, N2W, G71W, N126W, H133Y, H142W, P144W, Y156W, Y158W, K176L, E185P, I201Y, H205Y, S239A, S239Q, F279W, H316W, L318W, Q360S, D416V, R437W and H450W, in particular one or more substitutions selected from the group consisting of K176L, E185P, I201Y, H205Y, Q360S, D416V and R437W.

Embodiment 242

The variant of any of embodiments 1 to 37 which comprises the substitutions H68W and K213T in combination with two or more substitutions selected from the group consisting of A1H, A1W, N2H, N2W, G71W, N126W, H133Y, H142W, P144W, Y156W, Y158W, K176L, E185P, I201Y, H205Y, S239A, S239Q, F279W, H316W, L318W, Q360S, D416V, R437W and H450W, in particular two or more substitutions selected from the group consisting of K176L, E185P, I201Y, H205Y, Q360S, D416V and R437W.

Embodiment 243

The variant of any of embodiments 1 to 37 which comprises the substitutions H68W and Q360S in combination with one or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, D416V, R437W and H450W, in particular one or more substitutions selected from the group consisting of K176L, E185P, I201Y, H205Y, K213T, D416V and R437W.

Embodiment 244

The variant of any of embodiments 1 to 37 which comprises the substitutions H68W and Q360S in combination with two or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, D416V, R437W and H450W, in particular two or more substitutions selected from the group consisting of K176L, E185P, I201Y, H205Y, K213T, D416V and R437W.

Embodiment 245

The variant of any of embodiments 1 to 37 which comprises the substitutions H68W and D416V in combination with one or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, R437W and H450W, in particular one or more substitutions selected from the group consisting of K176L, E185P, I201Y, H205Y, K213T, Q360S and R437W.

Embodiment 246

The variant of any of embodiments 1 to 37 which comprises the substitutions H68W and D416V in combination with two or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, R437W and H450W, in particular two or more substitutions selected from the group consisting of K176L, E185P, I201Y, H205Y, K213T, Q360S and R437W.

Embodiment 247

The variant of any of embodiments 1 to 37 which comprises the substitutions H68W and R437W in combination with one or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V and H450W, in particular one or more substitutions selected from the group consisting of K176L, E185P, I201Y, H205Y, K213T, Q360S and D416V.

Embodiment 248

The variant of any of embodiments 1 to 37 which comprises the substitutions H68W and R437W in combination with two or more substitutions selected from the group consisting of A1H, A1W, N2H, N2W, G71W, N126W, H133Y, H142W, P144W, Y156W, Y158W, K176L, E185P, I201Y, H205Y, K213T, S239A, S239Q, F279W, H316W, L318W, Q360S, D416V and H450W, in particular two or more substitutions selected from the group consisting of K176L, E185P, I201Y, H205Y, K213T, Q360S and D416V.

Embodiment 249

The variant of any of embodiments 1 to 37 which comprises the substitutions K176L and E185P in combination with one or more substitutions selected from the group consisting of A1H, A1W, N2H, N2W, H68W, G71W, N126W, H133Y, H142W, P144W, Y156W, Y158W, I201Y, H205Y, K213T, S239A, S239Q, F279W, H316W, L318W, Q360S, D416V, R437W and H450W, in particular one or more substitutions selected from the group consisting of H68W, I201Y, H205Y, K213T, Q360S, D416V and R437W.

Embodiment 250

The variant of any of embodiments 1 to 37 which comprises the substitutions K176L and E185P in combination with two or more substitutions selected from the group consisting of A1H, A1W, N2H, N2W, H68W, G71W, N126W, H133Y, H142W, P144W, Y156W, Y158W, I201Y, H205Y, K213T, S239A, S239Q, F279W, H316W, L318W, Q360S, D416V, R437W and H450W, in particular two or more substitutions selected from the group consisting of H68W, I201Y, H205Y, K213T, Q360S, D416V and R437W.

Embodiment 251

The variant of any of embodiments 1 to 37 which comprises the substitutions K176L and I201Y in combination with one or more substitutions selected from the group consisting of A1H, A1W, N2H, N2W, H68W, G71W, N126W, H133Y, H142W, P144W, Y156W, Y158W, E185P, H205Y, K213T, S239A, S239Q, F279W, H316W, L318W, Q360S, D416V, R437W and H450W, in particular one or more substitutions selected from the group consisting of H68W, E185P, H205Y, K213T, Q360S, D416V and R437W.

Embodiment 252

The variant of any of embodiments 1 to 37 which comprises the substitutions K176L and I201Y in combination with two or more substitutions selected from the group consisting of A1H, A1W, N2H, N2W, H68W, G71W, N126W, H133Y, H142W, P144W, Y156W, Y158W, E185P, H205Y, K213T, S239A, S239Q, F279W, H316W, L318W, Q360S, D416V, R437W and H450W, in particular two or more substitutions selected from the group consisting of H68W, E185P, H205Y, K213T, Q360S, D416V and R437W.

Embodiment 253

The variant of any of embodiments 1 to 37 which comprises the substitutions K176L and H205Y in combination with one or more substitutions selected from the group consisting of A1H, A1W, N2H, N2W, H68W, G71W, N126W, H133Y, H142W, P144W, Y156W, Y158W, E185P, I201Y, K213T, S239A, S239Q, F279W, H316W, L318W, Q360S, D416V, R437W and H450W, in particular one or more substitutions selected from the group consisting of H68W, E185P, I201Y, K213T, Q360S, D416V and R437W.

Embodiment 254

The variant of any of embodiments 1 to 37 which comprises the substitutions K176L and H205Y in combination with two or more substitutions selected from the group consisting of A1H, A1W, N2H, N2W, H68W, G71W, N126W, H133Y, H142W, P144W, Y156W, Y158W, E185P, I201Y, K213T, S239A, S239Q, F279W, H316W, L318W, Q360S, D416V, R437W and H450W, in particular two or more substitutions selected from the group consisting of H68W, E185P, I201Y, K213T, Q360S, D416V and R437W.

Embodiment 255

The variant of any of embodiments 1 to 37 which comprises the substitutions K176L and K213T in combination with one or more substitutions selected from the group consisting of A1H, A1W, N2H, N2W, H68W, G71W, N126W, H133Y, H142W, P144W, Y156W, Y158W, E185P, I201Y, H205Y, S239A, S239Q, F279W, H316W, L318W, Q360S, D416V, R437W and H450W, in particular one or more substitutions selected from the group consisting of H68W, E185P, I201Y, H205Y, Q360S, D416V and R437W.

Embodiment 256

The variant of any of embodiments 1 to 37 which comprises the substitutions K176L and K213T in combination with two or more substitutions selected from the group consisting of A1H, A1W, N2H, N2W, H68W, G71W, N126W, H133Y, H142W, P144W, Y156W, Y158W, E185P, I201Y, H205Y, S239A, S239Q, F279W, H316W, L318W, Q360S, D416V, R437W and H450W, in particular two or more substitutions selected from the group consisting of H68W, E185P, I201Y, H205Y, Q360S, D416V and R437W.

Embodiment 257

The variant of any of embodiments 1 to 37 which comprises the substitutions K176L and Q360S in combination with one or more substitutions selected from the group consisting of A1H, A1W, N2H, N2W, H68W, G71W, N126W, H133Y, H142W, P144W, Y156W, Y158W, E185P, I201Y, H205Y, K213T, S239A, S239Q, F279W, H316W, L318W, D416V, R437W and H450W, in particular one or more substitutions selected from the group consisting of H68W, E185P, I201Y, H205Y, K213T, D416V and R437W.

Embodiment 258

The variant of any of embodiments 1 to 37 which comprises the substitutions K176L and Q360S in combination with two or more substitutions selected from the group consisting of A1H, A1W, N2H, N2W, H68W, G71W, N126W, H133Y, H142W, P144W, Y156W, Y158W, E185P, I201Y, H205Y, K213T, S239A, S239Q, F279W, H316W, L318W, D416V, R437W and H450W, in particular two or more substitutions selected from the group consisting of H68W, E185P, I201Y, H205Y, K213T, D416V and R437W.

Embodiment 259

The variant of any of embodiments 1 to 37 which comprises the substitutions K176L and D416V in combination with one or more substitutions selected from the group consisting of A1H, A1W, N2H, N2W, H68W, G71W, N126W, H133Y, H142W, P144W, Y156W, Y158W, E185P, I201Y, H205Y, K213T, S239A, S239Q, F279W, H316W, L318W, Q360S, R437W and H450W, in particular one or more substitutions selected from the group consisting of H68W, E185P, I201Y, H205Y, K213T, Q360S and R437W.

Embodiment 260

The variant of any of embodiments 1 to 37 which comprises the substitutions K176L and D416V in combination with two or more substitutions selected from the group consisting of A1H, A1W, N2H, N2W, H68W, G71W, N126W, H133Y, H142W, P144W, Y156W, Y158W, E185P, I201Y, H205Y, K213T, S239A, S239Q, F279W, H316W, L318W, Q360S, R437W and H450W, in particular two or more substitutions selected from the group consisting of H68W, E185P, I201Y, H205Y, K213T, Q360S and R437W.

Embodiment 261

The variant of any of embodiments 1 to 37 which comprises the substitutions K176L and R437W in combination with one or more substitutions selected from the group consisting of A1H, A1W, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V and H450W, in particular one or more substitutions selected from the group consisting of K176L, E185P, I201Y, H205Y, K213T, Q360S and D416V.

Embodiment 262

The variant of any of embodiments 1 to 37 which comprises the substitutions K176L and R437W in combination with two or more substitutions selected from the group consisting of A1H, A1W, N2H, N2W, H68W, G71W, N126W, H133Y, H142W, P144W, Y156W, Y158W, E185P, I201Y, H205Y, K213T, S239A, S239Q, F279W, H316W, L318W, Q360S, D416V and H450W, in particular two or more substitutions selected from the group consisting of K176L, E185P, I201Y, H205Y, K213T, Q360S and D416V.

Embodiment 263

The variant of any of embodiments 1 to 37 which comprises the substitutions E185P and I201Y in combination with one or more substitutions selected from the group consisting of A1H, A1W, N2H, N2W, H68W, G71W, N126W, H133Y, H142W, P144W, Y156W, Y158W, K176L, H205Y, K213T, S239A, S239Q, F279W, H316W, L318W, Q360S, D416V, R437W and H450W, in particular one or more substitutions selected from the group consisting of H68W, K176L, H205Y, K213T, Q360S, D416V and R437W.

Embodiment 264

The variant of any of embodiments 1 to 37 which comprises the substitutions E185P and I201Y in combination with two or more substitutions selected from the group consisting of A1H, A1W, N2H, N2W, H68W, G71W, N126W, H133Y, H142W, P144W, Y156W, Y158W, K176L, H205Y, K213T, S239A, S239Q, F279W, H316W, L318W, Q360S, D416V, R437W and H450W, in particular two or more substitutions selected from the group consisting of H68W, K176L, H205Y, K213T, Q360S, D416V and R437W.

Embodiment 265

The variant of any of embodiments 1 to 37 which comprises the substitutions E185P and H205Y in combination with one or more substitutions selected from the group consisting of A1H, A1W, N2H, N2W, H68W, G71W, N126W, H133Y, H142W, P144W, Y156W, Y158W, K176L, I201Y, K213T, S239A, S239Q, F279W, H316W, L318W, Q360S, D416V, R437W and H450W, in particular one or more substitutions selected from the group consisting of H68W, K176L, I201Y, K213T, Q360S, D416V and R437W.

Embodiment 266

The variant of any of embodiments 1 to 37 which comprises the substitutions E185P and H205Y in combination with two or more substitutions selected from the group consisting of A1H, A1W, N2H, N2W, H68W, G71W, N126W, H133Y, H142W, P144W, Y156W, Y158W, K176L, I201Y, K213T, S239A, S239Q, F279W, H316W, L318W, Q360S, D416V, R437W and H450W, in particular two or more substitutions selected from the group consisting of H68W, K176L, I201Y, K213T, Q360S, D416V and R437W.

Embodiment 267

The variant of any of embodiments 1 to 37 which comprises the substitutions E185P and K213T in combination with one or more substitutions selected from the group consisting of A1H, A1W, N2H, N2W, H68W, G71W, N126W, H133Y, H142W, P144W, Y156W, Y158W, K176L, I201Y, H205Y, S239A, S239Q, F279W, H316W, L318W, Q360S, D416V, R437W and H450W, in particular one or more substitutions selected from the group consisting of H68W, K176L, I201Y, H205Y, Q360S, D416V and R437W.

Embodiment 268

The variant of any of embodiments 1 to 37 which comprises the substitutions E185P and K213T in combination with two or more substitutions selected from the group consisting of A1H, A1W, N2H, N2W, H68W, G71W, N126W, H133Y, H142W, P144W, Y156W, Y158W, K176L, I201Y, H205Y, S239A, S239Q, F279W, H316W, L318W, Q360S, D416V, R437W and H450W, in particular two or more substitutions selected from the group consisting of H68W, K176L, I201Y, H205Y, Q360S, D416V and R437W.

Embodiment 269

The variant of any of embodiments 1 to 37 which comprises the substitutions E185P and Q360S in combination with one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, D416V, R437W and H450W, in particular one or more substitutions selected from the group consisting of H68W, K176L, I201Y, H205Y, K213T, D416V and R437W.

Embodiment 270

The variant of any of embodiments 1 to 37 which comprises the substitutions E185P and Q360S in combination with two or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, D416V, R437W and H450W, in particular two or more substitutions selected from the group consisting of H68W, K176L, I201Y, H205Y, K213T, D416V and R437W.

Embodiment 271

The variant of any of embodiments 1 to 37 which comprises the substitutions E185P and D416V in combination with one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, R437W and H450W, in particular one or more substitutions selected from the group consisting of H68W, K176L, I201Y, H205Y, K213T, Q360S and R437W.

Embodiment 272

The variant of any of embodiments 1 to 37 which comprises the substitutions E185P and D416V in combination with two or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, R437W and H450W, in particular two or more substitutions selected from the group consisting of H68W, K176L, I201Y, H205Y, K213T, Q360S and R437W.

Embodiment 273

The variant of any of embodiments 1 to 37 which comprises the substitutions E185P and R437W in combination with one or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V and H450W, in particular one or more substitutions selected from the group consisting of H68W, K176L, I201Y, H205Y, K213T, Q360S and D416V.

Embodiment 274

The variant of any of embodiments 1 to 37 which comprises the substitutions E185P and R437W in combination with two or more substitutions selected from the group consisting of A1H, A1W, N2H, N2W, H68W, G71W, N126W, H133Y, H142W, P144W, Y156W, Y158W, K176L, I201Y, H205Y, K213T, S239A, S239Q, F279W, H316W, L318W, Q360S, D416V and H450W, in particular two or more substitutions selected from the group consisting of H68W, K176L, I201Y, H205Y, K213T, Q360S and D416V.

Embodiment 275

The variant of any of embodiments 1 to 37 which comprises the substitutions I201Y and H205Y in combination with one or more substitutions selected from the group consisting of A1H, A1W, N2H, N2W, H68W, G71W, N126W, H133Y, H142W, P144W, Y156W, Y158W, K176L, E185P, K213T, S239A, S239Q, F279W, H316W, L318W, Q360S, D416V, R437W and H450W, in particular one or more substitutions selected from the group consisting of H68W, K176L, E185P, K213T, Q360S, D416V and R437W.

Embodiment 276

The variant of any of embodiments 1 to 37 which comprises the substitutions I201Y and H205Y in combination with with or more substitutions selected from the group consisting of A1H, A1W, N2H, N2W, H68W, G71W, N126W, H133Y, H142W, P144W, Y156W, Y158W, K176L, E185P, K213T, S239A, S239Q, F279W, H316W, L318W, Q360S, D416V, R437W and H450W, in particular two or more substitutions selected from the group consisting of H68W, K176L, E185P, K213T, Q360S, D416V and R437W.

Embodiment 277

The variant of any of embodiments 1 to 37 which comprises the substitutions I201Y and K213T in combination with one or more substitutions selected from the group consisting of A1H, A1W, N2H, N2W, H68W, G71W, N126W, H133Y, H142W, P144W, Y156W, Y158W, K176L, E185P, H205Y, S239A, S239Q, F279W, H316W, L318W, Q360S, D416V, R437W and H450W, in particular one or more substitutions selected from the group consisting of H68W, K176L, E185P, H205Y, Q360S, D416V and R437W.

Embodiment 278

The variant of any of embodiments 1 to 37 which comprises the substitutions I201Y and K213T in combination with two or more substitutions selected from the group consisting of A1H, A1W, N2H, N2W, H68W, G71W, N126W, H133Y, H142W, P144W, Y156W, Y158W, K176L, E185P, H205Y, S239A, S239Q, F279W, H316W, L318W, Q360S, D416V, R437W and H450W, in particular two or more substitutions selected from the group consisting of H68W, K176L, E185P, H205Y, Q360S, D416V and R437W.

Embodiment 279

The variant of any of embodiments 1 to 37 which comprises the substitutions I201Y and Q360S in combination with one or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, D416V, R437W and H450W, in particular one or more substitutions selected from the group consisting of H68W, K176L, E185P, H205Y, K213T, D416V and R437W.

Embodiment 280

The variant of any of embodiments 1 to 37 which comprises the substitutions I201Y and Q360S in combination with two or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, D416V, R437W and H450W, in particular two or more substitutions selected from the group consisting of H68W, K176L, E185P, H205Y, K213T, D416V and R437W.

Embodiment 281

The variant of any of embodiments 1 to 37 which comprises the substitutions I201Y and D416V in combination with one or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, R437W and H450W, in particular one or more substitutions selected from the group consisting of H68W, K176L, E185P, H205Y, K213T, Q360S and R437W.

Embodiment 282

The variant of any of embodiments 1 to 37 which comprises the substitutions I201Y and D416V in combination with two or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, R437W and H450W, in particular two or more substitutions selected from the group consisting of H68W, K176L, E185P, H205Y, K213T, Q360S and R437W.

Embodiment 283

The variant of any of embodiments 1 to 37 which comprises the substitutions I201Y and R437W in combination with one or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V and H450W, in particular one or more substitutions selected from the group consisting of H68W, K176L, E185P, H205Y, K213T, Q360S and D416V.

Embodiment 284

The variant of any of embodiments 1 to 37 which comprises the substitutions I201Y and R437W in combination with two or more substitutions selected from the group consisting of A1H, A1W, N2H, N2W, H68W, G71W, N126W, H133Y, H142W, P144W, Y156W, Y158W, K176L, E185P, H205Y, K213T, S239A, S239Q, F279W, H316W, L318W, Q360S, D416V and H450W, in particular two or more substitutions selected from the group consisting of H68W, K176L, E185P, H205Y, K213T, Q360S and D416V.

Embodiment 285

The variant of any of embodiments 1 to 37 which comprises the substitutions H205Y and K213T in combination with one or more substitutions selected from the group consisting of A1H, A1W, N2H, N2W, H68W, G71W, N126W, H133Y, H142W, P144W, Y156W, Y158W, K176L, E185P, I201Y, S239A, S239Q, F279W, H316W, L318W, Q360S, D416V, R437W and H450W, in particular one or more substitutions selected from the group consisting of H68W, K176L, E185P, I201Y, Q360S, D416V and R437W.

Embodiment 286

The variant of any of embodiments 1 to 37 which comprises the substitutions H205Y and K213T in combination with two or more substitutions selected from the group consisting of A1H, A1W, N2H, N2W, H68W, G71W, N126W, H133Y, H142W, P144W, Y156W, Y158W, K176L, E185P, I201Y, S239A, S239Q, F279W, H316W, L318W, Q360S, D416V, R437W and H450W, in particular two or more substitutions selected from the group consisting of H68W, K176L, E185P, I201Y, Q360S, D416V and R437W.

Embodiment 287

The variant of any of embodiments 1 to 37 which comprises the substitutions H205Y and Q360S in combination with one or more substitutions selected from the group consisting of A1H, A1W, N2H, N2W, H68W, G71W, N126W, H133Y, H142W, P144W, Y156W, Y158W, K176L, E185P, I201Y, S239A, S239Q, F279W, H316W, L318W, D416V, R437W and H450W, in particular one or more substitutions selected from the group consisting of H68W, K176L, E185P, I201Y, K213T, D416V and R437W.

Embodiment 288

The variant of any of embodiments 1 to 37 which comprises the substitutions H205Y and Q360S in combination with two or more substitutions selected from the group consisting of A1H, A1W, N2H, N2W, H68W, G71W, N126W, H133Y, H142W, P144W, Y156W, Y158W, K176L, E185P, I201Y, S239A, S239Q, F279W, H316W, L318W, D416V, R437W and H450W, in particular two or more substitutions selected from the group consisting of H68W, K176L, E185P, I201Y, K213T, D416V and R437W.

Embodiment 289

The variant of any of embodiments 1 to 37 which comprises the substitutions H205Y and D416V in combination with one or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, R437W and H450W, in particular one or more substitutions selected from the group consisting of H68W, K176L, E185P, I201Y, K213T, Q360S and R437W.

Embodiment 290

The variant of any of embodiments 1 to 37 which comprises the substitutions H205Y and D416V in combination with two or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, R437W and H450W, in particular two or more substitutions selected from the group consisting of H68W, K176L, E185P, I201Y, K213T, Q360S and R437W.

Embodiment 291

The variant of any of embodiments 1 to 37 which comprises the substitutions H205Y and R437W in combination with one or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V and H450W, in particular one or more substitutions selected from the group consisting of H68W, K176L, E185P, I201Y, K213T, Q360S and D416V.

Embodiment 292

The variant of any of embodiments 1 to 37 which comprises the substitutions H205Y and R437W in combination with two or more substitutions selected from the group consisting of A1H, A1W, N2H, N2W, H68W, G71W, N126W, H133Y, H142W, P144W, Y156W, Y158W, K176L, E185P, I201Y, K213T, S239A, S239Q, F279W, H316W, L318W, Q360S, D416V and H450W, in particular two or more substitutions selected from the group consisting of H68W, K176L, E185P, I201Y, K213T, Q360S and D416V.

Embodiment 293

The variant of any of embodiments 1 to 37 which comprises the substitutions K213T and Q360S in combination with one or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, D416V, R437W and H450W, in particular one or more substitutions selected from the group consisting of H68W, K176L, E185P, I201Y, H205Y, D416V and R437W.

Embodiment 294

The variant of any of embodiments 1 to 37 which comprises the substitutions K213T and Q360S in combination with two or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, D416V, R437W and H450W, in particular two or more substitutions selected from the group consisting of H68W, K176L, E185P, I201Y, H205Y, D416V and R437W.

Embodiment 295

The variant of any of embodiments 1 to 37 which comprises the substitutions K213T and D416V in combination with one or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, R437W and H450W, in particular one or more substitutions selected from the group consisting of H68W, K176L, E185P, I201Y, H205Y, Q360S and R437W.

Embodiment 296

The variant of any of embodiments 1 to 37 which comprises the substitutions K213T and D416V in combination with two or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, R437W and H450W, in particular two or more substitutions selected from the group consisting of H68W, K176L, E185P, I201Y, H205Y, Q360S and R437W.

Embodiment 297

The variant of any of embodiments 1 to 37 which comprises the substitutions K213T and R437W in combination with one or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V and H450W, in particular one or more substitutions selected from the group consisting of H68W, K176L, E185P, I201Y, H205Y, Q360S and D416V.

Embodiment 298

The variant of any of embodiments 1 to 37 which comprises the substitutions K213T and R437W in combination with two or more substitutions selected from the group consisting of A1H, A1W, N2H, N2W, H68W, G71W, N126W, H133Y, H142W, P144W, Y156W, Y158W, K176L, E185P, I201Y, H205Y, S239A, S239Q, F279W, H316W, L318W, Q360S, D416V and H450W, in particular two or more substitutions selected from the group consisting of H68W, K176L, E185P, I201Y, H205Y, Q360S and D416V.

Embodiment 299

The variant of any of embodiments 1 to 37 which comprises the substitutions Q360S and D416V in combination with one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, R437W and H450W, in particular one or more substitutions selected from the group consisting of H68W, K176L, E185P, I201Y, H205Y, K213T and R437W.

Embodiment 300

The variant of any of embodiments 1 to 37 which comprises the substitutions Q360S and D416V in combination with two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, R437W and H450W, in particular two or more substitutions selected from the group consisting of H68W, K176L, E185P, I201Y, H205Y, K213T and R437W.

Embodiment 301

The variant of any of embodiments 1 to 37 which comprises the substitutions Q360S and R437W in combination with one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V and H450W, in particular one or more substitutions selected from the group consisting of H68W, K176L, E185P, I201Y, H205Y, K213T and D416V.

Embodiment 302

The variant of any of embodiments 1 to 37 which comprises the substitutions Q360S and R437W in combination with two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, D416V and H450W, in particular two or more substitutions selected from the group consisting of H68W, K176L, E185P, I201Y, H205Y, K213T and D416V.

Embodiment 303

The variant of any of embodiments 1 to 37 which comprises the substitutions D416V and R437W in combination with one or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S and H450W, in particular one or more substitutions selected from the group consisting of H68W, K176L, E185P, I201Y, H205Y, K213T and Q360S.

Embodiment 304

The variant of any of embodiments 1 to 37 which comprises the substitutions D416V and R437W in combination with two or more substitutions selected from the group consisting of A1H, A1W, N2H, N2W, H68W, G71W, N126W, H133Y, H142W, P144W, Y156W, Y158W, K176L, E185P, I201Y, H205Y, K213T, S239A, S239Q, F279W, H316W, L318W, Q360S and H450W, in particular two or more substitutions selected from the group consisting of H68W, K176L, E185P, I201Y, H205Y, K213T and Q360S.

Embodiment 305

The variant of any of Embodiments 1-305, which further comprises a substitution at one or more positions corresponding to any of positions 15, 48, 49, 107, 138, 156, 181, 187, 188, 190, 197, 209, 239, 255, 264, 299, 474 and 475 of SEQ ID NO: 1.

Embodiment 306

The variant of Embodiment 305, wherein the variant comprises:

a substitution at a position corresponding to position 15 with Ala, Arg, Asn, Asp, Cys, Gln, Glu, Gly, His, Ile, Leu, Lys, Phe, Pro, Ser, Thr, Trp, Tyr or Val, in particular with Leu, Ser or Thr;

a substitution at a position corresponding to position 48 with Ala, Arg, Asn, Asp, Cys, Gln, Glu, His, Ile, Leu, Lys, Met, Phe, Pro, Ser, Thr, Trp, Tyr or Val, in particular with Ala;

a substitution at a position corresponding to position 49 with Ala, Arg, Asn, Asp, Cys, Gln, Glu, Gly, His, Ile, Leu, Lys, Met, Phe, Pro, Ser, Trp, Tyr or Val, in particular with Gly, His, Ile or Leu;

a substitution at a position corresponding to position 107 with Ala, Arg, Asn, Asp, Cys, Gln, Glu, His, Ile, Leu, Lys, Met, Phe, Pro, Ser, Thr, Trp, Tyr or Val, in particular with Ala;

a substitution at a position corresponding to position 138 with Ala, Arg, Asn, Asp, Cys, Gln, Glu, Gly, His, Ile, Leu, Lys, Met, Phe, Pro, Ser, Thr, Trp, Tyr or Val, in particular with Phe or Tyr;

a substitution at a position corresponding to position 156 with Ala, Arg, Asn, Asp, Cys, Gln, Glu, Gly, Ile, Leu, Lys, Met, Phe, Pro, Ser, Thr, Trp, Tyr or Val, in particular with Tyr;

a substitution at a position corresponding to position 181 with Arg, Asn, Asp, Cys, Gln, Glu, Gly, His, Ile, Leu, Lys, Met, Phe, Pro, Ser, Thr, Trp, Tyr or Val, in particular with Asp, Glu or Thr;

a substitution at a position corresponding to position 187 with Ala, Arg, Asn, Asp, Cys, Gln, Glu, Gly, His, Ile, Leu, Lys, Met, Phe, Pro, Thr, Trp, Tyr or Val, in particular with Asp;

a substitution at a position corresponding to position 188 with Ala, Arg, Asp, Cys, Gln, Glu, Gly, His, Ile, Leu, Lys, Met, Phe, Pro, Ser, Thr, Trp, Tyr or Val, in particular with Ser or Thr;

a substitution at a position corresponding to position 190 with Ala, Arg, Asp, Cys, Gln, Glu, Gly, His, Ile, Leu, Lys, Met, Phe, Pro, Ser, Thr, Trp, Tyr or Val, in particular with Phe;

a substitution at a position corresponding to position 197 with Ala, Arg, Asn, Asp, Cys, Gln, Glu, Gly, His, Ile, Leu, Lys, Phe, Pro, Ser, Thr, Trp, Tyr or Val, in particular with Ile, Leu, Ser, Thr or Val;

a substitution at a position corresponding to position 209 with Arg, Asn, Asp, Cys, Gln, Glu, Gly, His, Ile, Leu, Lys, Met, Phe, Pro, Ser, Thr, Trp, Tyr or Val, in particular with Val;

a substitution at a position corresponding to position 239 with Ala, Arg, Asn, Asp, Cys, Gln, Glu, Gly, His, Ile, Leu, Lys, Met, Phe, Pro, Thr, Trp, Tyr or Val, in particular with Ala, Asn, Asp, Gln, Glu, Met or Cys;

a substitution at a position corresponding to position 255 with Ala, Arg, Asn, Asp, Cys, Gln, Gly, His, Ile, Leu, Lys, Met, Phe, Pro, Ser, Thr, Trp, Tyr or Val, in particular with Gly or Pro;

a substitution at a position corresponding to position 264 with Ala, Arg, Asn, Asp, Cys, Glu, Gly, His, Ile, Leu, Lys, Met, Phe, Pro, Ser, Thr, Trp, Tyr or Val, in particular with Ser;

a substitution at a position corresponding to position 299 with Ala, Arg, Asn, Asp, Cys, Gln, Glu, His, Ile, Leu, Lys, Met, Phe, Pro, Ser, Thr, Trp, Tyr or Val, in particular with Arg;

a substitution at a position corresponding to position 474 with Ala, Arg, Asn, Asp, Cys, Gln, Glu, His, Ile, Leu, Lys, Met, Phe, Pro, Ser, Thr, Trp, Tyr or Val, in particular with Arg, Gln, Glu or Lys; or a substitution at a position corresponding to position 475 with Ala, Arg, Asn, Asp, Cys, Gln, Glu, His, Ile, Leu, Lys, Met, Phe, Pro, Ser, Thr, Trp, Tyr or Val, in particular with Arg, Gln, Glu or Lys.

Embodiment 307

The variant of any of Embodiments 306 to 307, which comprises one or more substitutions selected from the group consisting of M15T, M15S, M15L, G48A, T49L, T49I, G107A, W138Y, W138F, H156Y, A181T, A181E, A181D, S187D, N188S, N188T, N190F, M197S, M197T, M197V, M197L, M197I, A209V, S239Q, S239E, S239N, S239D, S239A, S239M, S239C, E255P, E255G, Q264S, G299R, G474K, G474R, G474E, G474Q, G475K, G475R, G475E and G475Q.

Embodiment 308

The variant of any of Embodiments 1 to 308, which comprises or consists of a set of substitutions selected from the group consisting of:
A1H+N2W+K176L+E185P,
A1W+N2H+K176L+E185P,
N2H+H68W+H133Y+K176L+E185P,
N2H+H68W+Y156W+K176L+E185P,
N2H+H68W+Y158W+K176L+E185P,
N2H+H68W+K176L+E185P,
N2H+H68W+K176L+E185P+I201Y+H205Y+D207V+V209D,
N2H+H68W+K176L+E185P+F279W,
N2H+H133Y+K176L+E185P+H316W+R437W,
N2H+H133Y+K176L+E185P+Q360S+R437W,
N2H+H142W+K176L+E185P+H316W+R437W,
N2H+H142W+K176L+E185P+Q360S+R437W,
N2H+P144W+K176L+E185P,
N2H+Y156W+Y158W+K176L+E185P+H316W+R437W,
N2H+Y156W+K176L+E185P+Q360S+R437W,
N2H+Y158W+K176L+E185P+I201Y+H205Y+D207V+V209D+H316W,
N2H+K176L+E185P,
N2H+K176L+E185P+H316W,
N2H+K176L+E185P+H316W+L318W+R437W,
N2H+K176L+E185P+H316W+Q360S+R437W,
N2H+K176L+E185P+H316W+R437W,
N2H+K176L+E185P+R437W,
N2H+K176L+E185P+Q360S+R437W,
N2H+K176L+E185P+H316W+Q360S+R437W,
N2H+K176L+I201Y+H205Y+K213T+Q360S+D416V+R437W,
H68W+K176L+E185P,
H68W+K176L+E185P+I201Y+H205Y+K213T+Q360S+D416V+R437W,
H68W+K176L+I201Y+H205Y+K213T+Q360S+D416V+R437W,
G71W+K176L+E185P,
N126W+K176L+I201Y+H205Y+K213T+Q360S+D416V+R437W,
H133Y+Y158W+K176L+E185P+I201Y+H205Y+K213T+Q360S+D416V+R437W,
H133Y+K176L+I201Y+H205Y+K213T+Q360S+D416V+R437W,
H142W+Y158W+K176L+E185P+I201Y+H205Y+K213T+Q360S+D416V+R437W,
H142W+K176L+E185P,
H142W+K176L+E185P+I201Y+H205Y+K213T+Q360S+D416V+R437W,
H142W+K176L+I201Y+H205Y+K213T+Q360S+D416V+R437W,
P144W+K176L+E185P,
Y156W+Y158W+K176L+E185P+I201Y+H205Y+K213T+Q360S+D416V+R437W,
Y156W+Y158W+K176L+E185P+H316W+R437W,
Y156W+K176L+E185P+Q360S+R437W,
Y156W+K176L+I201Y+H205Y+K213T+Q360S+D416V+R437W,
Y158W+K176L+E185P,
Y158W+K176L+E185P+I201Y+H205Y+D207V+V209D+H316W,
Y158W+K176L+E185P+I201Y+H205Y+K213T+H316L+L318W+Q360S+D416V+R437W,
Y158W+K176L+E185P+I201Y+H205Y+K213T+H316W+Q360S+D416V+R437W,
Y158W+K176L+E185P+I201Y+H205Y+K213T+Q360S+D416V+R437W,
Y158W+K176L+I201Y+H205Y+K213T+Q360S+D416V+R437W,
K176L+E185P,
K176L+E185P+I201Y+H205Y+K213T+Q360S+D416V+R437W,
K176L+E185P+I201Y+H205Y+R437W,
K176L+E185P+F279W,
K176L+E185P+H316W,
K176L+E185P+L318W,
K176L+E185P+H450W,
K176L+I201Y+H205Y+K213T+S239Q+Q360S+D416V+R437W,
K176L+I201Y+H205Y+K213T+H316W+Q360S+D416V+R437W,
K176L+I201Y+H205Y+K213T+L318W+Q360S+D416V+R437W,
K176L+I201Y+H205Y+K213T+Q360S+D416V+R437W,
K176L+I201Y+H205Y+K213T+Q360S+R437W,
K176L+I201Y+H205Y+K213T+D416V+R437W, and
K176L+I201Y+H205Y+Q360S+D416V+R437W.

Embodiment 309

The variant of any of Embodiments 1 to 309 which further comprises a deletion at both of the two positions immediately before position 180 of SEQ ID NO: 1.

Embodiment 310

The variant of any of Embodiments 1 to 310, wherein the total number of substitutions is 2-20, e.g., 2-10 or 2-5, such as 2, 3, 4, 5, 6, 7, 8, 9 or 10 substitutions.

Embodiment 311

The variant of any of Embodiments 1 to 311, which has increased thermostability compared to the mature polypeptide of SEQ ID NO: 1 when incubated at high temperature, low calcium and low pH in the presence of at least 0.1% starch, e.g., in the presence of 0.9% or 1% starch.

Embodiment 312

The variant of any of Embodiments 1 to 311, which has increased thermostability compared to the mature polypeptide of SEQ ID NO: 14 when incubated at high temperature, low calcium and low pH in the presence of at least 0.1% starch, e.g., in the presence of 0.9% or 1% starch.

Embodiment 313

The variant of any of Embodiments 1 to 311, which has increased thermostability compared to its parent when incubated at high temperature, low calcium and low pH in the presence of at least 0.1% starch, e.g., in the presence of 0.9% or 1% starch.

Embodiment 314

The variant of any of Embodiments 1 to 311, which has an increased residual activity half-life compared to the mature polypeptide of SEQ ID NO: 1 when incubated with 0.125 mM $CaCl_2$, 0.9% starch at 95° C. and pH 4.8.

Embodiment 315

The variant of any of Embodiments 1 to 311, which has an increased residual activity half-life compared to the mature polypeptide of SEQ ID NO: 14 when incubated with 0.125 mM $CaCl_2$, 0.9% starch at 95° C. and pH 4.8.

Embodiment 316

The variant of any of Embodiments 1 to 311, which has an increased residual activity half-life compared to its parent when incubated with 0.125 mM $CaCl_2$, 0.9% starch at 95° C. and pH 4.8.

Embodiment 317

The variant of any of Embodiments 1 to 311, which has an increased residual activity half-life compared to the mature polypeptide of SEQ ID NO: 1 when incubated with 0.125 mM $CaCl_2$, 0.9% starch at 95° C. and pH 4.5.

Embodiment 318

The variant of any of Embodiments 1 to 311, which has an increased residual activity half-life compared to the mature polypeptide of SEQ ID NO: 14 when incubated with 0.125 mM $CaCl_2$, 0.9% starch at 95° C. and pH 4.5.

Embodiment 319

The variant of any of Embodiments 1 to 311, which has an increased residual activity half-life compared to its parent when incubated with 0.125 mM $CaCl_2$, 0.9% starch at 95° C. and pH 4.5.

Embodiment 320

A detergent composition comprising the variant of any of Embodiments 1 to 320 and a surfactant.

Embodiment 321

A composition comprising the variant of any of Embodiments 1 to 320 and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease and pullulanase.

Embodiment 322

Use of the variant of any of Embodiments 1 to 320 for washing and/or dishwashing.

Embodiment 323

Use of the variant of any of Embodiments 1 to 320 for desizing a textile.

Embodiment 324

Use of the variant of any of Embodiments 1 to 320 for producing a baked product.

Embodiment 325

Use of the variant of any of Embodiments 1 to 320 for liquefying a starch-containing material.

Embodiment 326

A method of producing liquefied starch, comprising liquefying a starch-containing material with the variant of any of Embodiments 1 to 320.

Embodiment 327

A method of producing a fermentation product, comprising
(a) liquefying a starch-containing material with the variant of any of Embodiments 1 to 320 to produce a liquefied mash;
(b) saccharifying the liquefied mash to produce fermentable sugars; and
(C) fermenting the fermentable sugars in the presence of a fermenting organism.

Embodiment 328

The method of Embodiment 328, wherein step (a) is performed at pH 4-5.

Embodiment 329

A method of producing a fermentation product, comprising contacting a starch substrate with the variant of any of Embodiments 1 to 320, a glucoamylase, and a fermenting organism.

Embodiment 330

An isolated polynucleotide encoding the variant of any of Embodiments 1 to 320.

Embodiment 331

A nucleic acid construct comprising the polynucleotide of Embodiment 331.

Embodiment 332

An expression vector comprising the polynucleotide of Embodiment 331.

Embodiment 333

A host cell comprising the polynucleotide of Embodiment 331.

Embodiment 334

A method of producing an alpha-amylase variant, comprising:
a. cultivating the host cell of Embodiment 334 under conditions suitable for expression of the variant; and
b. recovering the variant.

Embodiment 335

A method for obtaining an alpha-amylase variant, comprising (a) introducing into a parent alpha-amylase a substitution at one or more positions corresponding to any of positions 1, 2, 68, 71, 126, 133, 142, 144, 156, 158, 176, 185, 201, 205, 213, 239, 279, 316, 318, 360, 416, 437 and 450 of SEQ ID NO: 1; and (b) recovering the variant.

The present invention is further described by the following examples that should not be construed as limiting the scope of the invention.

EXAMPLES

Assays for Measurement of Amylolytic Activity (Alpha-Amylase Activity)
PNP-G7 Assay:

The alpha-amylase activity is determined by a method employing the PNP-G7 substrate. PNP-G7 is an abbreviation for 4,6-ethylidene($G_7$)-p-nitrophenyl(Gi)-α,D-maltoheptaoside, a blocked oligosaccharide which can be cleaved by an endo-amylase, such as an alpha-amylase. Following the cleavage, the alpha-glucosidase included in the kit digest the hydrolysed substrate further to liberate a free PNP molecule which has a yellow color and thus can be measured by visible spectophometry at λ=405 nm (400-420 nm.). Kits containing PNP-G7 substrate and alpha-glucosidase is manufactured by Roche/Hitachi (cat. No. 11876473).
Reagents:
The G7-PNP substrate from this kit contains 22 mM 4,6-ethylidene-G7-PNP and 52.4 mM HEPES (2-[4-(2-hydroxyethyl)-1-piperazinyl]-ethanesulfonic acid), pH 7.0.

The alpha-glucosidase reagent contains 52.4 mM HEPES, 87 mM NaCl, 12.6 mM $MgCl_2$, 0.075 mM $CaCl_2$, >4 kU/L alpha-glucosidase.
The substrate working solution is made by mixing 1 ml of the alpha-glucosidase reagent with 0.2 ml of the G7-PNP substrate. This substrate working solution is made immediately before use. Dilution buffer: 50 mM EPPS, 0.01% (w/v) Triton X100 (polyethylene glycol p-(1,1,3,3-tetramethylbutyl)-phenyl ether $(C_{14}H_{22}O(C_2H_4O)_n$ (n=9-10))), 1 mM $CaCl_2$, pH 7.0.
Procedure:

The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.
Phadebas Activity Assay:

The alpha-amylase activity can also be determined by a method using the Phadebas substrate (from for example Magle Life Sciences, Lund, Sweden). A Phadebas tablet includes interlinked starch polymers that are in the form of globular microspheres that are insoluble in water. A blue dye is covantly bound to these microspheres. The interlinked starch polymers in the microsphere are degraded at a speed that is proportional to the alpha-amylase activity. When the alpha-amylse degrades the starch polymers, the released blue dye is water soluble and concentration of dye can be determined by measuring absorbance at 620 nm. The concentration of blue is proportional to the alpha-amylase activity in the sample.

The amylase sample to be analysed is diluted in dilution buffer with the desired pH. One substrate tablet is suspended in 5 mL activity buffer and mixed on magnetic stirrer. During mixing of substrate transfer 150 µl to microtiter plate (MTP) or PCR-MTP. Add 30 µl diluted amylase sample to 150 µl substrate and mix. Incubate for 15 minutes at 37° C. The reaction is stopped by adding 30 µl 1 M NaOH and mix. Centrifuge MTP for 5 minutes at 4000×g. Transfer 100 µl to new MTP and measure absorbance at 620 nm.

The amylase sample should be diluted so that the absorbance at 620 nm is between 0 and 2.2.
Enzchek® Assay:

For the determination of residual amylase activity an EnzChek® Ultra Amylase Assay Kit (E33651, Invitrogen, La Jolla, Calif., USA) was used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.
Reference Alpha-Amylase and Variants Thereof The reference alpha-amylase is LE399 (previously disclosed in, e.g., WO 02/10355). LE399 comprises amino acids 1-37 of the alpha-amylase from *Bacillus amyloliquefaciens* (SEQ ID NO: 6) and amino acids 40-483 of the alpha-amylase from *Bacillus licheniformis* (SEQ ID NO: 1) with the following substitutions G48A T49I G107A H156Y A181T N190F I201F A209V Q264S.

The variants tested are variants of LE399, so the substitutions in each variant as listed in the tables below are substitutions as compared to LE399. The position numbering is according to SEQ ID NO: 1.

LE399 is two amino acids shorter than SEQ ID NO: 1 in the N-terminal, i.e., there are no amino acids corresponding to positions 1 and 2 of SEQ ID NO: 1 in LE399. The alteration denoted in the tables as *2aH means insertion of H before the N-terminal V of LE399. A similar alteration in SEQ ID NO: 1 would be substitution of amino acid N2 with H, i.e., N2H (alternatively, deletion of amino acid A1 combined with substitution of amino acid N2 with H, i.e., A1*N2H). Likewise, the alterations denoted in the tables as *2aH*2bW means insertion of HW before the N-terminal V of LE399. A similar alteration in SEQ ID NO: 1 would be the substitutions A1H N2W.

Example 1

Thermostability of Alpha-Amylase Variants with 0.9% starch at pH 4.5 The thermostability of a reference alpha-amylase and alpha-amylase variants thereof was determined by incubating the reference alpha-amylase and variants at pH 4.5 and 90 or 95° C. with 0.125 mM CaCl$_2$ and 0.9% starch (corn starch) followed by residual activity determination using the EnzChek® substrate (EnzChek® Ultra Amylase assay kit, E33651, Molecular Probes).

Purified enzyme samples were diluted to working concentrations of 5 and 10 ppm (micrograms/ml) in enzyme dilution buffer (10 mM acetate, 0.01% Triton X100, 0.125 mM CaCl$_2$, pH 5.0). Twenty microliters enzyme sample was transferred to 96-well PCR MTP and 180 microliters stability buffer (150 mM acetate, 0.01% Triton X100, 0.125 mM CaCl$_2$, pH 4.5, +/−0.9% starch) was added to each well and mixed. The assay was performed using two concentrations of enzyme in duplicates. Before incubation at 90 or 95° C., 20 microliters was withdrawn and stored on ice as unstressed control samples. Incubation was performed in a PCR machine (pH 4.5, 90/95° C., 0.125 mM CaCl$_2$, +/−0.9% starch). Incubation time (minutes) was selected so that residual activity was between 6-84%. If the residual activity is outside this interval then it is indicated by > or <.

After incubation samples were diluted to 10-20 ng enzyme protein/ml in residual activity buffer (100 mM Acetate, 0.01% Triton X100, 0.125 mM CaCl$_2$, pH 5.5) and 25 microliters diluted enzyme was transferred to black 384-well MTP. Residual activity was determined using the EnzChek® substrate by adding 25 microliters substrate solution (100 micrograms/ml) to each well. Fluorescence was determined at 25° C. every minute for 15 minutes using excitation filter at 485-P nm and emission filter at 555 nm (fluorescence reader is Polarstar, BMG). The residual activity was normalized to unstressed control samples for each setup.

Assuming exponential decay half life time (T½ (min)) was calculated using the equation: T½ (min)=T(min)*LN (0.5)/LN(% RA/100), where T is assay incubation time in minutes, and % RA is % residual activity determined in assay.

Using this assay setup the half life time was determined as a measure of thermostability for the reference alpha-amylase and variants thereof as shown in Tables 1 and 2.

Reference amylase was incubated at pH 4.5, 0.125 mM CaCl$_2$, +/−0.9% starch, at 90° C. for 5 minutes (Table 1).

TABLE 1 pH 4.5, 0.125 mM CaCl$_2$, 90° C. for 5 or 15 minutes in 0.9% starch
pH 4.5, 0.125 mM CaCl$_2$, 90° C. in buffer for 5 or 8 minutes

| Mutations | T½ (min) (pH 4.5, 0.125 mM CaCl$_2$, buffer, 90° C.) | T½ (min) (pH 4.5, 0.125 mM CaCl$_2$, 0.9% starch, 90° C.) |
| --- | --- | --- |
| Reference | 2 | 3 |
| K176L F201Y H205Y K213T Q360S D416V R437W | 6 | 11 |
| K176L F201Y H205Y K213T Q360S D416V R437W H133Y | 14 | 17 |
| K176L F201Y H205Y K213T Q360S D416V R437W S239Q | 18 | 21 |
| K176L F201Y H205Y K213T Q360S D416V R437W H316W | 5 | 10 |
| K176L F201Y H205Y K213T Q360S D416V R437W L318W | 6 | 10 |
| K176L F201Y H205Y K213T Q360S D416V R437W *2aH | 6 | 10 |
| K176L F201Y H205Y K213T Q360S D416V R437W N126W | 2 | 5 |
| K176L F201Y H205Y K213T Q360S D416V R437W H68W | 5 | 11 |
| K176L F201Y H205Y K213T Q360S D416V R437W Y158W | 6 | 11 |
| K176L F201Y H205Y K213T Q360S D416V R437W Y156W | 5 | 11 |
| K176L F201Y H205Y K213T Q360S D416V R437W H142W | 7 | 11 |

TABLE 2 pH 4.5, 0.125 mM CaCl$_2$, 95° C. in 0.9% starch for 30 or 50 minutes
pH 4.5, 0.125 mM CaCl$_2$, 95° C. in buffer for 30 minutes

| Mutations | T½ (min) (pH 4.5 0.125 mM CaCl$_2$ buffer 95° C.) | T½ (min) (pH 4.5 0.125 mM CaCl$_2$ 0.9% starch 95° C.) |
| --- | --- | --- |
| K176L E185P | 20 | 27 |
| *2aH K176L E185P | 18 | 37 |
| *2aH *2bW K176L E185P | 21 | 30 |
| H68W K176L E185P | 17 | 33 |
| G71W K176L E185P | 20 | 32 |
| P144W K176L E185P | 18 | 36 |

TABLE 2-continued pH 4.5, 0.125 mM CaCl$_2$, 95° C. in 0.9% starch for 30 or 50 minutes
pH 4.5, 0.125 mM CaCl$_2$, 95° C. in buffer for 30 minutes

| Mutations | T½ (min) (pH 4.5 0.125 mM CaCl$_2$ buffer 95° C.) | T½ (min) (pH 4.5 0.125 mM CaCl$_2$ 0.9% starch 95° C.) |
|---|---|---|
| Y158W K176L E185P | 17 | 28 |
| K176L E185P F279W | 20 | 33 |
| K176L E185P H316W | 23 | 38 |
| K176L E185P *2aH R437W | 23 | >120 |
| K176L E185P H450W | 20 | 46 |
| K176L E185P *2aH H316W | 22 | 65 |
| *2aH P144W K176L E185P | 19 | 71 |
| K176L F201Y H205Y K213T Q360S D416V R437W H133Y | <0 | 32 |
| K176L F201Y H205Y K213T Q360S D416V R437W | <0 | 14 |
| H142W K176L E185P | 13 | 43 |
| K176L E185P L318W | 12 | 41 |
| *2aH Y158W K176L E185P F201Y H205Y D207V V209D H316W | 24 | 63 |
| *2aH K176L E185P | 18 | 36 |
| *2aH H68W K176L E185P H133Y | 27 | 74 |
| *2aH K176L E185P H316W R437W | 24 | 44 |
| *2aH K176L E185P H316W R437W L318W | 20 | 37 |
| *2aH K176L E185P H316W R437W H133Y | 32 | 60 |
| *2aH K176L E185P H316W R437W Y156W Y158W | 22 | 44 |
| *2aH K176L E185P H316W R437W H142W | 23 | 59 |
| *2aH K176L E185P R437W Q360S | 20 | 36 |
| *2aH K176L E185P R437W Q360S Y156W | 18 | 34 |
| *2aH K176L E185P R437W Q360S H142W | 16 | 27 |
| *2aH K176L E185P R437W Q360S H133Y | 26 | 42 |
| *2aH K176L E185P R437W Q360S H316W | 23 | 38 |
| *2aH K176L E185P H316W R437W Q360S | 22 | 34 |
| K176L F201Y H205Y K213T Q360S D416V R437W E185P | 19 | 30 |
| K176L F201Y H205Y K213T Q360S D416V R437W E185P H142W | 18 | 25 |
| K176L F201Y H205Y K213T Q360S D416V R437W E185P H68W | 18 | 25 |
| K176L F201Y H205Y K213T Q360S D416V R437W E185P Y158W H133Y | 24 | 33 |
| K176L F201Y H205Y K213T Q360S D416V R437W E185P Y158W H142W | 19 | 31 |
| K176L F201Y H205Y K213T Q360S D416V R437W E185P Y158W Y156W | 21 | 28 |
| K176L F201Y H205Y K213T Q360S D416V R437W E185P Y158W H316W | 24 | 32 |
| K176L F201Y H205Y K213T Q360S D416V R437W E185P Y158W H316L L318W | 18 | 20 |
| *2aH H68W K176L E185P | 15 | 39 |
| *2aH H68W K176L E185P Y158W | 17 | 30 |
| *2aH H68W K176L E185P Y156W | 16 | 28 |
| *2aH H68W K176L E185P F279W | 14 | 44 |
| *2aH H68W K176L E185P F201Y H205Y D207V V209D | 14 | 16 |
| *2aH H68W K176L E185P H133Y | 23 | 78 |

Example 2

Thermostability of Alpha-Amylase Variants with 0.9% Starch at pH 4.8

The thermostability of a reference alpha-amylase and alpha-amylase variants thereof was determined by incubating the reference alpha-amylase and variants at pH 4.8 and 90 or 95° C. with 0.125 mM CaCl$_2$)+/−0.9% starch (corn starch) followed by residual activity determination using the EnzChek® substrate (EnzChek® Ultra Amylase assay kit, E33651, Molecular Probes).

Purified enzyme samples were diluted to working concentrations of 5 and 10 ppm (micrograms/ml) in enzyme dilution buffer (10 mM acetate, 0.01% Triton X100, 0.125 mM CaCl$_2$, pH 5.0). Twenty microliters enzyme sample was transferred to 96-well PCR MTP and 180 microliters stability buffer (150 mM acetate, 0.01% Triton X100, 0.125 mM CaCl$_2$, pH 4.8, +/−0.9% starch) was added to each well and mixed. The assay was performed using two concentrations of enzyme in duplicates. Before incubation at 90 or 95° C., 20 microliters was withdrawn and stored on ice as unstressed control samples. Incubation was performed in a PCR machine (pH 4.8, 90/95° C., 0.125 mM CaCl$_2$, +/−0.9% starch). Incubation time (minutes) was selected so that residual activity was between 6-84%. If the residual activity is outside this interval then it is indicated by > or <.

After incubation samples were diluted to 10-20 ng enzyme protein/ml in residual activity buffer (100 mM Acetate, 0.01% Triton X100, 0.125 mM CaCl$_2$, pH 5.5) and 25 microliters diluted enzyme was transferred to black 384-well MTP. Residual activity was determined using the EnzChek® substrate by adding 25 microliters substrate solution (100 micrograms/ml) to each well. Fluorescence was determined at 25° C. every minute for 15 minutes using excitation filter at 485-P nm and emission filter at 555 nm (fluorescence reader is Polarstar, BMG). The residual activity was normalized to unstressed control samples for each setup.

Assuming exponential decay half life time (T½ (min)) was calculated using the equation: T½ (min)=T(min)*LN (0.5)/LN(% RA/100), where T is assay incubation time in minutes, and % RA is % residual activity determined in assay.

Using this assay setup the half life time was determined as a measure of thermostability for the reference alpha-amylase and variants thereof as shown in Tables 3-5.

TABLE 3

Conditions:
pH 4.8, 0.125 mM CaCl$_2$, 95° C. in 0.9% starch for 8 minutes
pH 4.8, 0.125 mM CaCl$_2$, 90° C. in buffer for 12 minutes

| Mutations | T½ (min) (pH 4.8, 0.125 mM CaCl$_2$, buffer, 90° C.) | T½ (min) (pH 4.8, 0.125 mM CaCl$_2$, 0.9% starch, 95° C.) |
|---|---|---|
| Reference | 10 | 4 |

TABLE 4

Conditions:
pH 4.8, 0.125 mM CaCl$_2$, 90° C. in 0.9% starch for 90 minutes
pH 4.8, 0.125 mM CaCl$_2$, 90° C. in buffer for 40 minutes

| Mutations | T½ (min) (pH 4.8 0.125 mM CaCl$_2$ buffer 90° C.) | T½ (min) (pH 4.8 0.125 mM CaCl$_2$ 0.9% starch 90° C.) |
|---|---|---|
| K176L F201Y H205Y K213T Q360S D416V R437W | 23 | 58 |
| K176L F201Y H205Y K213T Q360S D416V R437W H133Y | 84 | 122 |
| K176L F201Y H205Y K213T Q360S D416V R437W S239Q | 56 | 153 |
| K176L F201Y H205Y K213T Q360S D416V R437W H316W | 19 | 51 |
| K176L F201Y H205Y K213T Q360S D416V R437W L318W | 25 | 58 |
| K176L F201Y H205Y K213T Q360S D416V R437W *2aH | 22 | 58 |
| K176L F201Y H205Y K213T Q360S D416V R437W N126W | 11 | 43 |
| K176L F201Y H205Y K213T Q360S D416V R437W H68W | 22 | 24 |
| K176L F201Y H205Y K213T Q360S D416V R437W Y158W | 29 | 68 |
| K176L F201Y H205Y K213T Q360S D416V R437W Y156W | 20 | 54 |
| K176L F201Y H205Y K213T Q360S D416V R437W H142W | 26 | 57 |

TABLE 5

Conditions:
pH 4.8, 0.125 mM CaCl$_2$, 95° C. in 0.9% starch for 40, 70 or 90 minutes
pH 4.8, 0.125 mM CaCl$_2$, 95° C. in buffer for 15 or 50 minutes

| Mutations | T½ (min) (pH 4.8 0.125 mM CaCl$_2$ buffer 95° C.) | T½ (min) (pH 4.8 0.125 mM CaCl$_2$ 0.9% starch 95° C.) |
|---|---|---|
| K176L E185P | 42 | 73 |
| *2aH K176L E185P | 42 | 127 |
| *2aH *2bW K176L E185P | 39 | 79 |
| H68W K176L E185P | 43 | 93 |
| G71W K176L E185P | 43 | 95 |
| H142W K176L E185P | 32 | 82 |
| P144W K176L E185P | 48 | 70 |
| Y158W K176L E185P | 36 | 97 |
| K176L E185P F279W | 41 | 110 |
| K176L E185P H316W | 43 | 91 |
| K176L E185P L318W | 34 | 78 |
| K176L E185P *2aH R437W | 44 | 209 |
| K176L F201Y H205Y K213T Q360S D416V R437W H133Y | 20 | 73 |
| K176L F201Y H205Y K213T Q360S D416V R437W | <1 | 40 |
| H142W K176L E185P | 22 | 74 |
| K176L E185P L318W | 18 | 65 |
| *2aH Y158W K176L E185P F201Y H205Y D207V V209D H316W | 25 | 107 |
| *2aH K176L E185P | 36 | 69 |
| *2aH H68W K176L E185P H133Y | 53 | 159 |
| *2aH K176L E185P R437W | 35 | 64 |
| *2aH K176L E185P H316W R437W | 43 | 75 |
| *2aH K176L E185P H316W R437W L318W | 40 | 76 |
| *2aH K176L E185P H316W R437W H133Y | 52 | 102 |
| *2aH K176L E185P H316W R437W Y156W Y158W | 35 | 72 |
| *2aH K176L E185P H316W R437W H142W | 43 | 91 |
| *2aH K176L E185P R437W Q360S | 41 | 78 |
| *2aH K176L E185P R437W Q360S Y156W | 38 | 69 |
| *2aH K176L E185P R437W Q360S H142W | 31 | 71 |
| *2aH K176L E185P R437W Q360S H133Y | 44 | 78 |
| *2aH K176L E185P R437W Q360S H316W | 38 | 85 |

TABLE 5-continued

Conditions:
pH 4.8, 0.125 mM CaCl$_2$, 95° C. in 0.9% starch for 40, 70 or 90 minutes
pH 4.8, 0.125 mM CaCl$_2$, 95° C. in buffer for 15 or 50 minutes

| Mutations | T½ (min) (pH 4.8 0.125 mM CaCl$_2$ buffer 95° C.) | T½ (min) (pH 4.8 0.125 mM CaCl$_2$ 0.9% starch 95° C.) |
|---|---|---|
| *2aH K176L E185P H316W R437W Q360S | 41 | 75 |
| K176L F201Y H205Y K213T Q360S D416V R437W E185P | 37 | 106 |
| K176L F201Y H205Y K213T Q360S D416V R437W E185P H142W | 39 | 91 |
| K176L F201Y H205Y K213T Q360S D416V R437W E185P H68W | 36 | 105 |
| K176L F201Y H205Y K213T Q360S D416V R437W E185P Y158W H133Y | 42 | 67 |
| K176L F201Y H205Y K213T Q360S D416V R437W E185P Y158W H142W | 40 | 85 |
| K176L F201Y H205Y K213T Q360S D416V R437W E185P Y158W Y156W | 35 | 80 |
| K176L F201Y H205Y K213T Q360S D416V R437W E185P Y158W H316W | 50 | 108 |
| K176L F201Y H205Y K213T Q360S D416V R437W E185P Y158W H316L L318W | 27 | 42 |
| *2aH H68W K176L E185P | 32 | 86 |
| *2aH H68W K176L E185P Y158W | 28 | 77 |
| *2aH H68W K176L E185P Y156W | 28 | 64 |
| *2aH H68W K176L E185P F279W | 32 | 121 |
| *2aH H68W K176L E185P F201Y H205Y D207V V209D | 22 | 33 |
| *2aH H68W K176L E185P H133Y | 43 | >280 |

Example 3

Improved Liquefaction Performance of Alpha-Amylase Variants at pH 4.5

A pilot plant scale liquefaction was set up to achieve the starch liquefaction, and a Neocuproine assay was set up to measure the dextrose equivalent (DE) to evaluate the performance of liquefaction.

Starch slurry with final 5.5 ppm Calcium concentration and 34-35% Dry solids content (DS), was prepared in the tank.

Preparation of Starch Slurry:

Approximately 60 L of distilled water was added to the 200 L slurry tank. The agitator was turned on and dust collection system activated for removal of starch dust. Two 50-lb bags of starch (90.39% DS) were added to the mixing water. After all starch was added, a paddle was used to get settled starch moving and keep the entire slurry mixing. The density of the slurry mixture was measured with a hydrometer in a 2 L graduated cylinder. The density was decreased by stepwise addition of distilled water until approximately 1.155 g/mL, near 35% DS.

pH and conductivity probes were immersed in the mixing slurry. pH was adjusted to pH 4.5 (variants) or pH 5.5 (Liquozyme X) with either 1 M HCl or 2 M NaOH. The starch contains 16 ppm Calcium thus final calcium concentration in slurry is 5.5 ppm with 34-35% DS. Conductivity was around 250 pS/cm.

Enzyme at the appropriate dose was added just before running the slurry through the jet.

Variants were dosed at 4.69 micrograms per gram DS and Liquozyme X (reference) was dosed at 75 NU(T)/g DS:

Enzymes with known activity (KNU(T)/g) were dosed as NU(T) per g DS (dilution is weight per volume):

$$\text{Enzyme } (\mu l) = \frac{\text{Starch (g)} \cdot \% \ DS_{Starch} \cdot \text{Dose}\left(\frac{NU(T)}{gDS}\right)}{\text{Enzyme activity}\left(\frac{NU(T)}{gDS}\right) \cdot \text{Dilution}\left(\frac{g}{mL}\right)} \cdot 1000 \frac{\mu l}{mL}$$

Enzymes with known protein concentration (ug EP/mL) were dosed as ug enzyme protein per g DS (dilution is volume per volume):

$$\text{Enzyme } (\mu l) = \frac{\text{Starch (g)} \cdot \% \ DS_{Starch} \cdot \text{Dose}\left(\frac{\mu g}{gDS}\right)}{\text{Enzyme Conc}\left(\frac{mg}{mL}\right) \cdot \text{Dilution}\left(\frac{mL}{mL}\right)} \cdot 1000 \frac{\mu l}{mL}$$

Slurry was pumped to the jet and held for 5 minutes at around 105° C. as the primary liquefaction. After 10 minutes (approximately 2 retention times) a sample was taken out.

After that, liquefied starch was transferred to the oil bath at 95-97° C. for additional 15, 30, 45, 60, 75 and 90 minutes as the secondary liquefaction.

After primary and secondary liquefaction, starch was hydrolyzed into maltodextrins, during which reducing sugars were liberated.

Copper ions were reduced by the reducing sugars and reacted with Neocuproine reagent to form a colored complex, which gave the content of the reducing sugars in the liquefacts. This value was reported as the dextrose equivalent (DE) as indication of the degree of liquefaction. The higher the DE value is, the more advanced liquefaction has been achieved.

A volumetric flask (500 mL) was prepared for each sample by adding approximately 250 mL DDI water and 400 μl 1 M HCl. With each liquefact sample, the flask was tared and approximately 0.50 g of sample was added to the flask, recording the weight. Solids content of the 90 min sample was determined from RI analysis. DE measurements were performed in duplicates.

The flasks were brought to volume with DDI water and stir bars were added. After inverting several times to mix, the flasks were placed on a multi-point magnetic stir plate.

Method for Dextrose Equivalents (DE)

Dextrose equivalents (DE) were assayed as described below. Place 200 μl of the above samples from the flask to 15 ml conical tube. Add 0.8 ml of reagent A and B each (made according to the composition written below).

Reagent A:

Add 40 g Na$_2$CO$_3$, 16 g of Glycine, 0.45 g of CuSO$_4$.5H$_2$O to 800 ml MQ water in measuring flask and make up the final volume to 1000 ml. Aliquot into 50 ml tubes and wrap in aluminum foil and keep it in the dark.

Reagent B:

Add 1.2 g Neocuproine to 1000 ml MQ water. Aliquot into 50 ml tubes and wrap in aluminum foil and keep it in the dark.

Similar additions are made for the standards and blank (just water) as well. Put them all in the flask stand. Boil the samples for 12 minutes. Stop the reaction immediately by putting all the samples in the ice water. After cooling the samples, add 3.2 ml Milli-Q water. After mixing the samples, measure the OD at 450 nm Create a standard curve from OD readings of glucose standards.

The slope and intercept of the standard curve was used to calculate the reducing end concentrations in the liquefaction samples. The $R^2$ of the standard curve was used to assess the quality of the DE method. The blank were used to determine if the Neocuproine reagents needed to be replaced.

All absorbances were corrected by subtracting the blanks:

$$\text{Corrected OD}_{450} = \text{OD}_{450,Actual} - \text{OD}_{450,Blinds}$$

The concentration of dextrin reducing ends in the sample was calculated from the calibration curve. The RI value was converted to an equivalent % DS by interpolating a DE12 table. The sample DE was calculated:

$$DE = \frac{\text{Reducing ends}\left(\frac{\mu g}{mL}\right)}{\text{Sample (g)} \cdot \% \, DS \cdot \frac{10^6 \, \mu g}{1 \, g} \cdot \frac{1}{\text{Dilution}(X)}} \times 100\%$$

Results in Table 6 showed that all variants gave higher average DE values at pH 4.5 than Liquozyme X at pH 5.5, indicating more efficient and advanced liquefaction.

Example 4

Improved Small Scale Liquefaction Performance of Alpha-Amylase Variants at pH 4.5 and pH 4.8

Small scale liquefaction assay was set up to achieve the starch liquefaction, and a Neocuproine assay was set up to measure the dextrose equivalent (DE) to evaluate the performance of liquefaction.

Low calcium starch (90.32% DS) was weighed out and mixed with DDI water to prepare a 40 g slurry at 33.25% DS. Calcium was added such that the total calcium content was 5 ppm (5 mg/L). Assuming a diluted enzyme and $CaCl_2$ density of 1.0 g/mL, this volume was calculated by:

$$0.25 \, M \, CaCl_2(\mu l) = \frac{\text{Total slurry (g)} \cdot Ca^{++}(mg/L) - \frac{\text{Enzyme (g)}}{\text{Dilution}} \cdot Ca^{++}_{Enzyme}(mg/L)}{40.08 \frac{g \, Ca^{++}}{mol \, CaCl_2} \cdot 0.2495 \frac{mol \, CaCl_2}{L}}$$

Enzyme was added next. Assuming an enzyme density of 1.0 g/mL:

Enzymes with known activity (KNU(T)/g) are dosed as NU(T) per g DS:

TABLE 6

Improved dextrose equivalent (DE) of alpha-amylase variants at pH 4.5 compared to Liquozyme X (reference) at pH 5.5 at around 250 μS/cm, 5.5 ppm Calcium and 34-35% DS. All the variants are variants of Liquozyme X. All results are the average of at least two determinations.

| | | DE | | | | | |
|---|---|---|---|---|---|---|---|
| Mutations | pH | 15 min | 30 min | 45 min | 60 min | 75 min | 90 min |
| Reference | 5.5 | 2.6 | 3.8 | 5.2 | 6.5 | 7.5 | 8.8 |
| K176L F201Y H205Y K213T Q360S D416V R437W E185P | 4.5 | 3.0 | 4.7 | 6.3 | 7.9 | 9.0 | 9.9 |
| K176L F201Y H205Y K213T Q360S D416V R437W E185P H68W | 4.5 | 3.7 | 5.7 | 7.8 | 9.9 | 10.9 | 12.4 |
| K176L F201Y H205Y K213T Q360S D416V R437W E185P H142W | 4.5 | 3.2 | 5.1 | 6.6 | 8.5 | 9.6 | 10.4 |
| K176L F201Y H205Y K213T Q360S D416V R437W E185P Y158W | 4.5 | 1.8 | 3.3 | 4.2 | 5.3 | 6.0 | 6.7 |
| *2aH K176L E185P R437W Q360S H133Y | 4.5 | 2.5 | 4.1 | 5.7 | 7.1 | 8.4 | 9.3 |
| K176L F201Y H205Y K213T Q360S D416V R437W E185P Y158W H133Y | 4.5 | 3.6 | 5.5 | 7.0 | 8.5 | 10.4 | 10.9 |
| K176L F201Y H205Y K213T Q360S D416V R437W E185P Y158W H142W | 4.5 | 2.9 | 4.6 | 6.2 | 7.7 | 9.2 | 9.8 |

$$\text{Enzyme } (\mu l) = \frac{\text{Starch (g)} \cdot \% \ DS_{Starch} \cdot \text{Dose}\left(\frac{NU(T)}{gDS}\right)}{\text{Enzyme Activity}\left(\frac{NU(T)}{g}\right) \cdot \text{Dilution } (X)} \cdot 1\frac{g}{mL} \cdot 1000\frac{\mu l}{mL}$$

Enzymes with known protein concentration (µg EP/mL) are dosed as ug enzyme protein per g DS:

$$\text{Enzyme } (\mu l) = \frac{\text{Starch (g)} \cdot \% \ DS_{Starch} \cdot \text{Dose}\left(\frac{\mu g}{gDS}\right)}{\text{Enzyme } Conc\left(\frac{\mu g}{mL}\right) \cdot \text{Dilution } (X)} \cdot 1000\frac{\mu l}{mL}$$

Often, the enzyme addition would raise the pH by 0.1 or so. The initial pH of the starch slurry was near 4.78. pH was adjusted to pH 4.8 with 1 M HCl as necessary or to pH 4.5 with NaOH. Conductivity was adjusted with 1 M NaCl to 200 µS/cm. Finally, DDI water was added so that the final solids content of the slurry was 32%. A repeater pipette was then used to aliquot 3.3 mL of starch slurry to each vial. Vials were capped and placed in the JKem shaker block.

The shaking block is heated to target temperature for primary step in about 12 minutes. The vials are placed simultaneously in the heating block and the shaking starts. It takes 1 minute for the starch slurry to reach the target temperature of 105.5° C. After 6 minutes, a valve is turned on manually to allow a cooling liquid to pass through the heating block to drop the temperature to 95° C. and the temperature controller is adjusted to 95° C. It takes about 1 minute for the temperature in starch slurry to stabilize at the secondary liquefaction step. The reaction continues at 95° C. for 90 minutes. One vial is removed every 15 minutes for DE measurement, as described above.

TABLE 7

Improved dextrose equivalent (DE) of variants compared to Liquozyme X (reference) in small scale liquefaction assay at pH 4.8, 200 µS/cm, 5 ppm Calcium and enzyme dosage of 4.69 µg enzyme protein/g DS. All the variants are variants of Liquozyme X. All results are the average of at least two determinations.

| Mutations | pH | DE 15 min | 30 min | 45 min | 60 min | 75 min | 90 min |
|---|---|---|---|---|---|---|---|
| Reference | 4.8 | 1.6 | 2.1 | 2.4 | 2.8 | 3.0 | 3.7 |
| S239A | 4.8 | 1.7 | 2.5 | 3.1 | 3.1 | 3.5 | 3.2 |
| K176L | 4.8 | 2.7 | 4.0 | 4.8 | 5.7 | 6.8 | 7.2 |
| *2aW *2bH K176L E185P | 4.8 | 4.1 | | 8.3 | | 11.6 | 12.3 |
| *2aH *2bW K176L E185P | 4.8 | 4.2 | | 7.4 | | 11.1 | 12.7 |
| *2aH K176L E185P | 4.8 | 4.2 | | 8.0 | | 11.8 | 12.5 |
| G71W K176L E185P | 4.8 | 2.6 | 3.6 | 4.9 | 5.6 | 7.1 | 8.4 |
| K176L E185P | 4.8 | 4.3 | 6.3 | 8.2 | 9.5 | 10.9 | 12.1 |
| E185P | 4.8 | 2.6 | 3.9 | 5.0 | 6.4 | 6.9 | 8.3 |
| K176L F201Y H205Y K213T Q360S D416V R437W | 4.8 | 5.6 | 8.4 | 10.6 | 12.7 | 13.4 | 14.9 |
| K176L | 4.8 | 2.8 | 4.2 | 5.9 | 6.2 | 8.3 | 8.8 |

TABLE 8

Improved dextrose equivalent (DE) of variants compared to Liquozyme X (reference) in small scale liquefaction assay at pH 4.8, 200 µS/cm, 5 ppm Calcium and enzyme dosage of 3.127 µg enzyme protein/g DS. All the variants are variants of Liquozyme X. All results are the average of at least two determinations.

| Mutations | pH | DE 15 min | 30 min | 45 min | 60 min | 75 min | 90 min |
|---|---|---|---|---|---|---|---|
| K176L F201Y H205Y K213T Q360S D416V R437W | 4.8 | 3.1 | 4.7 | 5.6 | 7.2 | 8.4 | 8.6 |
| K176L F201Y H205Y K213T Q360S D416V R437W E185P H68W | 4.8 | | | | | | 13.8 |
| K176L F201Y H205Y K213T Q360S D416V R437W L318W | 4.8 | 2.7 | 3.7 | 3.9 | 4.6 | 5.6 | 7.3 |
| K176L F201Y H205Y K213T Q360S D416V R437W H316W | 4.8 | 2.9 | 3.9 | 4.4 | 5.9 | 6.4 | 7.2 |
| K176L F201Y H205Y K213T Q360S D416V R437W H133Y | 4.8 | 3.3 | 4.8 | 5.8 | 7.7 | 8.8 | 9.6 |
| K176L F201Y H205Y K213T Q360S D416V R437W H142W | 4.8 | | | | | | 8.4 |
| K176L F201Y H205Y K213T Q360S D416V R437W Y156W | 4.8 | | | | | | 6.6 |

TABLE 8-continued

Improved dextrose equivalent (DE) of variants compared to Liquozyme X (reference) in small scale liquefaction assay at pH 4.8, 200 μS/cm, 5 ppm Calcium and enzyme dosage of 3.127 μg enzyme protein/g DS. All the variants are variants of Liquozyme X. All results are the average of at least two determinations.

| Mutations | pH | DE | | | | | |
|---|---|---|---|---|---|---|---|
| | | 15 min | 30 min | 45 min | 60 min | 75 min | 90 min |
| K176L F201Y H205Y K213T Q360S D416V R437W Y158W | 4.8 | | | | | | 7.3 |
| K176L F201Y H205Y K213T Q360S D416V R437W H68W | 4.8 | | | | | | 6.8 |
| *2aH K176L F201Y H205Y K213T Q360S D416V R437W | 4.8 | 3.0 | 4.4 | 5.6 | 7.1 | 7.3 | 8.9 |
| K176L F201Y H205Y K213T Q360S D416V R437W N126W | 4.8 | 1.3 | 2.5 | 1.8 | 2.2 | 2.6 | 2.7 |

TABLE 9

Improved dextrose equivalent (DE) of variants compared to Liquozyme X (reference) in small scale liquefaction assay at pH 4.5, 200 μS/cm, 5 ppm Calcium and enzyme dosage of 4.69 μg enzyme protein/g DS. All the variants are variants of Liquozyme X. All results are the average of at least two determinations.

| Mutations | pH | DE | | | | | |
|---|---|---|---|---|---|---|---|
| | | 15 min | 30 min | 45 min | 60 min | 75 min | 90 min |
| Reference | 5.5 | 3.3 | 5.1 | 6.5 | 8.0 | 9.2 | 10.3 |
| K176L F201Y H205Y K213T Q360S D416V R437W | 4.5 | 2.8 | 5.0 | 5.0 | 5.3 | 6.1 | 5.6 |
| K176L E185P | 4.5 | 3.2 | 5.4 | 5.9 | 7.4 | 8.4 | 9.0 |
| H142W K176L E185P | 4.5 | 3.3 | | 6.0 | | 8.7 | 8.3 |
| H68W K176L E185P | 4.5 | 3.0 | | 5.4 | | 7.0 | 7.1 |
| Y158W K176L E185P | 4.5 | 3.0 | | 5.8 | | 8.6 | 8.8 |
| K176L E185P F279W | 4.5 | 2.9 | | 5.0 | | 6.2 | 7.2 |
| *2aH K176L E185P | 4.5 | 3.5 | | 6.2 | | 8.3 | 8.8 |
| K176L E185P H316W | 4.5 | 3.3 | | 6.2 | | 9.5 | 9.9 |
| *2aH *2bW K176L E185P | 4.5 | 3.3 | | 5.1 | | 7.7 | 7.5 |
| K176L E185P L318W | 4.5 | 3.3 | | 5.9 | | 6.5 | 8.5 |
| *2aW *2bH K176L E185P | 4.5 | 3.9 | | 6.1 | | 9.0 | 8.8 |
| K176L F201Y H205Y Q360S D416V R437W | 4.5 | 2.7 | | 5.6 | | 5.5 | 6.8 |
| K176L F201Y H205Y K213T D416V R437W | 4.5 | 2.3 | | 3.1 | | 3.8 | 3.9 |
| K176L F201Y H205Y K213T Q360S R437W | 4.5 | 2.0 | | 4.1 | | 3.9 | 7.0 |
| K176L F201Y H205Y K213T Q360S D416V R437W E185P | 4.5 | 5.6 | 9.2 | 11.9 | 12.4 | 14.3 | 15.1 |
| *2aH H68W K176L E185P Y156W | 4.5 | 2.7 | | 5.6 | | 7.0 | 7.5 |
| *2aH H68W K176L E185P F279W | 4.5 | 2.9 | 4.7 | 6.3 | 7.1 | 7.7 | 9.1 |
| *2aH H68W K176L E185P H133Y | 4.5 | 3.3 | | 6.4 | | 9.1 | 10.3 |
| K176L F201Y H205Y K213T Q360S D416V R437W E185P H68W | 4.5 | 5.9 | 9.1 | 11.4 | 12.8 | 14.3 | 15.0 |
| K176L F201Y H205Y K213T Q360S D416V R437W E185P H142W | 4.5 | 6.0 | 9.8 | 10.6 | 13.1 | 14.6 | 14.5 |
| K176L F201Y H205Y K213T Q360S D416V R437W E185P Y158W | 4.5 | 5.2 | | 10.1 | 12.9 | 13.4 | 14.4 |
| *2aA *2bH K176L E185P H316W L318W R437W | 4.5 | 3.3 | | 6.9 | 7.6 | 9.5 | 11.0 |
| *2aA *2bH H133Y K176L E185P H316W R437W | 4.5 | 3.9 | | 7.4 | 9.1 | 9.9 | 10.7 |
| Y156W Y158W K176L E185P H316W R437W | 4.5 | 1.8 | | 3.1 | | 4.3 | 5.3 |
| H133Y Y158W K176L E185P F201Y H205Y K213T Q360S D416V R437W | 4.5 | 5.8 | | 11.1 | | 13.8 | 15.8 |
| Y158W K176L E185P F201Y H205Y D207V V209D H316W | 4.5 | 3.3 | | 6.3 | 7.2 | 9.1 | 9.6 |
| Y156W K176L E185P Q360S R437W | 4.5 | 4.4 | | 8.6 | 9.7 | 11.8 | 12.6 |

TABLE 9-continued

Improved dextrose equivalent (DE) of variants compared to Liquozyme X (reference) in small scale liquefaction assay at pH 4.5, 200 µS/cm, 5 ppm Calcium and enzyme dosage of 4.69 µg enzyme protein/g DS. All the variants are variants of Liquozyme X. All results are the average of at least two determinations.

| Mutations | pH | DE | | | | | |
|---|---|---|---|---|---|---|---|
| | | 15 min | 30 min | 45 min | 60 min | 75 min | 90 min |
| *2aH K176L E185P R437W Q360S H133Y | 4.5 | 7.8 | | 13.3 | 16.4 | 18.0 | 20.2 |
| *2aH K176L E185P R437W Q360S H316W | 4.5 | 5.4 | | 10.2 | 10.6 | 12.8 | 13.1 |
| K176L E185P F201Y H205Y R437W | 4.5 | 1.7 | | 3.3 | | 4.6 | 4.9 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant comprising a substitution at a position corresponding to position 176 of SEQ ID NO: 1 and an alteration at a position corresponding to position 68, 126, 156, 205, 360, 416 or 437 of SEQ ID NO: 1, wherein the variant has at least 90% and less than 100% sequence identity to SEQ ID NO: 14; and the variant has alpha-amylase activity.

2. The alpha-amylase variant of claim 1, wherein the substitution at a position corresponding to position 176 is with Leu.

3. The alpha-amylase variant of claim 1, wherein the alteration at a position corresponding to position 68 is a substitution with Ala, Arg, Asn, Asp, Cys, Gln, Glu, Gly, Ile, Leu, Lys, Met, Phe, Pro, Ser, Thr, Trp, Tyr or Val.

4. The alpha-amylase variant of claim 1, wherein the alteration at a position corresponding to position 68 is a substitution with Phe, Tyr or Trp.

5. The alpha-amylase variant of claim 1, wherein the alteration at a position corresponding to position 126 is a substitution with Ala, Arg, Asp, Cys, Gln, Glu, Gly, His, Ile, Leu, Lys, Met, Phe, Pro, Ser, Thr, Trp, Tyr or Val.

6. The alpha-amylase variant of claim 1, wherein the alteration at a position corresponding to position 126 is a substitution with Phe, His, Tyr or Trp.

7. The alpha-amylase variant of claim 1, wherein the alteration at a position corresponding to position 156 is a substitution with Ala, Arg, Asn, Asp, Cys, Gln, Glu, Gly, Ile, Leu, Lys, Met, Phe, Pro, Ser, Thr, Trp or Val.

8. The alpha-amylase variant of claim 1, wherein the alteration at a position corresponding to position 156 is a substitution with Phe or Trp.

9. The alpha-amylase variant of claim 1, wherein the alteration at a position corresponding to position 205 is a substitution with Ala, Arg, Asn, Asp, Cys, Gln, Glu, Gly, Ile, Leu, Lys, Met, Phe, Pro, Ser, Thr, Trp, Tyr or Val.

10. The alpha-amylase variant of claim 1, wherein the alteration at a position corresponding to position 205 is a substitution with Tyr.

11. The alpha-amylase variant of claim 1, wherein the alteration at a position corresponding to position 360 is a substitution with Ala, Arg, Asn, Asp, Cys, Glu, Gly, His, Ile, Leu, Lys, Met, Phe, Pro, Ser, Thr, Trp, Tyr or Val.

12. The alpha-amylase variant of claim 1, wherein the alteration at a position corresponding to position 360 is a substitution with Ser.

13. The alpha-amylase variant of claim 1, wherein the alteration at a position corresponding to position 416 is a substitution with Ala, Arg, Cys, Gln, Glu, Gly, His, Ile, Leu, Lys, Met, Phe, Pro, Ser, Thr, Trp, Tyr or Val.

14. The alpha-amylase variant of claim 1, wherein the alteration at a position corresponding to position 416 is a substitution with Val.

15. The alpha-amylase variant of claim 1, wherein the alteration at a position corresponding to position 437 is a substitution with Ala, Asn, Asp, Cys, Gln, Glu, Gly, His, Ile, Leu, Lys, Met, Phe, Pro, Ser, Thr, Trp, Tyr or Val.

16. The alpha-amylase variant of claim 1, wherein the alteration at a position corresponding to position 437 is a substitution with Phe, His, Tyr or Trp.

17. The alpha-amylase variant of claim 1, wherein the variant has at least 95% sequence identity to SEQ ID NO: 14.

18. The alpha-amylase variant of claim 1, further comprising an alteration at one or more positions corresponding to any of positions 1, 2, 71, 133, 142, 144, 158, 185, 201, 213, 239, 279, 316, 318, and 450 of SEQ ID NO: 1.

19. A detergent composition comprising the alpha-amylase variant of claim 1 and a surfactant.

20. A method of producing liquefied starch, comprising liquefying a starch-containing material with the alpha-amylase variant of claim 1.

21. The alpha-amylase variant of claim 1, comprising one of the following sets of substitutions:
N2H+H68W+H133Y+K176L+E185P,
N2H+H68W+Y156W+K176L+E185P,
N2H+H68W+Y158W+K176L+E185P,
N2H+H68W+K176L+E185P,
N2H+H68W+K176L+E185P+I201Y+H205Y+D207V+ V209D,
N2H+H68W+K176L+E185P+F279W,
N2H+H133Y+K176L+E185P+H316W+R437W,
N2H+H133Y+K176L+E185P+Q360S+R437W,
N2H+H142W+K176L+E185P+H316W+R437W,
N2H+H142W+K176L+E185P+Q360S+R437W,
N2H+Y156W+Y158W+K176L+E185P+H316W+ R437W,
N2H+Y156W+K176L+E185P+Q360S+R437W,
N2H+Y158W+K176L+E185P+I201Y+H205Y+D207V+ V209D+H316W,
N2H+K176L+E185P+H316W+L318W+R437W,
N2H+K176L+E185P+H316W+Q360S+R437W,
N2H+K176L+E185P+H316W+R437W,
N2H+K176L+E185P+Q360S+R437W,
N2H+K176L+E185P+R437W,
N2H+K176L+I201Y+H205Y+K213T+Q360S+D416V+ R437W,
H68W+K176L+E185P,
H68W+K176L+E185P+I201Y+H205Y+K213T+ Q360S+D416V+R437W,
H68W+K176L+I201Y+H205Y+K213T+Q360S+ D416V+R437W,
N126W+K176L+I201Y+H205Y+K213T+Q360S+ D416V+R437W,
H133Y+Y158W+K176L+E185P+I201Y+H205Y+ K213T+Q360S+D416V+R437W,
H133Y+K176L+I201Y+H205Y+K213T+Q360S+ D416V+R437W,
H142W+Y158W+K176L+E185P+I201Y+H205Y+ K213T+Q360S+D416V+R437W,
H142W+K176L+E185P+I201Y+H205Y+K213T+ Q360S+D416V+R437W,
H142W+K176L+I201Y+H205Y+K213T+Q360S+ D416V+R437W,
Y156W+Y158W+K176L+E185P+I201Y+H205Y+ K213T+Q360S+D416V+R437W,
Y156W+Y158W+K176L+E185P+H316W+R437W,
Y156W+K176L+E185P+Q360S+R437W,
Y156W+K176L+I201Y+H205Y+K213T+Q360S+ D416V+R437W,
Y158W+K176L+E185P+I201Y+H205Y+D207V+ V209D+H316W,
Y158W+K176L+E185P+I201Y+H205Y+K213T+ H316L+L318W+Q360S+D416V+R437W,
Y158W+K176L+E185P+I201Y+H205Y+K213T+ H316W+Q360S+D416V+R437W,
Y158W+K176L+E185P+I201Y+H205Y+K213T+ Q360S+D416V+R437W,
Y158W+K176L+I201Y+H205Y+K213T+Q360S+ D416V+R437W,
K176L+E185P+I201Y+H205Y+K213T+Q360S+ D416V+R437W,
K176L+E185P+I201Y+H205Y+R437W, K176L+I201Y+H205Y+K213T+S239Q+Q360S+
D416V+R437W,
K176L+I201Y+H205Y+K213T+H316W+Q360S+
D416V+R437W,
K176L+I201Y+H205Y+K213T+L318W+Q360S+
D416V+R437W,
K176L+I201Y+H205Y+K213T+Q360S+D416V+
R437W,
K176L+I201Y+H205Y+K213T+Q360S+R437W,
K176L+I201Y+H205Y+K213T+D416V+R437W, or
K176L+I201Y+H205Y+Q360S+D416V+R437W.

* * * * *

SEQUENCE LISTING

```
<160> NUMBER OF SEQ ID NOS: 14

<210> SEQ ID NO 1
<211> LENGTH: 483
<212> TYPE: PRT
<213> ORGANISM: Bacillus licheniformis

<400> SEQUENCE: 1

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
```

```
                210                 215                 220
Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Gly Tyr Asp Met
                290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
                370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
                450                 455                 460

Glu Gly Trp Gly Glu Phe His Val Asn Gly Gly Ser Val Ser Ile Tyr
465                 470                 475                 480

Val Gln Arg

<210> SEQ ID NO 2
<211> LENGTH: 515
<212> TYPE: PRT
<213> ORGANISM: Bacillus stearothermophilus

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
                35                  40                  45

Gly Thr Ser Arg Ser Asp Val Gly Tyr Gly Val Tyr Asp Leu Tyr Asp
                50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
```

```
                100             105             110
Thr Glu Trp Val Asp Ala Val Glu Val Asn Pro Ser Asp Arg Asn Gln
            115                 120                 125
Glu Ile Ser Gly Thr Tyr Gln Ile Gln Ala Trp Thr Lys Phe Asp Phe
            130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
                180                 185                 190
Asn Gly Asn Tyr Asp Tyr Leu Met Tyr Ala Asp Leu Asp Met Asp His
                195                 200                 205
Pro Glu Val Val Thr Glu Leu Lys Asn Trp Gly Lys Trp Tyr Val Asn
                210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
                260                 265                 270
Leu His Asn Tyr Ile Thr Lys Thr Asn Gly Thr Met Ser Leu Phe Asp
                275                 280                 285
Ala Pro Leu His Asn Lys Phe Tyr Thr Ala Ser Lys Ser Gly Gly Ala
                290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
                340                 345                 350
Phe Ile Leu Thr Arg Gln Glu Gly Tyr Pro Cys Val Phe Tyr Gly Asp
                355                 360                 365
Tyr Tyr Gly Ile Pro Gln Tyr Asn Ile Pro Ser Leu Lys Ser Lys Ile
                370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
                420                 425                 430
Gly Gly Ser Lys Trp Met Tyr Val Gly Lys Gln His Ala Gly Lys Val
                435                 440                 445
Phe Tyr Asp Leu Thr Gly Asn Arg Ser Asp Thr Val Thr Ile Asn Ser
                450                 455                 460
Asp Gly Trp Gly Glu Phe Lys Val Asn Gly Gly Ser Val Ser Val Trp
465                 470                 475                 480
Val Pro Arg Lys Thr Thr Val Ser Thr Ile Ala Arg Pro Ile Thr Thr
                485                 490                 495
Arg Pro Trp Thr Gly Glu Phe Val Arg Trp Thr Glu Pro Arg Leu Val
                500                 505                 510
Ala Trp Pro
                515
```

<210> SEQ ID NO 3
<211> LENGTH: 584
<212> TYPE: PRT
<213> ORGANISM: Bacillus

<400> SEQUENCE: 3

```
Ala Asn Thr Ala Pro Ile Asn Glu Thr Met Met Gln Tyr Phe Glu Trp
1               5                   10                  15

Asp Leu Pro Asn Asp Gly Thr Leu Trp Thr Lys Val Lys Asn Glu Ala
            20                  25                  30

Ala Asn Leu Ser Ser Leu Gly Ile Thr Ala Leu Trp Leu Pro Pro Ala
        35                  40                  45

Tyr Lys Gly Thr Ser Gln Ser Asp Val Gly Tyr Gly Val Tyr Asp Leu
    50                  55                  60

Tyr Asp Leu Gly Glu Phe Asn Gln Lys Gly Thr Ile Arg Thr Lys Tyr
65                  70                  75                  80

Gly Thr Lys Thr Gln Tyr Ile Gln Ala Ile Gln Ala Ala Lys Ala Ala
                85                  90                  95

Gly Met Gln Val Tyr Ala Asp Val Val Phe Asn His Lys Ala Gly Ala
            100                 105                 110

Asp Gly Thr Glu Phe Val Asp Ala Val Glu Val Asp Pro Ser Asn Arg
        115                 120                 125

Asn Gln Glu Thr Ser Gly Thr Tyr Gln Ile Gln Ala Trp Thr Lys Phe
    130                 135                 140

Asp Phe Pro Gly Arg Gly Asn Thr Tyr Ser Ser Phe Lys Trp Arg Trp
145                 150                 155                 160

Tyr His Phe Asp Gly Thr Asp Trp Asp Glu Ser Arg Lys Leu Asn Arg
                165                 170                 175

Ile Tyr Lys Phe Arg Ser Thr Gly Lys Ala Trp Asp Trp Glu Val Asp
            180                 185                 190

Thr Glu Asn Gly Asn Tyr Asp Tyr Leu Met Phe Ala Asp Leu Asp Met
        195                 200                 205

Asp His Pro Glu Val Val Thr Glu Leu Lys Asn Trp Gly Thr Trp Tyr
    210                 215                 220

Val Asn Thr Thr Asn Ile Asp Gly Phe Arg Leu Asp Ala Val Lys His
225                 230                 235                 240

Ile Lys Tyr Ser Phe Phe Pro Asp Trp Leu Thr Tyr Val Arg Asn Gln
                245                 250                 255

Thr Gly Lys Asn Leu Phe Ala Val Gly Glu Phe Trp Ser Tyr Asp Val
            260                 265                 270

Asn Lys Leu His Asn Tyr Ile Thr Lys Thr Asn Gly Ser Met Ser Leu
        275                 280                 285

Phe Asp Ala Pro Leu His Asn Asn Phe Tyr Thr Ala Ser Lys Ser Ser
    290                 295                 300

Gly Tyr Phe Asp Met Arg Tyr Leu Leu Asn Asn Thr Leu Met Lys Asp
305                 310                 315                 320

Gln Pro Ser Leu Ala Val Thr Leu Val Asp Asn His Asp Thr Gln Pro
                325                 330                 335

Gly Gln Ser Leu Gln Ser Trp Val Glu Pro Trp Phe Lys Pro Leu Ala
            340                 345                 350

Tyr Ala Phe Ile Leu Thr Arg Gln Glu Gly Tyr Pro Cys Val Phe Tyr
        355                 360                 365

Gly Asp Tyr Tyr Gly Ile Pro Lys Tyr Asn Ile Pro Gly Leu Lys Ser
```

```
                370                 375                 380
Lys Ile Asp Pro Leu Leu Ile Ala Arg Arg Asp Tyr Ala Tyr Gly Thr
385                 390                 395                 400

Gln Arg Asp Tyr Ile Asp His Gln Asp Ile Ile Gly Trp Thr Arg Glu
                405                 410                 415

Gly Ile Asp Thr Lys Pro Asn Ser Gly Leu Ala Ala Leu Ile Thr Asp
                420                 425                 430

Gly Pro Gly Gly Ser Lys Trp Met Tyr Val Gly Lys Lys His Ala Gly
                435                 440                 445

Lys Val Phe Tyr Asp Leu Thr Gly Asn Arg Ser Asp Thr Val Thr Ile
                450                 455                 460

Asn Ala Asp Gly Trp Gly Glu Phe Lys Val Asn Gly Gly Ser Val Ser
465                 470                 475                 480

Ile Trp Val Ala Lys Thr Ser Asn Val Thr Phe Thr Val Asn Asn Ala
                485                 490                 495

Thr Thr Thr Ser Gly Gln Asn Val Tyr Val Val Ala Asn Ile Pro Glu
                500                 505                 510

Leu Gly Asn Trp Asn Thr Ala Asn Ala Ile Lys Met Asn Pro Ser Ser
                515                 520                 525

Tyr Pro Thr Trp Lys Ala Thr Ile Ala Leu Pro Gln Gly Lys Ala Ile
                530                 535                 540

Glu Phe Lys Phe Ile Lys Lys Asp Gln Ala Gly Asn Val Ile Trp Glu
545                 550                 555                 560

Ser Thr Ser Asn Arg Thr Tyr Thr Val Pro Phe Ser Ser Thr Gly Ser
                565                 570                 575

Tyr Thr Ala Ser Trp Asn Val Pro
                580

<210> SEQ ID NO 4
<211> LENGTH: 584
<212> TYPE: PRT
<213> ORGANISM: Bacillus flavothermus

<400> SEQUENCE: 4

Val Pro Val Asn Gly Thr Met Met Gln Tyr Phe Glu Trp Tyr Leu Pro
1               5                   10                  15

Asp Asp Gly Thr Leu Trp Thr Lys Val Ala Asn Asn Ala Gln Ser Leu
                20                  25                  30

Ala Asn Leu Gly Ile Thr Ala Leu Trp Leu Pro Pro Ala Tyr Lys Gly
            35                  40                  45

Thr Ser Ser Ser Asp Val Gly Tyr Gly Val Tyr Asp Leu Tyr Asp Leu
        50                  55                  60

Gly Glu Phe Asn Gln Lys Gly Thr Val Arg Thr Lys Tyr Gly Thr Lys
65              70                  75                  80

Thr Gln Tyr Ile Gln Ala Ile Gln Ala Ala His Thr Ala Gly Met Gln
                85                  90                  95

Val Tyr Ala Asp Val Val Phe Asn His Lys Ala Gly Ala Asp Gly Thr
                100                 105                 110

Glu Leu Val Asp Ala Val Glu Val Asn Pro Ser Asp Arg Asn Gln Glu
            115                 120                 125

Ile Ser Gly Thr Tyr Gln Ile Gln Ala Trp Thr Lys Phe Asp Phe Pro
        130                 135                 140

Gly Arg Gly Asn Thr Tyr Ser Ser Phe Lys Trp Arg Trp Tyr His Phe
145             150                 155                 160
```

```
Asp Gly Thr Asp Trp Asp Glu Ser Arg Lys Leu Asn Arg Ile Tyr Lys
            165                 170                 175

Phe Arg Gly Thr Gly Lys Ala Trp Asp Trp Glu Val Asp Thr Glu Asn
        180                 185                 190

Gly Asn Tyr Asp Tyr Leu Met Tyr Ala Asp Leu Asp Met Asp His Pro
            195                 200                 205

Glu Val Val Ser Glu Leu Lys Asn Trp Gly Lys Trp Tyr Val Thr Thr
        210                 215                 220

Thr Asn Ile Asp Gly Phe Arg Leu Asp Ala Val Lys His Ile Lys Tyr
225                 230                 235                 240

Ser Phe Phe Pro Asp Trp Leu Ser Tyr Val Arg Thr Gln Thr Gln Lys
            245                 250                 255

Pro Leu Phe Ala Val Gly Glu Phe Trp Ser Tyr Asp Ile Ser Lys Leu
        260                 265                 270

His Asn Tyr Ile Thr Lys Thr Asn Gly Ser Met Ser Leu Phe Asp Ala
            275                 280                 285

Pro Leu His Asn Asn Phe Tyr Ile Ala Ser Lys Ser Gly Gly Tyr Phe
        290                 295                 300

Asp Met Arg Thr Leu Leu Asn Asn Thr Leu Met Lys Asp Gln Pro Thr
305                 310                 315                 320

Leu Ala Val Thr Leu Val Asp Asn His Asp Thr Glu Pro Gly Gln Ser
            325                 330                 335

Leu Gln Ser Trp Val Glu Pro Trp Phe Lys Pro Leu Ala Tyr Ala Phe
        340                 345                 350

Ile Leu Thr Arg Gln Glu Gly Tyr Pro Cys Val Phe Tyr Gly Asp Tyr
            355                 360                 365

Tyr Gly Ile Pro Lys Tyr Asn Ile Pro Ala Leu Lys Ser Lys Leu Asp
        370                 375                 380

Pro Leu Leu Ile Ala Arg Arg Asp Tyr Ala Tyr Gly Thr Gln His Asp
385                 390                 395                 400

Tyr Ile Asp Ser Ala Asp Ile Ile Gly Trp Thr Arg Glu Gly Val Ala
            405                 410                 415

Glu Lys Ala Asn Ser Gly Leu Ala Ala Leu Ile Thr Asp Gly Pro Gly
        420                 425                 430

Gly Ser Lys Trp Met Tyr Val Gly Lys Gln His Ala Gly Lys Thr Phe
            435                 440                 445

Tyr Asp Leu Thr Gly Asn Arg Ser Asp Thr Val Thr Ile Asn Ala Asp
        450                 455                 460

Gly Trp Gly Glu Phe Lys Val Asn Gly Gly Ser Val Ser Ile Trp Val
465                 470                 475                 480

Pro Lys Ile Ser Thr Thr Ser Gln Ile Thr Phe Thr Val Asn Asn Ala
            485                 490                 495

Thr Thr Val Trp Gly Gln Asn Val Tyr Val Val Gly Asn Ile Ser Gln
        500                 505                 510

Leu Gly Asn Trp Asp Pro Val His Ala Val Gln Met Thr Pro Ser Ser
            515                 520                 525

Tyr Pro Thr Trp Thr Val Thr Ile Pro Leu Leu Gln Gly Gln Asn Ile
        530                 535                 540

Gln Phe Lys Phe Ile Lys Lys Asp Ser Ala Gly Asn Val Ile Trp Glu
545                 550                 555                 560

Asp Ile Ser Asn Arg Thr Tyr Thr Val Pro Thr Ala Ala Ser Gly Ala
            565                 570                 575

Tyr Thr Ala Ser Trp Asn Val Pro
```

-continued

```
                  580

<210> SEQ ID NO 5
<211> LENGTH: 586
<212> TYPE: PRT
<213> ORGANISM: Bacillus

<400> SEQUENCE: 5

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Ile Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Leu Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
    290                 295                 300

Tyr Phe Asp Met Arg Thr Leu Leu Asn Asn Thr Leu Met Lys Glu Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365
```

```
Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Pro Lys Thr Ser Thr Ser Gln Ile Thr Phe Thr Val Asn
                485                 490                 495

Asn Ala Thr Thr Val Trp Gly Gln Asn Val Tyr Val Val Gly Asn Ile
                500                 505                 510

Ser Gln Leu Gly Asn Trp Asp Pro Val Asn Ala Val Gln Met Thr Pro
        515                 520                 525

Ser Ser Tyr Pro Thr Trp Val Thr Val Pro Leu Pro Gln Ser Gln
530                 535                 540

Asn Ile Gln Phe Lys Phe Ile Lys Lys Asp Gly Ser Gly Asn Val Ile
545                 550                 555                 560

Trp Glu Asn Ile Ser Asn Arg Thr Tyr Thr Val Pro Thr Ala Ala Ser
                565                 570                 575

Gly Ala Tyr Thr Ala Asn Trp Asn Val Pro
            580                 585

<210> SEQ ID NO 6
<211> LENGTH: 483
<212> TYPE: PRT
<213> ORGANISM: Bacillus amyloliquefaciens

<400> SEQUENCE: 6

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
                100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
130                 135                 140

Gly Asn Thr Tyr Ser Asp Phe Lys Trp His Trp Tyr His Phe Asp Gly
145                 150                 155                 160
```

Ala Asp Trp Asp Glu Ser Arg Lys Ile Ser Arg Ile Phe Lys Phe Arg
            165                 170                 175

Gly Glu Gly Lys Ala Trp Asp Trp Glu Val Ser Ser Glu Asn Gly Asn
        180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
            245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Gly Tyr Asp Met
            290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
            370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480

Val Gln Lys

<210> SEQ ID NO 7
<211> LENGTH: 485
<212> TYPE: PRT
<213> ORGANISM: Bacillus sp.

<400> SEQUENCE: 7

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

```
Lys Gly Thr Ser Gln Asn Asp Val Gly Tyr Gly Ala Tyr Asp Leu Tyr
         50                  55                  60

Asp Leu Gly Glu Phe Asn Gln Lys Gly Thr Val Arg Thr Lys Tyr Gly
 65                  70                  75                  80

Thr Arg Asn Gln Leu Gln Ala Ala Val Thr Ser Leu Lys Asn Asn Gly
                     85                  90                  95

Ile Gln Val Tyr Gly Asp Val Val Met Asn His Lys Gly Gly Ala Asp
                    100                 105                 110

Gly Thr Glu Ile Val Asn Ala Val Glu Val Asn Arg Ser Asn Arg Asn
                115                 120                 125

Gln Glu Thr Ser Gly Glu Tyr Ala Ile Glu Ala Trp Thr Lys Phe Asp
            130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
                180                 185                 190

Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
                260                 265                 270

Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460
```

```
Asn Ala Asp Gly Trp Gly Asn Phe Ser Val Asn Gly Ser Val Ser
465                 470                 475                 480

Val Trp Val Lys Gln
            485

<210> SEQ ID NO 8
<211> LENGTH: 485
<212> TYPE: PRT
<213> ORGANISM: Bacillus halmapalus

<400> SEQUENCE: 8

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350
```

```
Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
        370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Asn Lys Ala Gly
        435                 440                 445

Gln Val Trp His Asp Ile Thr Gly Asn Lys Pro Gly Thr Val Thr Ile
        450                 455                 460

Asn Ala Asp Gly Trp Ala Asn Phe Ser Val Asn Gly Gly Ser Val Ser
465                 470                 475                 480

Ile Trp Val Lys Arg
            485

<210> SEQ ID NO 9
<211> LENGTH: 485
<212> TYPE: PRT
<213> ORGANISM: Bacillus sp.

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
```

```
            225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
                275                 280                 285

Phe Asp Val Pro Leu His Tyr Asn Leu Tyr Asn Ala Ser Lys Ser Gly
            290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Lys Ser
            370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
                450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 10
<211> LENGTH: 485
<212> TYPE: PRT
<213> ORGANISM: Bacillus sp.

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110
```

Ala Thr Glu Trp Val Arg Ala Glu Val Asn Pro Ser Asn Arg Asn
            115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 11
<211> LENGTH: 485
<212> TYPE: PRT
<213> ORGANISM: Bacillus sp.

<400> SEQUENCE: 11

```
His His Asn Gly Thr Asn Gly Thr Met Met Gln Tyr Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
            130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
            210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
            290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
            325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
            405                 410                 415
```

```
Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
        450                 455                 460

Asn Ala Asp Gly Trp Ala Asn Phe Ser Val Asn Gly Ser Val Ser
465                 470                 475                 480

Ile Trp Val Asn Lys
                485

<210> SEQ ID NO 12
<211> LENGTH: 480
<212> TYPE: PRT
<213> ORGANISM: Bacillus sp.

<400> SEQUENCE: 12

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300
```

```
Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
            325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 13
<211> LENGTH: 483
<212> TYPE: PRT
<213> ORGANISM: Bacillus licheniformis

<400> SEQUENCE: 13

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
            85                  90                  95

Val Tyr Gly Asp Val Val Ile Asn His Lys Gly Gly Ala Asp Ala Thr
        100                 105                 110

Glu Asp Val Thr Ala Val Glu Val Asp Pro Ala Asp Arg Asn Arg Val
    115                 120                 125

Ile Ser Gly Glu Tyr Leu Ile Lys Ala Trp Thr His Phe His Phe Pro
130                 135                 140

Gly Arg Gly Ser Thr Tyr Ser Asp Phe Lys Trp Tyr Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Tyr Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
```

```
                195                 200                 205
Val Ala Glu Ile Lys Arg Trp Gly Thr Trp Tyr Ala Asn Glu Leu Gln
210                 215                 220

Leu Asp Gly Asn Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe Tyr Ala Ala Ser Thr Gln Gly Gly Tyr Asp Met
    290                 295                 300

Arg Lys Leu Leu Asn Asp Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp Tyr Asp Ile Thr Gly Asn Arg Ser Glu Pro Val Val Ile Asn Ser
    450                 455                 460

Glu Gly Trp Gly Glu Phe His Val Asn Asp Gly Ser Val Ser Ile Tyr
465                 470                 475                 480

Val Gln Arg

<210> SEQ ID NO 14
<211> LENGTH: 481
<212> TYPE: PRT
<213> ORGANISM: Artificial sequence
<220> FEATURE:
<223> OTHER INFORMATION: Synthetic construct

<400> SEQUENCE: 14

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80
```

```
Leu Gln Ser Ala Ile Lys Ser Leu His Ser Arg Asp Ile Asn Val Tyr
                85                  90                  95
Gly Asp Val Val Ile Asn His Lys Ala Gly Asp Ala Thr Glu Asp
            100                 105                 110
Val Thr Ala Val Glu Val Asp Pro Ala Asp Arg Asn Arg Val Ile Ser
            115                 120                 125
Gly Glu His Leu Ile Lys Ala Trp Thr His Phe His Phe Pro Gly Arg
        130                 135                 140
Gly Ser Thr Tyr Ser Asp Phe Lys Trp Tyr Trp His Phe Asp Gly
145                 150                 155                 160
Thr Asp Trp Asp Glu Ser Arg Lys Leu Asn Arg Ile Tyr Lys Phe Gln
                165                 170                 175
Gly Lys Thr Trp Asp Trp Glu Val Ser Asn Glu Phe Gly Asn Tyr Asp
            180                 185                 190
Tyr Leu Met Tyr Ala Asp Phe Asp Tyr Asp His Pro Asp Val Val Ala
        195                 200                 205
Glu Ile Lys Arg Trp Gly Thr Trp Tyr Ala Asn Glu Leu Gln Leu Asp
        210                 215                 220
Gly Phe Arg Leu Asp Ala Val Lys His Ile Lys Phe Ser Phe Leu Arg
225                 230                 235                 240
Asp Trp Val Asn His Val Arg Glu Lys Thr Gly Lys Glu Met Phe Thr
                245                 250                 255
Val Ala Glu Tyr Trp Ser Asn Asp Leu Gly Ala Leu Glu Asn Tyr Leu
            260                 265                 270
Asn Lys Thr Asn Phe Asn His Ser Val Phe Asp Val Pro Leu His Tyr
        275                 280                 285
Gln Phe His Ala Ala Ser Thr Gln Gly Gly Gly Tyr Asp Met Arg Lys
        290                 295                 300
Leu Leu Asn Gly Thr Val Val Ser Lys His Pro Leu Lys Ser Val Thr
305                 310                 315                 320
Phe Val Asp Asn His Asp Thr Gln Pro Gly Gln Ser Leu Glu Ser Thr
                325                 330                 335
Val Gln Thr Trp Phe Lys Pro Leu Ala Tyr Ala Phe Ile Leu Thr Arg
            340                 345                 350
Glu Ser Gly Tyr Pro Gln Val Phe Tyr Gly Asp Met Tyr Gly Thr Lys
        355                 360                 365
Gly Asp Ser Gln Arg Glu Ile Pro Ala Leu Lys His Lys Ile Glu Pro
        370                 375                 380
Ile Leu Lys Ala Arg Lys Gln Tyr Ala Tyr Gly Ala Gln His Asp Tyr
385                 390                 395                 400
Phe Asp His His Asp Ile Val Gly Trp Thr Arg Glu Gly Asp Ser Ser
                405                 410                 415
Val Ala Asn Ser Gly Leu Ala Ala Leu Ile Thr Asp Gly Pro Gly Gly
            420                 425                 430
Ala Lys Arg Met Tyr Val Gly Arg Gln Asn Ala Gly Glu Thr Trp His
        435                 440                 445
Asp Ile Thr Gly Asn Arg Ser Glu Pro Val Val Ile Asn Ser Glu Gly
        450                 455                 460
Trp Gly Glu Phe His Val Asn Gly Gly Ser Val Ser Ile Tyr Val Gln
465                 470                 475                 480
Arg
```